(12) United States Patent
Kanai et al.

(10) Patent No.: US 8,697,010 B2
(45) Date of Patent: Apr. 15, 2014

(54) DISPENSING DEVICE

(75) Inventors: Masaki Kanai, Kyoto (JP); Takahiro Nishimoto, Kyoto (JP); Masakazu Akechi, Kyoto (JP); Nobuhiro Hanafusa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 646 days.

(21) Appl. No.: 12/746,698

(22) PCT Filed: Dec. 19, 2007

(86) PCT No.: PCT/JP2007/074466
§ 371 (c)(1),
(2), (4) Date: Sep. 28, 2010

(87) PCT Pub. No.: WO2009/078107
PCT Pub. Date: Jun. 25, 2009

(65) Prior Publication Data
US 2011/0036862 A1   Feb. 17, 2011

(51) Int. Cl.
*B01L 99/00* (2010.01)
(52) U.S. Cl.
USPC .......................................... 422/503; 422/504
(58) Field of Classification Search
USPC ........................................ 422/500–504, 507
See application file for complete search history.

(56) References Cited

U.S. PATENT DOCUMENTS

| 2002/0036018 | A1* | 3/2002 | McNeely et al. | 137/806 |
| 2004/0209381 | A1 | 10/2004 | Peters et al. | |
| 2006/0039829 | A1 | 2/2006 | Suk et al. | |
| 2007/0014695 | A1* | 1/2007 | Yue et al. | 422/100 |

FOREIGN PATENT DOCUMENTS

| JP | 2002-527250 A | 8/2002 |
| JP | 2004-163104 A | 6/2004 |
| JP | 2004-226412 A | 8/2004 |
| JP | 2005-114430 A | 4/2005 |
| JP | 2007-523355 A | 8/2007 |
| WO | WO-00/00436 A1 | 4/2000 |

OTHER PUBLICATIONS

Kenai, Masaki at al., "A Multi Cellular Diagnostic Device for High-Throughput Analysis", Proceedings of 8th International Conference on Miniaturized Systems for Chemistry and Life Sciences, 2004, pp. 126-128.
International Search Report for the Application No. PCT/JP2007/074466 mailed Apr. 1, 2008.

* cited by examiner

*Primary Examiner* — Paul Hyun
(74) *Attorney, Agent, or Firm* — Cheng Law Group, PLLC

(57) ABSTRACT

A dispensing device for reducing the dead volume of a liquid sample includes a main channel connected to a sample inlet and sample outlet, and branch channels connected to the main channel. Each branch channel is connected to a different liquid reservoir. High inflow-withstanding pressure sections are provided in the main channel between the branch channels and between the branch channel and the sample outlet. Each high inflow-withstanding pressure section has a channel inner wall forming a contact angle of 90° or larger with a liquid sample. A liquid sample enters the main channel through the sample inlet, reaches a branch point between the first branch channel and the main channel flows into the first branch channel and the liquid reservoir, and then passes through the high inflow-withstanding pressure section to a branch point between the next branch channel and the main channel.

15 Claims, 37 Drawing Sheets

Fig. 44                    Prior Art

DISPENSING DEVICE

CROSS REFERENCE TO RELATED APPLICATIONS

The present application is a 371 application of PCT/JP2007/074466, filed Dec. 19, 2007, the entire contents of which are hereby incorporated by reference into the present application.

BACKGROUND OF THE INVENTION

1. Field of the Invention

The present invention relates to a dispensing device for use in, for example, synthesizing an organic material from a trace amount of a sample in organic chemistry or performing PCR (polymerase chain reaction) in biochemistry. More particularly, the present invention relates to a dispensing device, such as μTAS (Micro Total Analysis System), for use in analysis or reaction of a trace amount of a liquid sample.

2. Description of the Related Art

In the field of μTAS for treating a liquid sample, various devices obtained by integrating a plurality of liquid reservoirs for performing analysis or reaction into one and the same device have been heretofore reported.

In order to efficiently introduce a liquid sample into a plurality of liquid reservoirs integrated into one and the same device, a structure shown in FIG. 44 has been reported (see Non-Patent Document 1), in which a plurality of liquid reservoirs 705 parallelly-connected between a sample inlet 701 and a sample outlet 703, and a sample introduction channel 707 which is arranged so that all channels between the sample inlet 701 and each of the liquid reservoirs 705 have the same resistance to flow. Each of the liquid reservoirs 705 is connected to the sample outlet 703 through a sample outlet 709. By allowing all the channels between the sample inlet 701 and each of the liquid reservoirs 705 in the sample introduction channel 707 to have the same resistance to flow, it is possible to evenly dispense, into the plurality of liquid reservoirs 705, a liquid sample introduced into the sample introduction channel 707 through the sample inlet 701.

Further, a structure for dispensing a trace amount of liquid capable of quantitatively treating a trace amount of a liquid sample has been also reported (see, for example, Patent Documents 2 and 3). This structure comprises a first channel, a second channel, a third channel which is in communication with the first channel through an opening provided in the channel wall of the first channel, and a fourth channel which is in communication with the second channel through an opening, provided in the channel wall of the second channel, connects one end of the third channel to the second channel, and has relatively lower capillary attraction than the third channel. When such a structure for dispensing a trace amount of liquid is used, a liquid introduced into the first channel is drawn into the third channel, and then the liquid remaining in the first channel is removed. As a result, the liquid having a volume corresponding to the capacity of the third channel is dispensed into the second channel.

Patent Document 1: Japanese Patent Application Laid-open No. 2004-163104
Patent Document 2: Japanese Patent Application Laid-open No. 2005-114430
Non Patent Document 1: Masaki Kanai, et al., "A Multi Cellular Diagnostic Device for High-throughput Analysis", The 8th International Conference on Miniaturized Chemistry and Life Science (μTAS2004), Malmo, Sweden, September 26-30, pp. 126-128, 2004

In the case of the channel configuration described in Non-Patent Document 1 as shown in FIG. 44, a liquid sample remaining in the sample introduction channel 707 provided between the sample inlet 701 and the liquid reservoirs 705 is not used for analysis or reaction performed in the liquid reservoirs 705, and is therefore a so-called dead volume. Particularly, in the case of devices for treating a trace amount of a sample such as μTAS, the capacity of a sample introduction channel is larger than that of a liquid reservoir because the capacity of the liquid reservoir is small. This causes a problem in that the ratio of dead volume of a liquid sample is large.

Further, in the case of a dispensing device having the channel configuration described in Non-Patent Document 1, when the number of liquid reservoirs integrated into the dispensing device is increased, the length of the sample introduction channel needs to be increased, thus resulting in a problem in that the dead volume of a liquid sample is increased.

SUMMARY OF THE INVENTION

It is therefore an object of the present invention to provide a dispensing device capable of reducing the dead volume of a liquid sample as compared to a conventional dispensing device.

The present invention is directed to a dispensing device including:
a base substrate;
a cover substrate whose one surface is bonded to one surface of the base substrate;
a liquid reservoir constituted of a recess provided in one or both of the one surface of the base substrate and the one surface of the cover substrate;
a liquid sample introduction channel which is constituted of a groove provided in one or both of the one surface of the base substrate and the one surface of the cover substrate, and which is connected to the liquid reservoir; and
an air vent port which is provided in one or both of the one surface of the base substrate and the one surface of the cover substrate and connected to the liquid reservoir at a position different from a position where the liquid sample introduction channel is connected to the liquid reservoir,
wherein the number of the liquid reservoirs is two or more,
the liquid sample introduction channel includes a main channel whose one end is connected to a sample inlet and whose other end is connected to a sample outlet and a plurality of branch channels connected to the main channel between the sample inlet and the sample outlet,
the branch channels are each connected to the different liquid reservoirs at their ends located on an opposite side from the main channel, and
high inflow-withstanding pressure sections having a higher inflow-withstanding pressure than the branch channel are provided in the main channel between the branch channels and between the branch channel and the sample outlet. Here, the air vent port may be a channel constituted of a groove or a through hole or may be constituted of pores of, for example, a hydrophobic porous membrane.

A series of steps in the process of introducing a liquid sample into the liquid reservoirs in the case of this structure will be described.

A liquid sample introduced into the main channel through the sample inlet toward the sample outlet reaches a branch point between the first branch channel and the main channel. Then, the liquid sample flows into the first branch channel and the liquid reservoir because when the dispensing device is seen from the sample inlet side, the high inflow-withstanding pressure section having a higher inflow-withstanding pressure than the branch channel is provided in the main channel between the first branch point and the next branch point. When the liquid sample flows into the branch channel and the liquid reservoir, a gas contained in the liquid reservoir is discharged through the air vent port. This makes it possible to prevent the formation of gas bubbles in the liquid reservoir after the liquid reservoir is filled with the liquid sample, thereby making it possible to reliably fill the liquid reservoir with a predetermined volume of the liquid sample. At this time, it is preferred that the liquid sample does not flow downstream from the high inflow-withstanding pressure section. However, the liquid sample may flow downstream from the high inflow-withstanding pressure section as long as the amount of the liquid sample flowing downstream from the high inflow-withstanding pressure section is smaller than that of the liquid sample flowing into the branch channel. After the first branch channel and the liquid reservoir are filled with the liquid sample, the liquid sample passes through the high inflow-withstanding pressure section and is led to a branch point between the next branch channel and the main channel. Then, the branch channels and the liquid reservoirs are filled with the liquid sample one after another from the upstream side to the downstream side of the main channel.

The channel configuration of the dispensing device according to the present invention is simpler than that of a conventional complicated channel configuration. Therefore, the dispensing device according to the present invention is capable of dispensing a liquid sample into the plurality of liquid reservoirs while reducing the dead volume of the liquid sample.

Further, the dispensing device according to the present invention may be configured so that a liquid sample can be delivered by a gas, such as air, after the liquid sample is introduced into the main channel in an amount at least equal to the total volume of the branch channels and the liquid reservoirs connected to the main channel. This makes it possible to further reduce the dead volume of a liquid sample. In this case, it is preferred that a liquid sample is introduced into the main channel in an amount slightly larger than the total volume of the branch channels and the liquid reservoirs in order to reliably fill all the branch channels and liquid reservoirs with the liquid sample.

In the dispensing device according to the present invention, the high inflow-withstanding pressure section, as an example, may have a channel inner wall, with at least a part which forms a contact angle of 90° or larger with a liquid sample.

Further, the high inflow-withstanding pressure section may have a cross-sectional circumference shorter than that of the branch channel.

In a case where the contact angle of a liquid sample on the inner wall of a channel is 90° or larger, the liquid sample receives a negative capillary force from the inner wall of the channel when the liquid sample is introduced into the channel. At this time, a pressure induced by the capillary force is represented by the following formula (1).

[Formula 1]

$$\Delta p = \frac{2(w+d)}{wd}(\gamma_{SG} - \gamma_{SL}) = 2\left(\frac{1}{w} + \frac{1}{d}\right)\gamma_{LG}\cos\theta \quad (1)$$

In the above formula (1), $\Delta P$ represents a pressure induced by the capillary force, "w" represents a channel width, "d" represents a channel depth, $\gamma_{SG}$ represents the interfacial tension between the channel inner wall and air, $\gamma_{SL}$ represents the interfacial tension between the channel inner wall and the liquid sample, $\gamma_{LG}$ represents the interfacial tension of the liquid sample, and $\theta$ represents the contact angle of the liquid sample on the channel inner wall.

As can be seen from the above formula (1), when the channel depth "d" is constant, a smaller channel width "w" makes the absolute value of the capillary force that acts on the liquid sample larger, and when the channel width "w" is constant, a smaller channel depth "d" makes the absolute value of the capillary force that acts on the liquid sample larger. That is, when the cross-sectional circumference of the channel is smaller, the absolute value of the capillary force that acts on the liquid sample is larger.

Therefore, when the cross-sectional circumference of the high inflow-withstanding pressure section is made shorter than that of the branch channel, a liquid sample receives a larger negative capillary force from the channel inner wall of the high inflow-withstanding pressure section than from the channel inner wall of the branch channel. This means that the liquid sample is less likely to flow into the high inflow-withstanding pressure section than into the branch channel.

When the connection between the main channel and the high inflow-withstanding pressure section having a shorter cross-sectional circumference than the branch channel has a continuous and flat part in its inner wall, a liquid sample is likely to flow from the main channel into the high inflow-withstanding pressure section due to the continuity of surface energy at the continuous and flat part. On the other hand, when the connection between the main channel and the high inflow-withstanding pressure section has a stepped portion, a liquid sample is likely to come to rest by the stepped portion due to the discontinuity of surface energy. Therefore, in a case where the main channel and the high inflow-withstanding pressure section are substantially rectangular in cross section, the number of continuous and flat inner wall surfaces at the connection between the main channel and the high inflow-withstanding pressure section may be two or less. When the number of continuous and flat inner wall surfaces at the connection between the main channel and the high inflow-withstanding pressure section is two or less, a liquid sample is less likely to flow from the main channel into the high inflow-withstanding pressure section as compared to a case where the number of continuous and flat inner wall surfaces at the connection between the main channel and the high inflow-withstanding pressure section is three. This makes it easy to allow a liquid sample to come to rest by the high inflow-withstanding pressure section with more stability.

Further, the high inflow-withstanding pressure section may be configured so that the contact angle of a liquid sample on its channel inner wall becomes larger than that of the liquid sample on a channel inner wall of the branch channel. As is clear from the above formula (1), when the contact angle $\theta$ of the liquid sample on the channel inner wall is larger, the absolute value of the capillary force is larger.

Therefore, when the contact angle of a liquid sample on the channel inner wall of the high inflow-withstanding pressure section is made larger than that of the liquid sample on the channel inner wall of the branch channel, the liquid sample receives a larger negative capillary force from the channel inner wall of the high inflow-withstanding pressure section than from the channel inner wall of the branch channel. This means that the liquid sample is less likely to flow into the high inflow-withstanding pressure section than into the branch channel.

Further, the branch channel may include a metering channel whose one end is connected to the main channel and which has a predetermined capacity, and an injection channel whose one end is connected to another end of the metering channel and whose other end is connected to the liquid reservoir, wherein the injection channel has a higher inflow-withstanding pressure than the high inflow-withstanding pressure section and does not allow passage of a liquid sample at a liquid sample introduction pressure applied to introduce the liquid sample into the main channel and the metering channel and at a purge pressure applied to purge the liquid sample from the main channel but allows passage of the liquid sample at a pressure higher than the liquid sample introduction pressure and the purge pressure. In this case, the injection channel may have a channel inner wall, at least part of which forms a contact angle of 90° or larger with a liquid sample.

A series of steps in the process of introducing a liquid sample into the liquid reservoirs in the case of this structure will be described.

A liquid sample introduced into the main channel through the sample inlet toward the sample outlet at the liquid sample introduction pressure reaches a branch point between the first metering channel and the main channel. Then, the liquid sample flows into the first metering channel because when the dispensing device is seen from the sample inlet side, the high inflow-withstanding pressure section having a higher inflow-withstanding pressure than the branch channel is provided in the main channel between the first branch point and the next branch point. When the liquid sample flows into the metering channel, a gas contained in the metering channel flows through the injection channel into the liquid reservoir and a gas contained in the liquid reservoir flows toward the air vent port. This makes it possible to prevent the formation of gas bubbles in the liquid reservoir after the metering channel is filled with the liquid sample, thereby making it possible to reliably fill the metering channel with a predetermined volume of the liquid sample. At this time, it is preferred that the liquid sample does not flow downstream from the high inflow-withstanding pressure section. However, the liquid sample may flow downstream from the high inflow-withstanding pressure section as long as the amount of the liquid sample flowing downstream from the high inflow-withstanding pressure section is smaller than that of the liquid sample flowing into the metering channel.

After the first metering channel is filled with the liquid sample, the liquid sample passes through the high inflow-withstanding pressure section and is led to a branch point between the next metering channel and the main channel. At this time, the liquid sample does not flow into the injection channel and the liquid reservoir because the injection channel connected to the metering channel has a higher inflow-withstanding pressure than the high inflow-withstanding pressure section. From the viewpoint of injecting the liquid sample into the liquid reservoir with high accuracy, it is preferred that the liquid sample does not flow into the injection channel and the liquid reservoir at all during introduction of the liquid sample into the liquid sample introduction channel.

Then, after the metering channels are filled with the liquid sample one after another from the upstream side to the downstream side of the main channel, the liquid sample present in the main channel is purged. This purging may be performed after all the metering channels are filled with the liquid sample or at the same time as delivery of the liquid sample by a gas such as air after the liquid sample is introduced into the main channel in an amount at least equal to the total volume of the metering channels connected to the main channel. After the liquid sample is purged, a pressure higher than the purge pressure is applied to the inside of the main channel to inject the liquid sample contained in the metering channels into the liquid reservoirs through the injection channels.

In the case of this structure, a liquid sample does not flow into the liquid reservoirs during introduction of the liquid sample into the sample introduction channel. Therefore, even when the liquid reservoirs previously contain a reagent or the like, the liquid sample and the reagent are not mixed together during introduction of the liquid sample into the sample introduction channel. By configuring the main channel to be hermetically sealable, it is possible to prevent the entry of foreign matter into the main channel, the air vent port, and the liquid reservoirs from the outside. In addition, it is also possible to prevent the leakage of liquid into the outside of the device, thereby preventing environmental contamination, etc.

Further, in the case of this structure, the main channel may be hermetically sealable. Such a hermetically-sealable main channel can be obtained by, for example, allowing the both ends of the main channel to be openable and closable. The phrase "allowing the both ends of the introduction channel or the main channel to be openable and closable" used herein includes a case where each end of the introduction channel or the main channel is connected to another space, and the end of this 'another' space located on the opposite side from the introduction channel or the main channel is openable and closable.

Further, in the case of this structure, the air vent port may be hermetically sealable. Such a hermetically-sealable air vent port can be obtained by, for example, allowing the end of the air vent port located on the opposite side from the liquid reservoir to be openable and closable. The phrase "allowing the end of the air vent port located on the opposite side from the liquid reservoir to be openable and closable" used herein includes a case where the end of the air vent port located on the opposite side from the liquid reservoir is connected to another space, and the end of this 'another' space located on the opposite side from the air vent port is openable and closable.

In the case of the structure having such a hermetically-sealable main channel and air vent port, a liquid is introduced into the main channel and the metering channels. Next, the liquid is purged from the main channel, and further, the liquid remaining in the metering channels is injected into the liquid reservoirs. As a result, both ends of the main channel and the end of the air vent port located on the opposite side from the liquid reservoir are closed to hermetically seal the main channel and the air vent port.

Further, in the case of the structure having the metering channels and the injection channels, a second high inflow-withstanding pressure section, which has an inflow-withstanding pressure equal to or higher than that of the high inflow-withstanding pressure section, may be provided in the main channel between the sample outlet and the high inflow-withstanding pressure section, which is provided between the branch channel and the sample outlet, so as to be spaced from the high inflow-withstanding pressure section. In this case, the second high inflow-withstanding pressure section, as an example, may have a channel inner wall, with at least a part which forms a contact angle of 90° or larger with a liquid sample.

The second high inflow-withstanding pressure section may be configured, for example, to have a shorter cross-sectional circumference than the high inflow-withstanding pressure section.

Alternatively, the second high inflow-withstanding pressure section may be constituted of, for example, a plurality of narrow holes having a shorter cross-sectional circumference than the high inflow-withstanding pressure section.

Alternatively, the second high inflow-withstanding pressure section may be constituted of, for example, a plurality of projections.

A series of steps in the process of introducing a liquid sample into the liquid reservoirs in the case of this structure will be described. The step of filling each of the metering channels with a liquid sample and the step of purging are the same as those described above.

As a result of purging, the front end of the liquid sample present in the main channel passes through the high inflow-withstanding pressure section and then reaches the second high inflow-withstanding pressure section. The liquid sample that has reached the second high inflow-withstanding pressure section is less likely to flow toward the sample outlet because the second high inflow-withstanding pressure section has a higher inflow-withstanding pressure than the main channel. In this state, a gas is fed into the main channel from the sample inlet side, and as a result, the pressure in the main channel is increased and a pressure higher than the purge pressure is applied to the inside of the main channel so that the liquid sample contained in the metering channels is injected into the liquid reservoirs through the injection channels. This makes it possible to inject the liquid sample contained in the metering channels into the liquid reservoirs without hermetically sealing the sample outlet side of the main channel with the use of a switching valve or the like, thereby simplifying the channel configuration of the dispensing device.

Further, in the case of this structure, feeding of a liquid sample, purging, and injection of a liquid sample into the liquid reservoirs can be performed without changing the driving output of a system for feeding liquid or gas such as a syringe pump. This is because by allowing a gas to continue to flow into the main channel by driving the system for feeding liquid or gas at a constant output during purging and injection of a liquid sample into the liquid reservoirs, the front end of the liquid sample remaining in the main channel reaches the second high inflow-withstanding pressure section, and therefore, the pressure in the main channel is increased. This makes it easy to control the system for feeding liquid or gas. However, the driving outputs of the system for feeding liquid or gas during feeding of a liquid sample, purging, and injection of a liquid sample into the liquid reservoirs may be different from each other. For example, the driving output of the system for feeding liquid or gas during injection of a liquid sample into the liquid reservoirs may be made higher than that during feeding of a liquid sample and purging. It is to be noted that it is necessary to control the amount of a liquid sample to be introduced into the main channel through the sample inlet in consideration of the capacity of a part of the main channel between the most downstream injection channel and the second high inflow-withstanding pressure section in order to prevent the liquid sample from being present at a branch point between the main channel and the injection channel after the front end of the purged liquid sample reaches the second high inflow-withstanding pressure section.

Further, a waste liquid container may be provided in the main channel between the high inflow-withstanding pressure section and the second high inflow-withstanding pressure section, wherein the second high inflow-withstanding pressure section is provided at a position which does not allow a liquid sample contained in the waste liquid container to come into contact with the second high inflow-withstanding pressure section. In the case of this structure, a purged liquid sample is contained in the waste liquid container, and therefore the downstream end of the main channel cannot be closed by bringing the liquid sample into contact with the second high inflow-withstanding pressure section. However, since the second high inflow-withstanding pressure section having a higher inflow-withstanding pressure than the high inflow-withstanding pressure section is provided, as compared to a case where the second high inflow-withstanding pressure section is not provided, the pressure in the main channel can be more easily increased to such a degree that a liquid sample contained in the metering channels is injected into the liquid reservoirs through the injection channels by feeding a gas into the main channel after purging by making the driving output of a system for feeding liquid or gas higher than that used for purging. Also in the case of this structure, a liquid sample contained in the metering channels can be injected into the liquid reservoirs without hermetically sealing the sample outlet side of the main channel with the use of a switching valve or the like, thereby simplifying the channel configuration of the dispensing device. Further, the liquid sample is not discharged through the sample outlet but is contained in the waste liquid container, thereby reducing concerns about environmental contamination with the liquid sample. It is to be noted that it is necessary to control the amount of a liquid sample to be introduced into the main channel through the sample inlet in consideration of the capacity of the waste liquid container in order to prevent the liquid sample from being present at a branch point between the main channel and the injection channel when the liquid sample is injected into the liquid reservoirs.

Another aspect of the present invention is directed to a dispensing device including:

a base substrate;

a cover substrate whose one surface is bonded to one surface of the base substrate;

a liquid reservoir constituted of a recess provided in one or both of the one surface of the base substrate and the one surface of the cover substrate;

a liquid sample introduction channel which is constituted of a groove provided in one or both of the one surface of the base substrate and the one surface of the cover substrate and which is connected to the liquid reservoir; and an air vent port which is provided in one or both of the one surface of the base substrate and the one surface of the cover substrate and connected to the liquid reservoir at a position different from a position where the liquid sample introduction channel is connected to the liquid reservoir, wherein the number of the liquid reservoirs is two or more, the liquid sample introduction channel includes a main channel whose one end is connected to a sample inlet and whose other end is connected to a sample outlet and a plurality of branch channels connected to the main channel between the sample inlet and the sample outlet, the branch channels are each connected to the different liquid reservoirs at their ends located on the opposite side from the main channel, a third high inflow-withstanding pressure section is provided in the main channel between the branch channel and the sample outlet, the third high inflow-withstanding pressure section has a higher inflow-withstanding pressure than the branch channel, and the air vent port has a higher inflow-withstanding pressure than the third high inflow-withstanding pressure section. Here, the air vent port may be a channel constituted of a groove or a through hole or may be constituted of pores of, for example, a hydrophobic porous membrane. The third high inflow-withstanding pressure section, as an example, may have a channel inner wall, with at least a part which forms a contact angle of 90° or larger with a liquid sample. The air vent port may have a channel inner wall, at least part of which forms a contact angle of 90° or larger with a liquid sample.

A series of steps in the process of introducing a liquid sample into the liquid reservoirs in the case of this structure will be described.

A liquid sample introduced into the main channel through the sample inlet toward the sample outlet reaches a branch point between the branch channel and the main channel. Here, the branch channel is connected to the air vent port through the liquid reservoir and the third high inflow-withstanding pressure section is provided on the downstream side of the main channel. The liquid sample that has reached the branch point between the main channel and the branch channel flows through the main channel and reaches the third high inflow-withstanding pressure section provided on the downstream side of the main channel because the air vent port has a higher inflow-withstanding pressure than the third high inflow-withstanding pressure section, and therefore, the liquid sample that has reached the branch point between the branch channel and the main channel is more likely to flow downstream through the main channel than to flow into the branch channel. The liquid sample introduced into the main channel flows from the main channel into the plurality of branch channels at the same time after the front end of the liquid sample reaches the third high inflow-withstanding pressure section, and therefore, each of the liquid reservoirs is filled with the liquid sample because the third high inflow-withstanding pressure section has a higher inflow-withstanding pressure than the branch channel. Since the liquid sample flows into the plurality of branch channels at the same time, the flow rate of the liquid sample in each of the branch channels and each of the liquid reservoirs is lower than that of the liquid sample introduced into the main channel through the sample inlet. When the liquid sample flows into the branch channel and the liquid reservoir, a gas contained in the liquid reservoir is discharged through the air vent port. This makes it possible to prevent the formation of gas bubbles in the liquid reservoir after the liquid reservoir is filled with the liquid sample, thereby making it possible to reliably fill the liquid reservoir with a predetermined volume of the liquid sample. At this time, it is preferred that the liquid sample does not flow downstream from the third high inflow-withstanding pressure section. However, the liquid sample may flow downstream from the third high inflow-withstanding pressure section as long as the amount of the liquid sample flowing downstream from the third high inflow-withstanding pressure section is smaller than that of the liquid sample flowing into the branch channel.

After each of the liquid reservoirs is filled with the liquid sample, the liquid sample present in the main channel is purged by a gas. At this time, the liquid sample present in the main channel passes through the third high inflow-withstanding pressure section and flows toward the sample outlet and is purged because the air vent port connected to the liquid reservoir has a higher inflow-withstanding pressure than the third high inflow-withstanding pressure section.

The dispensing device according to this aspect of the invention has a channel configuration simpler than a conventional complicated channel configuration, and is therefore capable of dispensing a liquid sample into the plurality of liquid reservoirs while reducing the dead volume of the liquid sample.

Meanwhile, as described above, since the air vent port connected to each of the liquid reservoirs has a higher inflow-withstanding pressure than the third high inflow-withstanding pressure section, gas as well as liquid is less likely to flow into the air vent port than into the main channel, the branch channel, and the third high inflow-withstanding pressure section. When a liquid sample flows into the liquid reservoir, a gas present in the liquid reservoir is discharged through the air vent port, but the pressure in the liquid reservoir is increased cue to a high inflow-withstanding pressure of the air vent port. When the pressure in the liquid reservoir is increased, the flow of a liquid sample in the liquid reservoir becomes unstable, and therefore, there is a case where the liquid reservoir is filled with the liquid sample with gas bubbles being trapped in the liquid reservoir. Such a defect becomes more pronounced as the flow rate of a liquid sample in the liquid reservoir is increased.

In order to overcome such a defect, as described above, the dispensing device according to this aspect of the invention is configured to be able to make the flow rate of a liquid sample in the branch channel and the liquid reservoir lower than that of the liquid sample introduced into the main channel through the sample inlet. Therefore, for example, in a case where the flow rate of a liquid sample introduced into the main channel through the sample inlet is the same in both the structure of the dispensing device according to this aspect of the invention and a structure in which the liquid sample is introduced into the branch channel at the same flow rate as in the main channel, the former is capable of making the flow rate of the liquid sample in the branch channel and the liquid reservoir lower as compared to the latter. This makes it possible to stabilize the flow of a liquid sample in the liquid reservoir, thereby making it possible to fill the liquid reservoir with the liquid sample without trapping gas bubbles in the liquid reservoir. This effect becomes particularly pronounced when a large number of liquid reservoirs are integrated into the dispensing device. Further, since the dispensing device according to this aspect of the invention is capable of introducing a liquid sample into the plurality of branch channels and liquid reservoirs at the same time, the flow rate of the liquid sample introduced into the main channel through the sample inlet can be increased as long as the flow rate of the liquid sample in the branch channel and the liquid reservoir does not become so high that gas bubbles are formed in the liquid reservoir. This makes it possible to shorten the time required to fill the plurality of liquid reservoirs with a liquid sample as compared to a case where the plurality of liquid reservoirs are filled with a liquid sample one after another.

In the dispensing device according to this aspect of the invention, the third high inflow-withstanding pressure section may have a shorter cross-sectional circumference than the branch channel. When the cross-sectional circumference of the high inflow-withstanding pressure section is made shorter than that of the branch channel, a liquid sample receives a larger negative capillary force from the channel inner wall of the third high inflow-withstanding pressure section than from the channel inner wall of the branch channel. This means that the liquid sample is less likely to flow into the third high inflow-withstanding pressure section than into the branch channel.

In a case where the main channel and the third high inflow-withstanding pressure section, which has a shorter cross-sectional circumference than the branch channel, are substantially rectangular in cross section, the number of continuous and flat inner wall surfaces at the connection between the main channel and the third high inflow-withstanding pressure section may be two or less. When the number of continuous and flat inner wall surfaces at the connection between the main channel and the third high inflow-withstanding pressure section is two or less, a liquid sample is less likely to flow from the main channel into the third high inflow-withstanding pressure section as compared to a case where the number of continuous and flat inner wall surfaces at the connection between the main channel and the third high inflow-withstanding pressure section is three. This makes it easy to allow a liquid sample to come to rest by the third high inflow-withstanding pressure section with more stability.

Further, the third high inflow-withstanding pressure section may be configured so that the contact angle of a liquid sample on its channel inner wall becomes larger than that of the liquid sample on the channel inner wall of the branch channel. When the contact angle of a liquid sample on the channel inner wall of the third high inflow-withstanding pressure section is made larger than that of the liquid sample on the channel inner wall of the branch channel, the liquid sample receives a larger negative capillary force from the channel inner wall of the third high inflow-withstanding pressure section than from the channel inner wall of the branch channel. This means that the liquid sample is less likely to flow into the third high inflow-withstanding pressure section than into the branch channel.

Further, a fourth high inflow-withstanding pressure section may be provided in the main channel in at least one of the spaces between the branch channels, wherein the fourth high inflow-withstanding pressure section has a higher inflow-withstanding pressure than the branch channel and the air vent port has a higher inflow-withstanding pressure than the fourth high inflow-withstanding pressure section. In this case, either the third high inflow-withstanding pressure section or the fourth high inflow-withstanding pressure section has a higher inflow-withstanding pressure than the other.

In the case of this structure, the dead volume of a liquid sample can be reduced to only the inner volume of a part of the main channel located between the most downstream third high inflow-withstanding pressure section and the fourth high inflow-withstanding pressure section, which is closest to the third high inflow-withstanding pressure section and which is located upstream from the third high inflow-withstanding pressure section. Particularly, by providing the fourth high inflow-withstanding pressure section between the two most downstream branch channels, the dead volume of a liquid sample can be minimized.

Further, the branch channel may include a metering channel whose one end is connected to the main channel and which has a predetermined capacity, and an injection channel whose one end is connected to the other end of the metering channel and the other end is connected to the liquid reservoir. In this case, a liquid sample introduced into the main channel through the sample inlet is more likely to flow into the main channel than into the metering channel at a branch point between the main channel and the metering channel. Further, the injection channel has a channel inner wall, which forms a contact angle of 90° or larger with a liquid sample, and a higher inflow-withstanding pressure than the third high inflow-withstanding pressure section. Further, the injection channel does not allow the passage of a liquid sample at a liquid sample introduction pressure applied to introduce the liquid sample into the main channel and the metering channel and at a purge pressure applied to purge the liquid sample from the main channel but allows the passage of the liquid sample at a pressure higher than the liquid sample introduction pressure and the purge pressure.

A series of steps in the process of introducing a liquid sample into the liquid reservoirs in the case of this structure will be described.

A liquid sample introduced into the main channel through the sample inlet toward the sample outlet at the liquid sample introduction pressure reaches a branch point between the metering channel and the main channel. The liquid sample flows through the main channel and reaches the third high inflow-withstanding pressure section provided on the downstream side of the main channel because the liquid sample that has reached the branch point between the main channel and the metering channel is more likely to flow into the main channel than into the metering channel. The liquid sample introduced into the main channel flows from the main channel into the plurality of metering channels at the same time, and therefore, each of the metering channels is filled with the liquid sample because the third high inflow-withstanding pressure section has a higher inflow-withstanding pressure than the metering channel. Since the liquid sample flows into the plurality of metering channels at the same time, the flow rate of the liquid sample in each of the metering channels is lower than that of the liquid sample introduced into the main channel through the sample inlet. When the liquid sample flows into the metering channel, a gas contained in the metering channel flows through the injection channel toward the liquid reservoir and a gas contained in the liquid reservoir flows toward the air vent port. This makes it possible to prevent the formation of gas bubbles in the liquid reservoir after the metering channel is filled with the liquid sample, thereby making it possible to reliably fill the metering channel with a predetermined volume of the liquid sample. At this time, the liquid sample does not flow into the injection channel and the liquid reservoir because the injection channel connected to the metering channel has a higher inflow-withstanding pressure than the third high inflow-withstanding pressure section. From the viewpoint of injecting the liquid sample into the liquid reservoir with high accuracy, it is preferred that the liquid sample does not flow at all into the injection channel and the liquid reservoir during introduction of the liquid sample into the liquid sample introduction channel. Further, it is preferred that the liquid sample does not flow downstream from the third high inflow-withstanding pressure section. However, the liquid sample may flow downstream from the third high inflow-withstanding pressure section as long as the amount of the liquid sample flowing downstream from the third high inflow-withstanding pressure section is smaller than that of the liquid sample flowing into the metering channel.

After each of the metering channels is filled with the liquid sample, the liquid sample present in the main channel is purged by a gas. At this time, the liquid sample present in the main channel passes through the third high inflow-withstanding pressure section and flows toward the sample outlet and is purged because the injection channel connected to the metering channel has a higher inflow-withstanding pressure than the third high inflow-withstanding pressure section. After the liquid sample is purged, a pressure higher than the purge pressure is applied to the inside of the main channel to inject the liquid sample contained in the metering channels into the liquid reservoirs through the injection channels.

In the case of this structure, a liquid sample does not flow into the liquid reservoirs during introduction of the liquid sample into the sample introduction channel. Therefore, even when the liquid reservoirs previously contain a reagent or the like, the liquid sample and the reagent are not mixed together during introduction of the liquid sample into the sample introduction channel. By configuring the main channel to be hermetically sealable, it is possible to prevent the entry of foreign matter into the main channel, the air vent port, and the liquid reservoirs from the outside. In addition, it is also possible to prevent the leakage of liquid into the outside of the device, thereby preventing environmental contamination, etc.

Further, in the case of this structure, the main channel may be hermetically sealable. Such a hermetically-sealable main channel can be obtained by, for example, allowing the both ends of the main channel to be openable and closable. The phrase "allowing the both ends of the introduction channel or the main channel to be openable and closable" used herein includes a case where each end of the introduction channel or the main channel is connected to another space, and the end of this 'another' space located on the opposite side from the introduction channel or the main channel is openable and closable.

Further, in the case of this structure, the air vent port may be hermetically sealable. Such a hermetically-sealable air vent port can be obtained by, for example, allowing the end of the air vent port located on the opposite side from the liquid reservoir to be openable and closable. The phrase "allowing the end of the air vent port located on the opposite side from the liquid reservoir to be openable and closable" used herein includes a case where the end of the air vent port located on the opposite side from the liquid reservoir is connected to another space, and the end of the another space located on the opposite side from the air vent port is openable and closable.

In the case of the structure having such hermetically-sealable main channel and air vent port, a liquid is introduced into the main channel and the metering channels. Next, the liquid is purged from the main channel, and further, the liquid remaining in the metering channels is injected into the liquid reservoirs. As a result, the both ends of the main channel and the end of the air vent port located on the opposite side from the liquid reservoir are closed to hermetically seal the main channel and the air vent port.

Further, in the case of the structure having the metering channels and the injection channels, a fifth high inflow-withstanding pressure section, which has a higher inflow-withstanding pressure than the third high inflow-withstanding pressure section, may be provided in the main channel between the sample outlet and the third high inflow-withstanding pressure section so as to be spaced from the third high inflow-withstanding pressure section.

The fifth high inflow-withstanding pressure section may be configured, for example, to have a shorter cross-sectional circumference than the main channel.

Alternatively, the fifth high inflow-withstanding pressure section may be constituted of, for example, a plurality of narrow holes having a shorter cross-sectional circumference than the third high inflow-withstanding pressure section.

Alternatively, the fifth high inflow-withstanding pressure section may be constituted of, for example, a plurality of projections.

A series of steps in the process of introducing a liquid sample into the liquid reservoirs in the case of this structure will be described. The step of filling each of the metering channels with a liquid sample and the step of purging are the same as those described above.

As a result of purging, the front end of the liquid sample present in the main channel passes through the third high inflow-withstanding pressure section and then reaches the fifth high inflow-withstanding pressure section. The liquid sample that has reached the fifth high inflow-withstanding pressure section is less likely to flow toward the sample outlet because the fifth high inflow-withstanding pressure section has a higher inflow-withstanding pressure than the main channel. In this state, a gas is fed into the main channel from the sample inlet side, and as a result, the pressure in the main channel is increased and a pressure higher than the purge pressure is applied to the inside of the main channel so that the liquid sample contained in the metering channels is injected into the liquid reservoirs through the injection channels. This makes it possible to inject the liquid sample contained in the metering channels into the liquid reservoirs without hermetically sealing the sample outlet side of the main channel with the use of a switching valve or the like, thereby simplifying the channel configuration of the dispensing device.

Further, in the case of this structure, feeding of a liquid sample, purging, and injection of a liquid sample into the liquid reservoirs can be performed without changing the driving output of a system for feeding liquid or gas such as a syringe pump. This is because by allowing a gas to continue to flow into the main channel by driving the system for feeding liquid or gas at a constant output during purging and injection of a liquid sample into the liquid reservoirs, the front end of the liquid sample remaining in the main channel reaches the fifth high inflow-withstanding pressure section, and therefore, the pressure in the main channel is increased. This makes it easy to control the system for feeding liquid or gas. However, the driving outputs of the system for feeding liquid or gas during feeding of a liquid sample, purging, an injection of a liquid sample into the liquid reservoirs may be different from each other. For example, the driving output of the system for feeding liquid or gas during injection of a liquid sample into the liquid reservoirs may be made higher than that during feeding of a liquid sample and purging. It is to be noted that it is necessary to control the amount of a liquid sample to be introduced into the main channel through the sample inlet in consideration of the capacity of a part of the main channel between the most downstream injection channel and the fifth high inflow-withstanding pressure section in order to prevent the liquid sample from being present at a branch point between the main channel and the injection channel after the front end of the purged liquid sample reaches the fifth high inflow-withstanding pressure section.

Further, a waste liquid container may be provided in the main channel between the third high inflow-withstanding pressure section and the fifth high inflow-withstanding pressure section, wherein the fifth high inflow-withstanding pressure section is provided at a position which does not allow a liquid sample contained in the waste liquid container to come into contact with the fifth high inflow-withstanding pressure section. In the case of this structure, a purged liquid sample is contained in the waste liquid container, and therefore, the downstream end of the main channel cannot be closed by bringing the liquid sample into contact with the second high inflow-withstanding pressure section. However, since the fifth high inflow-withstanding pressure section having a higher inflow-withstanding pressure than the third high inflow-withstanding pressure section is provided, as compared to a case where the fifth high inflow-withstanding pressure section is not provided, the pressure in the main channel can be more easily increased to such a degree that a liquid sample contained in the metering channels is injected into the liquid reservoirs through the injection channels by feeding a gas into the main channel after purging by making the driving output of the system for feeding liquid or gas higher than that used for purging. Also in the case of this structure, a liquid sample contained in the metering channels can be injected into the liquid reservoirs without hermetically sealing the sample outlet side of the main channel with the use of a switching valve or the like, thereby simplifying the channel configuration of the dispensing device. Further, the liquid sample is not discharged through the sample outlet but is contained in the waste liquid container, thereby reducing concerns about environmental contamination with the liquid sample. It is to be noted that it is necessary to control the amount of a liquid sample to be introduced into the main channel through the sample inlet in consideration of the capacity of the waste liquid container in order to prevent the liquid sample from being present at a branch point between the main channel and the injection channel when the liquid sample is injected into the liquid reservoirs.

As described above, the dispensing device according to the present invention includes a plurality of liquid reservoirs and a liquid sample introduction channel including a main channel whose one end is connected to a sample inlet and whose other end is connected to a sample outlet and a plurality of branch channels connected to the main channel between the sample inlet and the sample outlet, wherein the plurality of branch channels are each connected to the different liquid reservoirs at their ends located on the opposite side from the main channel. Further, a plurality of high inflow-withstanding pressure sections are provided in the main channel between the branch channels and between the branch channel and the sample outlet, and each of the high inflow-withstanding pressure sections has a channel inner wall, with at least a part which forms a contact angle of 90° or larger with a liquid sample, and a higher inflow-withstanding pressure than the branch channel. Therefore, the dispensing device according to the present invention has a channel configuration simpler than a conventional complicated channel configuration, and is therefore capable of dispensing a liquid sample into the plurality of liquid reservoirs while reducing the dead volume of the liquid sample.

The dispensing device according to another aspect of the present invention includes a plurality of liquid reservoirs, a liquid sample introduction channel including a main channel whose one end is connected to a sample inlet and whose other end is connected to a sample outlet and a plurality of branch channels connected to the main channel between the sample inlet and the sample outlet, and an air vent channel, wherein the plurality of branch channels are each connected to the different liquid reservoirs at their ends located on the opposite side from the main channel, and a liquid sample introduced into the main channel through the sample inlet is more likely to flow into the main channel than into the branch channel at a branch point between the main channel and the branch channel. Further, a third high inflow-withstanding pressure section is provided in the main channel between the branch channel and the sample outlet, and the third high inflow-withstanding pressure section has a channel inner wall, with at least a part which forms a contact angle of 90° or larger with a liquid sample, and a higher inflow-withstanding pressure than the branch channel. Further, the air vent channel has a channel inner wall, with at least a part which forms a contact angle of 90° or larger with a liquid sample, and a higher inflow-withstanding pressure than the third high inflow-withstanding pressure section. Therefore, the dispensing device according to another aspect of the present invention has a channel configuration simpler than a conventional complicated channel configuration, and is therefore capable of dispensing a liquid sample into the plurality of liquid reservoirs while reducing the dead volume of the liquid sample.

BRIEF DESCRIPTION OF THE DRAWINGS

FIG. 44 is a schematic plan view of a conventional dispensing device.

DESCRIPTION OF THE REFERENCE NUMERALS

Figure 1A:
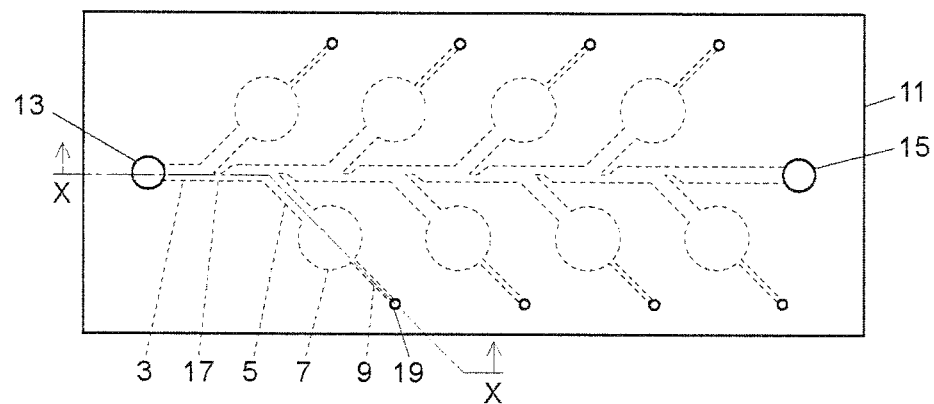
FIG. 1A is a plan view showing the structure of a dispensing device according to one embodiment of the present invention.

1, 103, 201, 301, 401, 501, 601 base substrate
1a, 201a, 301a, 401a, 501a, 601a one surface of base substrate
3, 113, 203, 303, 403, 503, 603 main channel
5, 205, 305, 505 branch channel
7, 105, 207, 307, 407, 507, 607 liquid reservoir
9, 119, 121, 209, 309, 409, 509, 609 air vent channel
11, 111, 211, 311, 411, 511, 611 cover substrate
13, 113a, 213, 313, 413, 513, 613 sample inlet
15, 123a, 215, 315, 415, 515, 615 sample outlet
17, 217, 317, 417 high inflow-withstanding pressure section
19, 219, 319, 419, 519, 619 air outlet
115 metering channel
117 injection channel
423 second high inflow-withstanding pressure section
425 liquid waste container
517, 617 third high inflow-withstanding pressure section
521a, 521b, 627a, 627b fourth high inflow-withstanding pressure section
623 fifth high inflow-withstanding pressure section

DETAILED DESCRIPTION OF THE INVENTION

Hereinbelow, the present invention will be described with reference to the following embodiments.

Embodiment 1

Figure 1B:
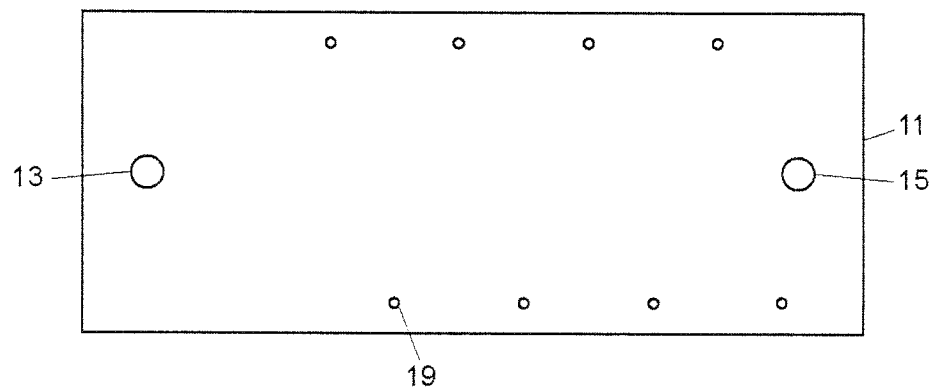
FIG. 1B is a plan view of a cover substrate of the dispensing device according to the embodiment.
Figure 1C:
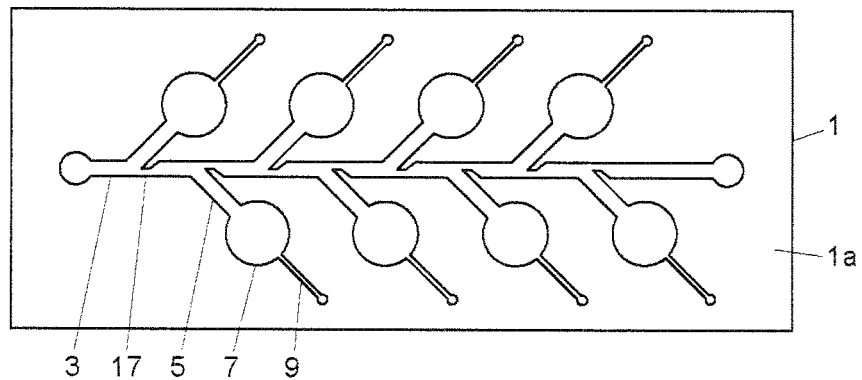
FIG. 1C is a plan view of a base substrate of the dispensing device according to the embodiment.
Figure 1D:
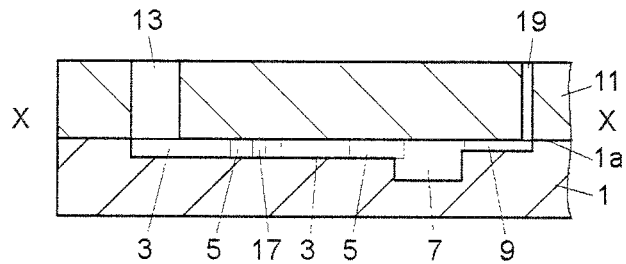
FIG. 1D is a sectional view taken along the X-X line of FIG. 1A.

FIGS. 1A, 1B, 1C, and 1D are drawings showing the structure of a dispensing device according to one embodiment of the present invention, wherein FIG. 1A is a plan view of the dispensing device, FIG. 1B is a plan view of a cover substrate, FIG. 1C is a plan view of a base substrate, and FIG. 1D is a sectional view taken along the X-X line of FIG. 1A.

One surface 1a of a base substrate 1 has a groove for forming a main channel 3 and a plurality of branch channels 5 which constitute a liquid sample introduction channel, recesses for forming a plurality of liquid reservoirs 7, and grooves for forming a plurality of air vent channels (air vent ports) 9. The surface 1a of the base substrate 1 is bonded to a cover substrate 11. The main channel 3, the branch channels 5, the liquid reservoirs 7, and the air vent channels 9 are formed by covering, with the cover substrate 11, the grooves and recesses provided in the surface 1a of the base substrate 1.

The cover substrate 11 has a sample inlet 13 provided at a position corresponding to one end of the main channel 3. The sample inlet 13 is constituted of a through hole. The cover substrate 11 has also a sample outlet 15 provided at a position corresponding to the other end of the main channel 3. The sample outlet 15 is also constituted of a through hole.

The branch channels 5 are connected to the main channel 3 between the sample inlet 13 and the sample outlet 15. The number of the branch channels 5 is the same as that of the liquid reservoirs 7. The branch channels 5 are each connected to the different liquid reservoirs 7 at their ends located on the opposite side from the main channel 3.

In the main channel 3, a plurality of high inflow-withstanding pressure sections 17 are provided between the branch channels 5 and 5 and between the branch channel 5 and the sample outlet 15. The high inflow-withstanding pressure section 17 has a shorter cross-sectional circumference than the branch channel 5, and therefore, has a higher inflow-withstanding pressure than the branch channel 5.

The air vent channel 9 is also connected to the liquid reservoir 7 at a position different from a position where the branch channel 5 is connected to the liquid reservoir 7. The air vent channel 9 has a shorter cross-sectional circumference than the high inflow-withstanding pressure section 17, and therefore, has a higher inflow-withstanding pressure than the high inflow-withstanding pressure section 17. The cover substrate 11 has a plurality of air outlets 19 provided at positions corresponding to the ends of the air vent channels 9 located on the opposite side from the liquid reservoirs 7. The air outlet 19 is constituted of a through hole.

The materials of the base substrate 1 and the cover substrate 11 are not particularly limited, but are preferably cheaply available when the dispensing device is designed to be disposable. Examples of the material of the base substrate 1 include polydimethylsiloxane (PDMS) and silicone rubber. Examples of the material of the cover substrate 11 include resin materials such as polypropylene and polycarbonate.

The design examples of the main channel 3, the branch channel 5, the air vent channel 9, and the high inflow-withstanding pressure section 17 are as follows. The depth of the main channel 3, the branch channel 5, and the high inflow-withstanding pressure section 17 is 500 μm. The width of the main channel 3 and the branch channel 5 is 500 μm. The width of the high inflow-withstanding pressure section 17 is 200 μm. The depth and width of the air vent channel 9 are both 10 μm.

The base substrate 1 can be formed by, for example, molding PDMS using a silicon mold obtained by dry etching.

When the base substrate 1 is formed by molding PDMS ("SYLGARD 184" manufactured by Dow Corning), the contact angle of deionized water as a liquid sample on a channel inner wall is about 108°. When the dispensing device is produced based on the above design examples, a pressure induced by the negative capillary force of the branch channel 5 is about −180 Pa, and a pressure induced by the negative capillary force of the high inflow-withstanding pressure section 17 is about −315 Pa. By making the cross-sectional circumference of the high inflow-withstanding pressure section 17 shorter than that of the branch channel 5, it is possible to make the inflow-withstanding pressure of the high inflow-withstanding pressure section 17 higher than that of the branch channel 5.

FIGS. 2A, 2B, 2C, 2D, and 2E and FIGS. 3A, 3B, 3C, 3D, and 3E are schematic plan views showing how a liquid sample is introduced into the liquid reservoirs 7. In these plan views, a fine dot pattern indicates a liquid sample, a solid arrow indicates the flow of a liquid sample, and an open arrow indicates the flow of air. Hereinbelow, a series of steps in the process of introducing a liquid sample into the liquid reservoirs 7 will be described with reference to FIGS. 2A to 2E and FIGS. 3A to 3E.

Figure 2A:
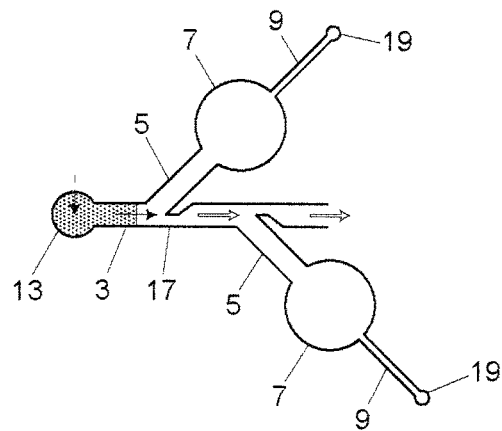
FIG. 2A is a schematic plan view of a sample inlet of the dispensing device according to the embodiment and its vicinity, which shows the first step in the process of introducing a liquid sample into liquid reservoirs.
Figure 2B:
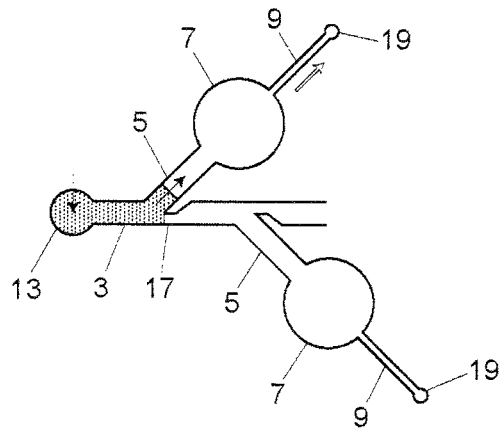
FIG. 2B is a schematic plan view of a sample inlet of the dispensing device according to the embodiment and its vicinity, which shows a step following the step shown in FIG. 2A in the process of introducing a liquid sample into liquid reservoirs.

First, a liquid sample is introduced into the main channel 3 through the sample inlet 13 (see FIG. 2A).

The liquid sample introduced into the main channel 3 reaches a branch point between the first branch channel 5 and the main channel 3. When the dispensing device is seen from the sample inlet 13 side, the high inflow-withstanding pressure section 17 having a higher inflow-withstanding pressure than the branch channel 5 is provided in the main channel 3 between the first branch point and the next branch point. Therefore, the liquid sample flows into the first branch channel 5 and the liquid reservoir 7 (see FIG. 2B). At this time, a gas contained in the liquid reservoir 7 flows through the air vent channel 9 and is then discharged through the air outlet 19. Further, at this time, it is preferred that the liquid sample does not flow downstream from the high inflow-withstanding pressure section 17. However, the liquid sample may flow downstream from the high inflow-withstanding pressure section 17 as long as the amount of the liquid sample flowing downstream from the high inflow-withstanding pressure section 17 is smaller than that of the liquid sample flowing into the branch channel 5.

Figure 2C:
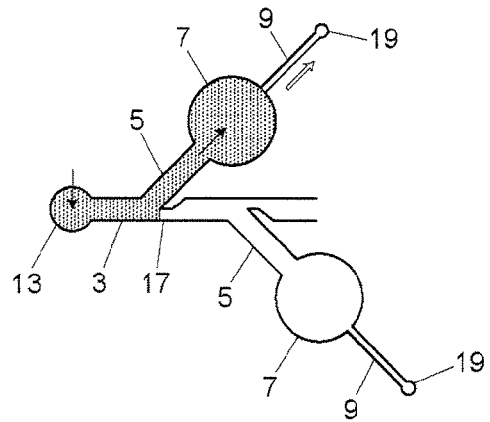
FIG. 2C is a schematic plan view of a sample inlet of the dispensing device according to the embodiment and its vicinity, which shows a step following the step shown in FIG. 2B in the process of introducing a liquid sample into liquid reservoirs.
Figure 2D:
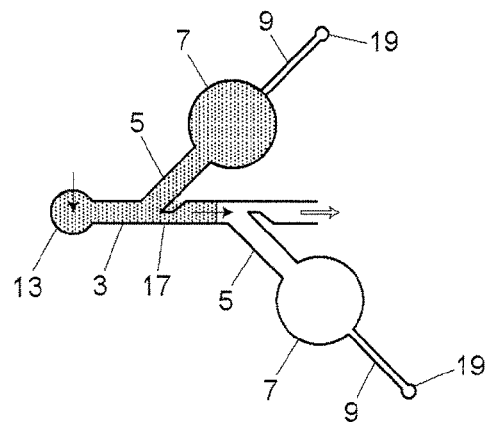
FIG. 2D is a schematic plan view of a sample inlet of the dispensing device according to the embodiment and its vicinity, which shows a step following the step shown in FIG. 2C in the process of introducing a liquid sample into liquid reservoirs.
Figure 3A:
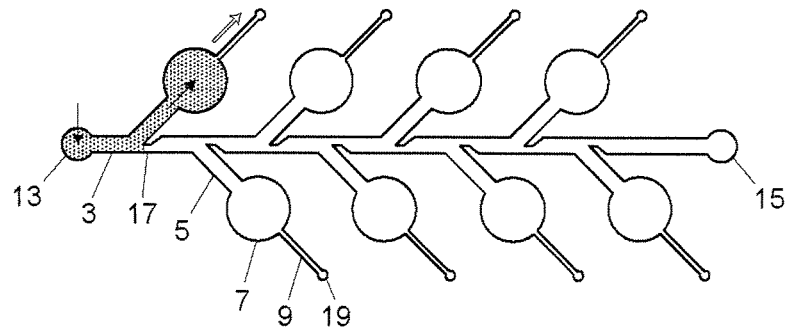
FIG. 3A is a schematic plan view of the entire dispensing device according to the embodiment, which shows the first step in the process of introducing a liquid sample into liquid reservoirs.

In this way, the first branch channel 5 and the liquid reservoir 7 are filled with the liquid sample (see FIG. 2C and FIG. 3A).

After the first branch channel 5 and the liquid reservoir 7 are filled with the liquid sample, the liquid sample passes through the high inflow-withstanding pressure section 17 and is then led to a branch point between the next branch channel 5 and the main channel 3. This is because the high inflow-withstanding pressure section 17 has a lower inflow-withstanding pressure than the air vent channel 9 (see FIG. 2D).

Figure 2E:
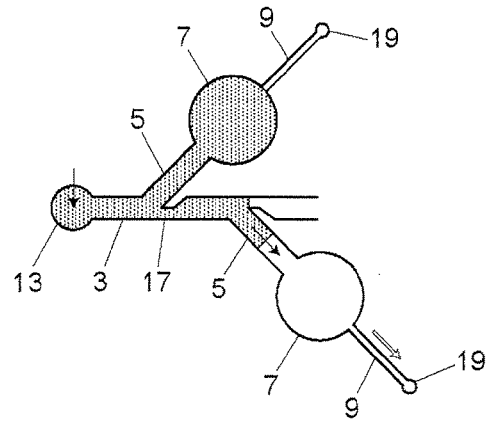
FIG. 2E is a schematic plan view of a sample inlet of the dispensing device according to the embodiment and its vicinity, which shows a step following the step shown in FIG. 2D in the process of introducing a liquid sample into liquid reservoirs.

The liquid sample that has reached the branch point between the next branch channel 5 and the main channel 3 flows into the branch channel 5 and the liquid reservoir 7 (see FIG. 2E).

Figure 3B:
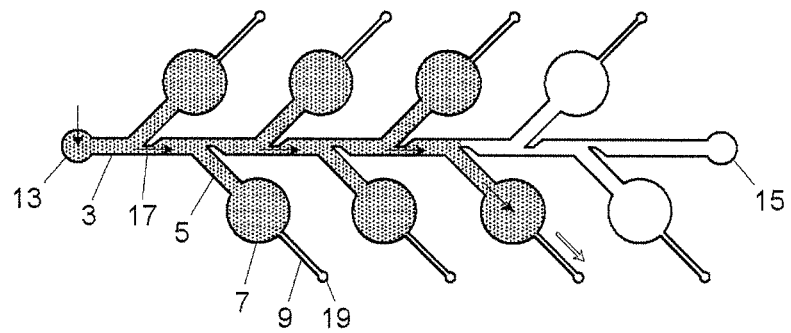
FIG. 3B is a schematic plan view of the entire dispensing device according to the embodiment, which shows a step following the step shown in FIG. 3A in the process of introducing a liquid sample into liquid reservoirs.

After this, the branch channels 5 and the liquid reservoirs 7 are filled with the liquid sample one after another from the upstream side to the downstream side of the main channel 3 (see FIG. 3B).

Figure 3C:
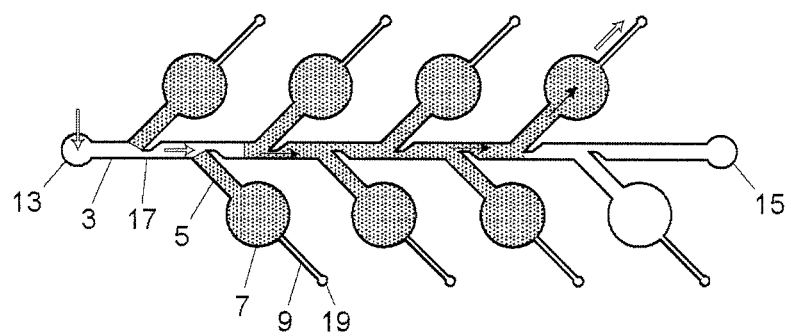
FIG. 3C is a schematic plan view of the entire dispensing device according to the embodiment, which shows a step following the step shown in FIG. 3B in the process of introducing a liquid sample into liquid reservoirs.
Figure 3D:
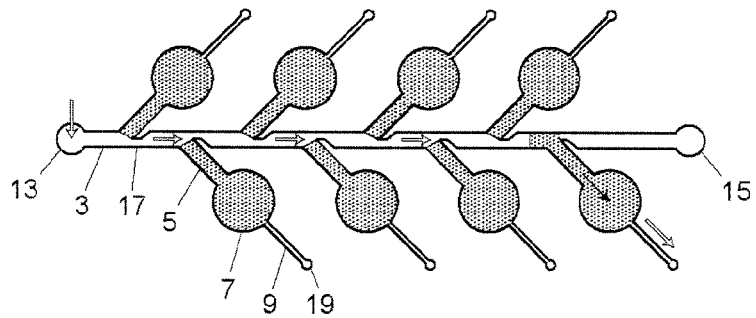
FIG. 3D is a schematic plan view of the entire dispensing device according to the embodiment, which shows a step following the step shown in FIG. 3C in the process of introducing a liquid sample into liquid reservoirs.

After the liquid sample is introduced into the main channel 3 in an amount at least equal to the total volume of all the branch channels 5 and liquid reservoirs 7 (e.g., after the liquid sample is introduced into the main channel 3 in an amount slightly larger than the total volume of all the branch channels 5 and liquid reservoirs 7), air is introduced into the main channel 3 through the sample inlet 13 instead of the liquid sample (see FIG. 3C). The introduction of air into the main channel 3 allows the liquid sample present in the main channel 3 to flow downstream into the branch channels 5 and the liquid reservoirs 7 (see FIG. 3D).

Figure 3E:
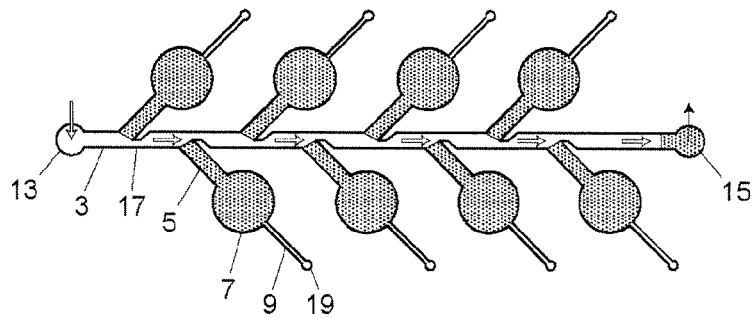
FIG. 3E is a schematic plan view of the entire dispensing device according to the embodiment, which shows a step following the step shown in FIG. 3D in the process of introducing a liquid sample into liquid reservoirs.

After the most downstream branch channel 5 and liquid reservoir 7 connected to the main channel 3 are filled with the liquid sample, the liquid sample remaining in the main channel 3 (dead volume) is discharged through the sample outlet 15 (see FIG. 3E).

As described above, by introducing air instead of a liquid sample into the main channel 3 after the completion of introduction of the liquid sample into the main channel 3, the dead volume of the liquid sample can be reduced. It is to be noted that this dispensing device is capable of reducing the dead volume of a liquid sample as compared to a conventional dispensing device even when air is not introduced into the main channel 3 instead of the liquid sample because the channel configuration of this dispensing device is simpler than a conventional complicated flow configuration.

As described above, the main channel 3, the branch channels 5, the liquid reservoirs 7, and the air vent channels 9 of this embodiment are constituted of grooves and recesses provided in the base substrate 1, but grooves and recesses for forming the main channel, the branch channels, the liquid reservoirs, and the air vent channels may be provided in the cover substrate or in both the base substrate and the cover substrate.

Further, at least part of the inner wall of the high inflow-withstanding pressure section 17 may be subjected to surface treatment to increase the contact angle of a liquid sample. The surface treatment of the inner wall of the high inflow-withstanding pressure section 17 is performed by, for example, dropping a fluorine coating agent onto at least part of the high inflow-withstanding pressure section 17. More specifically, for example, a fluorine coating agent ("NOVEC EGC-1700" manufactured by 3M) is dropped onto the high inflow-withstanding pressure section 17 and is then naturally dried. This makes it possible for the high inflow-withstanding pressure section 17 to have a higher inflow-withstanding pressure.

Embodiment 2

Figure 4A:
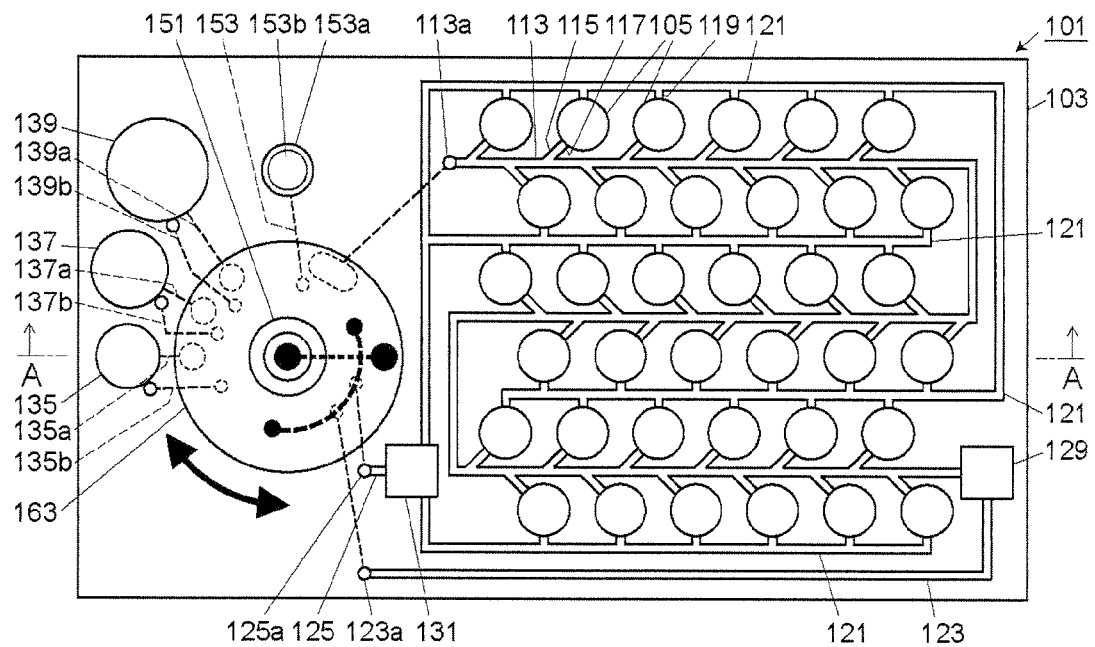
FIG. 4A is a schematic plan view of a dispensing device according to another embodiment of the present invention.
Figure 4B:
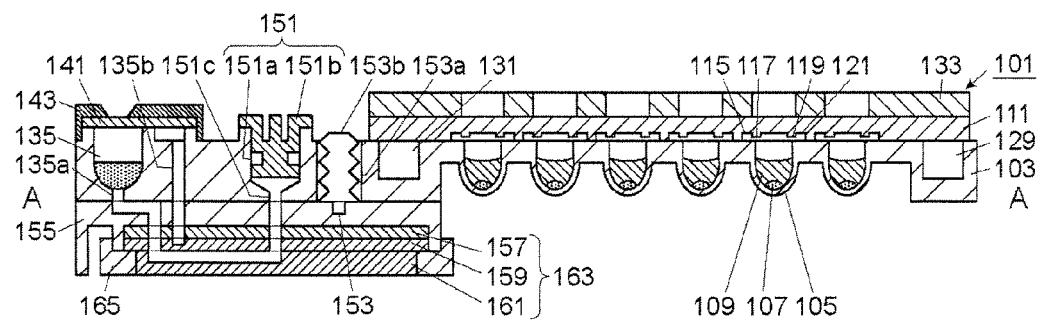
FIG. 4B is a schematic sectional view taken along the A-A line of FIG. 4A, which also includes the sectional views of a bellows, drain spaces, metering channels, injection channels, and sample container air vent channels.
Figure 5:
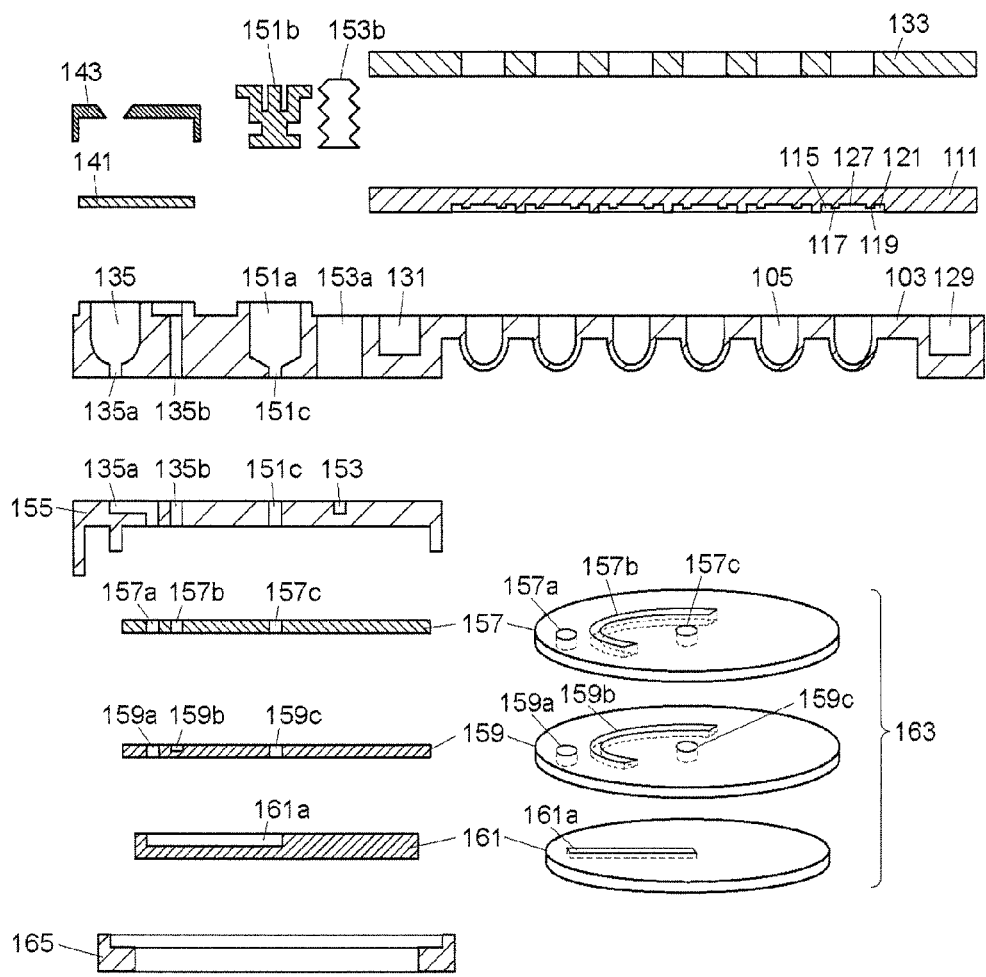
FIG. 5 includes an exploded sectional view of the dispensing device according to the embodiment and an exploded perspective view schematically showing a switching valve.
Figure 6A:
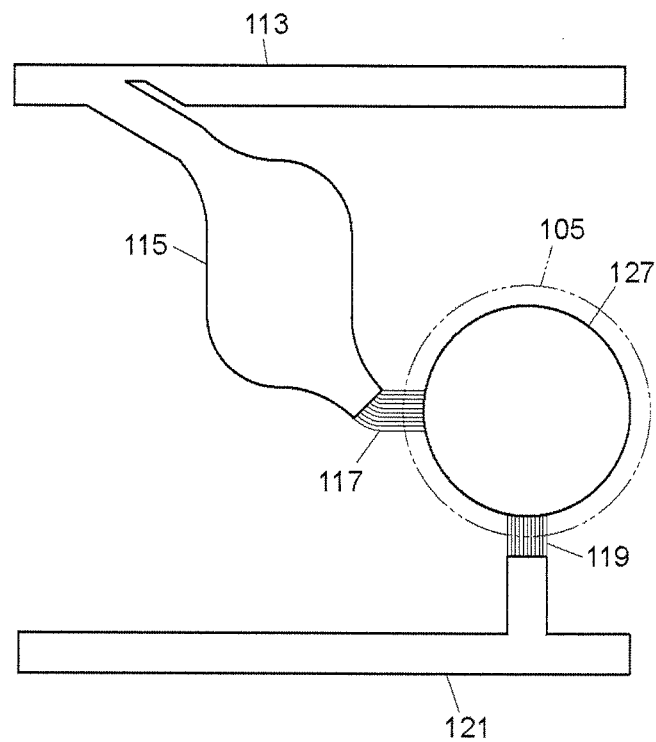
FIG. 6A is a schematic plan view showing one liquid reservoir of the dispensing device according to the embodiment and its vicinity.
Figure 6B:
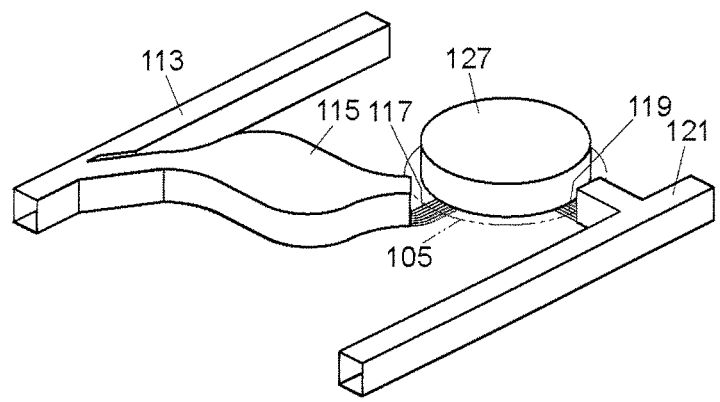
FIG. 6B is a schematic perspective view showing one liquid reservoir of the dispensing device according to the embodiment and its vicinity.
Figure 6C:
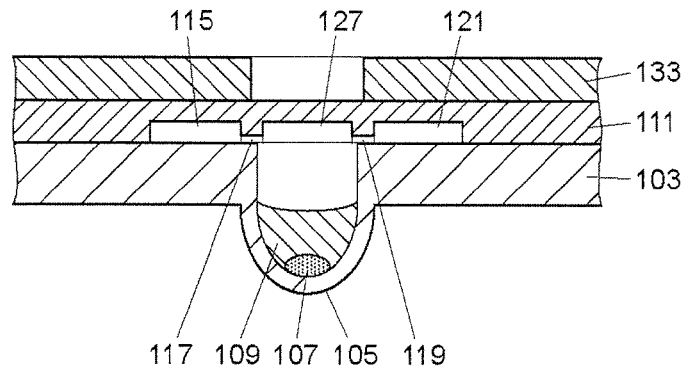
FIG. 6C is a schematic sectional view showing one liquid reservoir of the dispensing device according to the embodiment and its vicinity.
Figure 7A:
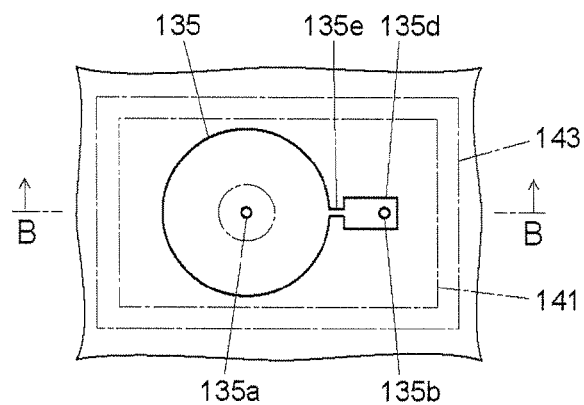
FIG. 7A is an expanded plan view of a sample container of the dispensing device according to the embodiment.
Figure 7B:
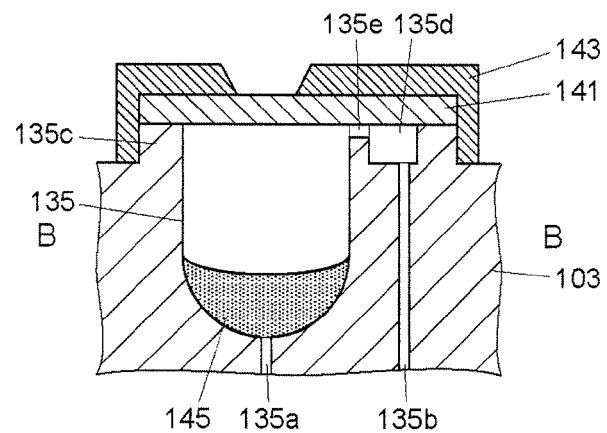
FIG. 7B is a sectional view taken along the B-B line of FIG. 7A.
Figure 8A:
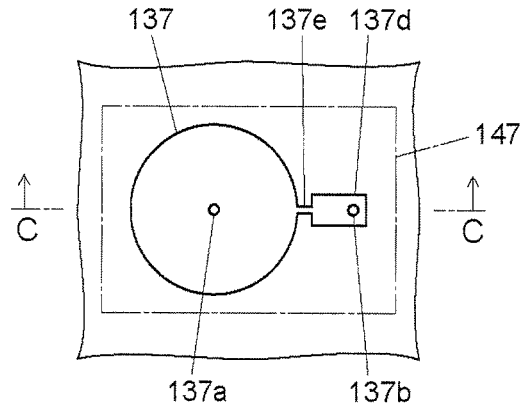
FIG. 8A is an enlarged plan view of a reagent container of the dispensing device according to the embodiment.
Figure 8B:
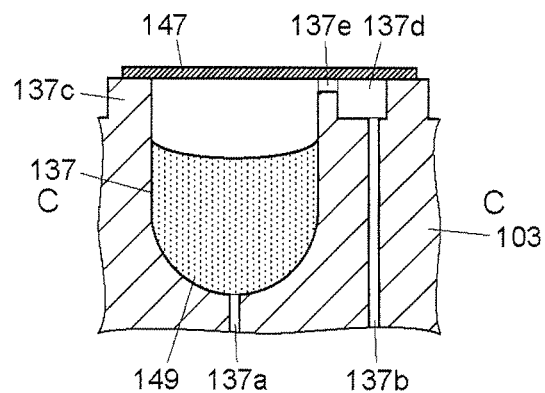
FIG. 8B is a sectional view taken along the B-B line of FIG. 7A.
Figure 9A:
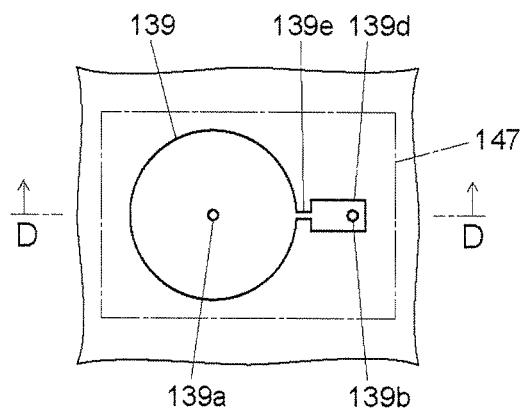
FIG. 9A is an enlarged plan view of a container for air suction of the dispensing device according to the embodiment.
Figure 9B:
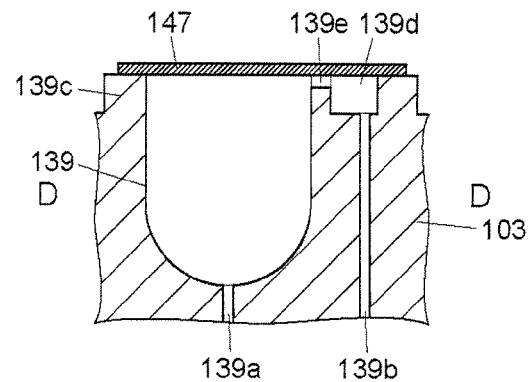
FIG. 9B is a sectional view taken along the B-B line of FIG. 7A.

FIG. 4A is a schematic plan view of a dispensing device according to another embodiment of the present invention, and FIG. 4B is a schematic sectional view taken along the A-A line of FIG. 4A, which also includes the sectional views of metering channels 115, injection channels 117, sample container air vent channels 119 and 121, a liquid drain space 129, an air drain space 131, and a bellows 153b. FIG. 5 includes an exploded sectional view of the dispensing device according to this embodiment and an exploded perspective view schematically showing a switching valve. FIGS. 6A, 6B, and 6C are schematic views showing one liquid reservoir of the dispensing device according to this embodiment and its vicinity, wherein FIG. 6A is a plan view, FIG. 6B is a perspective view, and FIG. 6C is a sectional view. FIGS. 7A and 7B are enlarged views of a sample container, wherein FIG. 7A is a plan view and FIG. 7B is a sectional view taken along the B-B line of FIG. 7A. FIGS. 8A and 8B are enlarged views of a reagent container, wherein FIG. 8A is a plan view and FIG. 8B is a sectional view taken along the C-C line of FIG. 8A. FIGS. 9A and 9B are enlarged views of a container for air suction, wherein FIG. 9A is a plan view and FIG. 9B is a sectional view taken along the D-D line of FIG. 9A.

The dispensing device according to this embodiment of the present invention will be described with reference to these drawings.

A dispensing device 101 includes a plurality of liquid reservoirs 105 each having an opening in one surface of a container base (base substrate) 103. According to this embodiment, the liquid reservoirs 105 are arranged in an array of 6 rows and 6 columns in a staggered format. Each of the liquid reservoirs 105 contains a reagent 107 and a wax 109.

The material of the container base 103 including the liquid reservoirs 105 is not particularly limited, but is preferably cheaply available when the dispensing device 101 is designed to be disposable. Preferred examples of such a material include resin materials such as polypropylene and polycarbonate. Further, when the dispensing device 101 is intended for use in detecting a material contained in the liquid reservoirs 105 by absorbance, fluorescence, chemiluminescence, or bioluminescence, the container base 103 is preferably made of a light-permeable resin so that optical detection can be performed from the bottom of the container base 103. Particularly, when the dispensing device 101 is intended for use in fluorescence detection, the container base 103 is preferably made of a low self-fluorescence (i.e., the amount of fluorescence emitted from a material itself is small) and optically-permeable resin such as polycarbonate. The thickness of the container base 103 is 0.2 to 4.0 mm, preferably 1.0 to 2.0 mm. From the viewpoint of low self-fluorescence required for fluorescence detection, the thickness of the container base 103 is preferably small.

Referring to FIGS. 4A, 4B, 6A, 6B, and 6C, a channel base (cover substrate) 111 is provided on the container base 103 so as to cover a region where the liquid reservoirs 105 are arranged. The channel base 111 is made of, for example, PDMS or silicone rubber. The thickness of the channel base 111 is, for example, 1.0 to 5.0 mm. A surface of the channel base 111 to be bonded to the container base 103 has grooves. The grooves and the surface of the container base 103 together form a main channel 113, metering channels 115, injection channels 117, liquid reservoir air vent channels (air vent ports) 119 and 121, and drain space air vent channels 123 and 125. The surface of the channel base 111 to be bonded to the container base 103 has also recesses 127 to be located above the liquid reservoirs 105. It is to be noted that in FIGS. 4A, 6A, and 6B, the channel base 111 is not shown, and only the grooves and recesses provided in the channel base 111 are shown. The main channel 113, the metering channels 115, and the injection channels 117 constitute a liquid sample introduction channel. Further, the metering channels 115 and the injection channels 117 constitute branch channels.

The main channel 113 is constituted of one channel, and is bent so as to pass by all the liquid reservoirs 105. One end of the main channel 113 is connected to a channel (sample inlet) 113a provided in the container base 103. The channel 113a is constituted of a through hole. The channel 113a is connected to a port of a switching valve 163 (which will be described later). The other end of the main channel 113 is connected to a liquid drain space 129 provided in the container base 103. The main channel 113 is constituted of a groove having a depth of, for example, 400 μm and a width of, for example, 500 μm. It is to be noted that a part of the main channel 113 (hereinafter, also referred to as a "high inflow-withstanding pressure section") having a predetermined length (e.g., 250 μm) and located downstream from a position where the metering channel 115 is connected to the main channel 113 has a width smaller than that of the other part of the main channel 113, and the width of such a part is, for example, 250 μm.

The metering channels 115 branch off the main channel 113. The metering channel 115 is provided for each of the liquid reservoirs 105. One end of the metering channel 115 on the opposite side from the main channel 113 is located in the vicinity of the liquid reservoir 105. The metering channel 115 is constituted of a groove having a depth of, for example, 400 μm. The metering channel 115 has a predetermined internal capacity of, for example, 2.5 μL. A part of the metering channel 115 connected to the main channel 113 has a width of, for example, 500 μm, which is larger than that of the above-described narrow part of the main channel 113. This makes it possible to make the resistance to the flow of a liquid flowing from one end of the main channel 113 higher in the main channel 113 than in the metering channel 115 at a position where the metering channel 115 branches off the main channel 113. Therefore, a liquid flowing from one end of the main channel 113 first flows into the metering channel 115, and after the metering channel 115 is filled with the liquid, the liquid flows downstream through the narrow part of the main channel 113.

The injection channel 117 is also provided for each of the liquid reservoirs 105. One end of the injection channel 117 is connected to the metering channel 115. The other end of the injection channel 117 is connected to the recess 127, which is located above the liquid reservoir 105, so as to be led to the space above the liquid reservoir 105. The injection channel 117 is designed to have a size allowing the liquid tightness of the liquid reservoir 105 to be maintained in a state where there is no difference between the pressure in the liquid reservoir 105 and the pressure in the injection channel 117. According to this embodiment, the injection channel 117 is constituted of a plurality of grooves, each groove has a depth of, for example, 10 μm and a width of, for example, 20 μm, the pitch between adjacent grooves is 20 μm, and 13 grooves are provided in a region having a width of 500 μm. In this case, the area of an interface between the groove constituting the injection channel 117 and the metering channel 115, that is, the cross-sectional area of the groove constituting the injection channel 117 is 200 μm². The recess 127 has a depth of, for example, 400 μm, and has a circular planar shape smaller than that of the liquid reservoir 105.

The liquid reservoir air vent channel 119 is also provided for each of the liquid reservoirs 105. One end of the liquid reservoir air vent channel 119 is connected to the recess 127, which is located above the liquid reservoir 105, at a position different from a position where the injection channel 117 is connected to the recess 127 so as to be located above the liquid reservoir 105. The liquid reservoir air vent channel 119 is designed to have a size allowing the liquid tightness of the liquid reservoir 105 to be maintained in a state where there is no difference between the pressure in the liquid reservoir 105 and the pressure in the liquid reservoir air vent channel 119. The other end of the liquid reservoir air vent channel 119 is connected to the liquid reservoir air vent channel 121. According to this embodiment, the liquid reservoir air vent channel 119 is constituted of a plurality of grooves. Each groove has a depth of, for example, 10 μm and a width of, for example, 20 μm. The pitch between adjacent grooves is 20 μm, and 13 grooves are provided in a region having a width of 500 μm.

The dispensing device according to this embodiment has a plurality of liquid reservoir air vent channels 121. To each of the liquid reservoir air vent channels 121, a plurality of liquid reservoir air vent channels 119 are connected. These liquid reservoir air vent channels 121 are provided to connect the liquid reservoir air vent channels 119 to an air drain space 131 provided in the container base 103. Each of the liquid reservoir air vent channels 121 is constituted of a groove having a depth of, for example, 400 μm and a width of, for example, 500 μm.

The drain space air vent channel 123 is provided to connect the liquid drain space 129 to a port of the switching valve 163 (which will be described later). One end of the drain space air vent channel 123 is located above the liquid drain space 129. The other end of the drain space air vent channel 123 is connected to a channel (sample outlet) 123a provided in the container base 103. The channel 123a is constituted of a through hole. The channel 123a is connected to a port of the switching valve 163 (which will be described later). The drain space air vent channel 123 is constituted of a groove having a depth of, for example, 400 μm and a width of, for example, 500 μm.

The drain space air vent channel 125 is provided to connect the air drain space 131 to a port of the switching valve 163 (which will be described later). One end of the drain space air vent channel 125 is located above the air drain space 131. The other end of the drain space air vent channel 125 is connected to a channel 125a provided in the container base 103. The channel 125a is constituted of a through hole. The channel 125a is connected to a port of the switching valve 163 (which will be described later). The drain space air vent channel 125 is constituted of a groove having a depth of, for example, 400 μm and a width of, for example, 500 μm.

On the channel base 111, a channel cover 133 (not shown in FIG. 4A) is provided. The channel cover 133 is provided to fix the channel base 111 to the container base 103. The channel cover 133 has through holes at positions located above the liquid reservoirs 105.

Referring to FIGS. 4A, 4B, 7A, and 7B, a sample container 135, a reagent container 137, and a container 139 for air suction are provided in the container base 103 at positions other than the positions of a region where the liquid reservoirs 105 are arranged and the drain spaces 129 and 131. The sample container 135, the reagent container 137, and the container 139 for air suction constitute sealed containers of the dispensing device according to the present invention.

In the container base 103, a sample channel 135a and a sample container air vent channel 135b are provided in the vicinity of the sample container 135. The sample channel 135a passes through the container base 103 and extends from the bottom of the sample container 135 to the back surface of the container base 103. The sample container air vent channel 135b passes through the container base 103 and extends from the top surface to the back surface of the container base 103. On the container base 103, a projecting portion 135c is provided so as to surround an opening of the sample container 135. In the projecting portion 135c, a sample container air vent channel 135d constituted of a through hole is provided so as to be located above the sample container air vent channel 135b. In the surface of the projecting portion 135c, a sample container air vent channel 135e which allows the sample container 135 to communicate with the sample container air vent channel 135d is provided.

The sample container air vent channel 135e is constituted of one or more narrow holes, and each narrow hole has a width of, for example, 5 to 200 μm and a depth of 5 to 200 μm. The sample container air vent channel 135e is provided to maintain the liquid tightness of the sample container 135 in a state where there is no difference between the pressure in the sample container 135 and the pressure in the sample container air vent channel 135d. On the projecting portion 135c, a septum 141 which is an elastic member is provided so as to cover the sample container 135 and the air vent channel 135d. The septum 141 is made of an elastic material such as silicone rubber or PDMS. Therefore, a dispensing tool having a sharp tip can pass through the septum 141 to form a through hole, but the through hole can be closed by pulling the dispensing tool out of the septum 141 due to its elasticity. On the septum 141, a septum stopper 143 for fixing the septum 141 is provided. The septum stopper 143 has an opening located above the sample container 135. According to this embodiment, the sample container 135 previously contains a reagent 145.

As shown in FIGS. 8A and 8B, in the container base 103, a reagent channel 137a and a reagent container air vent channel 137b are provided in the vicinity of the reagent container 137. The reagent channel 137a passes through the container base 103 and extends from the bottom of the reagent container 137 to the back surface of the container base 103. The reagent container air vent channel 137b passes through the container base 103 and extends from the top surface to the bottom surface of the container base 103. On the container base 103, a projecting portion 137c is provided so as to surround an opening of the reagent container 137. In the projecting portion 137c, a reagent container air vent channel 137d constituted of a through hole is provided so as to be located above the reagent container air vent channel 137b. In the surface of the projecting portion 137c, a reagent container air vent channel 137e which allows the reagent container 137 to communicate with the reagent container air vent channel 137d is provided.

The reagent container air vent channel 137e is constituted of one or more narrow holes, and each narrow hole has a width of, for example, 5 to 200 μm and a depth of, for example, 5 to 200 μm. The reagent container air vent channel 137e is provided to maintain the liquid tightness of the reagent container 137 in a state where there is no difference between the pressure in the reagent container 137 and the pressure in the reagent container air vent channel 137d. On the projecting portion 137c, a film 147 made of, for example, aluminum is provided so as to cover the reagent container 137 and the air vent channel 137d. The reagent container 137 contains dilution water 149.

As shown in FIGS. 9A and 9B, the container 139 for air suction has the same structure as the reagent container 137. That is, in the container base 103, a channel 139a for air suction and an air vent channel 139b for the container for air suction are provided in the vicinity of the container 139 for air suction. The channel 139a for air suction passes through the container base 103 and extends from the bottom of the container 139 for air suction to the back surface of the container base 103. The air vent channel 139b for the container for air suction passes through the container base 103 and extends from the top surface to the bottom surface of the container base 103. On the container base 103, a projecting portion 139c having air vent channels 139d and 139e for the container for air suction is provided so as to surround an opening of the container 139 for air suction. On the projecting portion 139c, a film 147 made of, for example, aluminum is provided. The container 139 for air suction contains neither a liquid nor a solid, but is filled with air.

Referring to FIGS. 4A, 4B, and 5 again, a syringe 151 is provided in the surface of the container base 103 at a position other than the positions of the drain spaces 129 and 131, the containers 135, 137, and 139 and the region where the liquid reservoirs 105 are arranged. The syringe 151 is constituted of a cylinder 151a provided in the container base 103 and a plunger 151b placed in the cylinder 151a. In the container base 103, a syringe channel 151c is provided. The syringe channel 151c passes through the container base 103 and extends from the bottom of the cylinder 151a to the back surface of the container base 103.

In the container base 103, a bellows 153b is provided at a position other than the positions of the drain spaces 129 and 131, the containers 135, 137, and 139, and the syringe 151 and the region where the liquid reservoirs 105 are arranged. The bellows 153b expands and contracts, and therefore, the internal capacity of the bellows 153b is passively variable. The bellows 153b is placed in, for example, a through hole 153a provided in the container base 103.

A container bottom 155 is attached to the back surface of the container base 103 at a position other than the position of a region where the liquid reservoirs 105 are arranged. In the container bottom 155, an air vent channel 153 is provided at a position allowing the air vent channel 153 to communicate with the bellows 153b. The bellows 153b is connected to the container bottom 155 so as to be in close contact with the surface of the container bottom 155. The container bottom 155 is provided to guide the channels 113a, 123a, 125a, 135a, 135b, 137a, 137b, 139a, 139b, 151c, and 153 to predetermined port positions.

On the surface of the container bottom 155 located on the opposite side from the container base 103, a rotary switching valve 163 is provided. The switching valve 163 is constituted of a disk-shaped sealing plate 157, a rotor upper 159, and a rotor base 161. The switching valve 163 is attached to the container bottom 155 by means of a lock 165.

The sealing plate 157 has a through hole 157a, a through groove 157b, and a through hole 157c. The through hole 157a is provided in the vicinity of the peripheral portion of the sealing plate 157, and is connected to any one of the channels 113a, 135a, 137a, and 139a. The through groove 157b is provided inside the through hole 157a and on a circle concentric with the sealing plate 157, and is connected to at least two of the channels 123a, 125a, 135b, 137b, 139b, and 153. The through hole 157c is provided at the center of the sealing plate 157, and is connected to the syringe channel 151c.

The rotor upper 159 has a through hole 159a, a groove 159b, and a through hole 159c. The through hole 159a is provided at a position corresponding to the through hole 157a of the sealing plate 157. The groove 159b is provided in the surface of the rotor upper 159 so as to correspond to the through groove 157b of the sealing plate 157. The through hole 159c is provided at the center of the rotor upper 159.

The rotor base 161 has a groove 161a. The groove 161a is provided in the surface of the rotor base 161 to connect the through hole 159a provided in the peripheral portion of the rotor upper 159 and the through hole 159c provided at the center of the rotor upper 159 to each other.

By rotating the switching valve 163, the syringe channel 151c is connected to any one of the channels 113a, 135a, 137a, and 139a, and at the same time, the air vent channel 153 is connected to at least any one of the channels 123a, 125a, 135b, 137b, and 139b.

The switching valve 163 shown in FIG. 4A is in its initial state where the syringe channel 151c is not connected to any one of the channels 113a, 135a, 137a, and 139a and the air vent channel 153 is not connected to any one of the channels 123a, 125a, 135b, 137b, and 139b, either.

The injection channel 117 provided in the dispensing device 101 is designed so that the liquid tightness of the liquid reservoir 105 can be maintained in a state where there is no difference between the pressure in the liquid reservoir 105 and the pressure in the injection channel 117. The liquid reservoir air vent channel 119 is also designed so that the liquid tightness of the liquid reservoir 105 can be maintained in a state where there is no difference between the pressure in the liquid reservoir 105 and the pressure in the liquid reservoir air vent channel 119. The main channel 113 constituting a liquid reservoir channel, the liquid drain space 129 connected to the main channel 113, and the drain space air vent channel 123 can be hermetically sealed by switching the switching valve 163. The containers 135, 137, and 139 are sealed with the septum 141 or the film 147. The channels 135a, 135b, 137a, 137b, 139a, and 139b connected to the containers 135, 137, and 139 can be hermetically sealed by switching the switching valve 163. One end of the air vent channel 153 is connected to the bellows 153b, and therefore, the air vent channel 153 is hermetically sealed. As described above, the containers and the channels in the dispensing device 101 constitute a closed system. It is to be noted that even in a case where the dispensing device 101 does not have the bellows 153b and the air vent channel 153 is connected to the atmosphere outside the dispensing device 101, the air vent channel 153 can be cut off from the containers and the channels other than the air vent channel 153 provided in the dispensing device 101 by switching the switching valve 163, and therefore, the containers for containing a liquid and the channels for flowing a liquid can be hermetically sealed.

Figure 10:
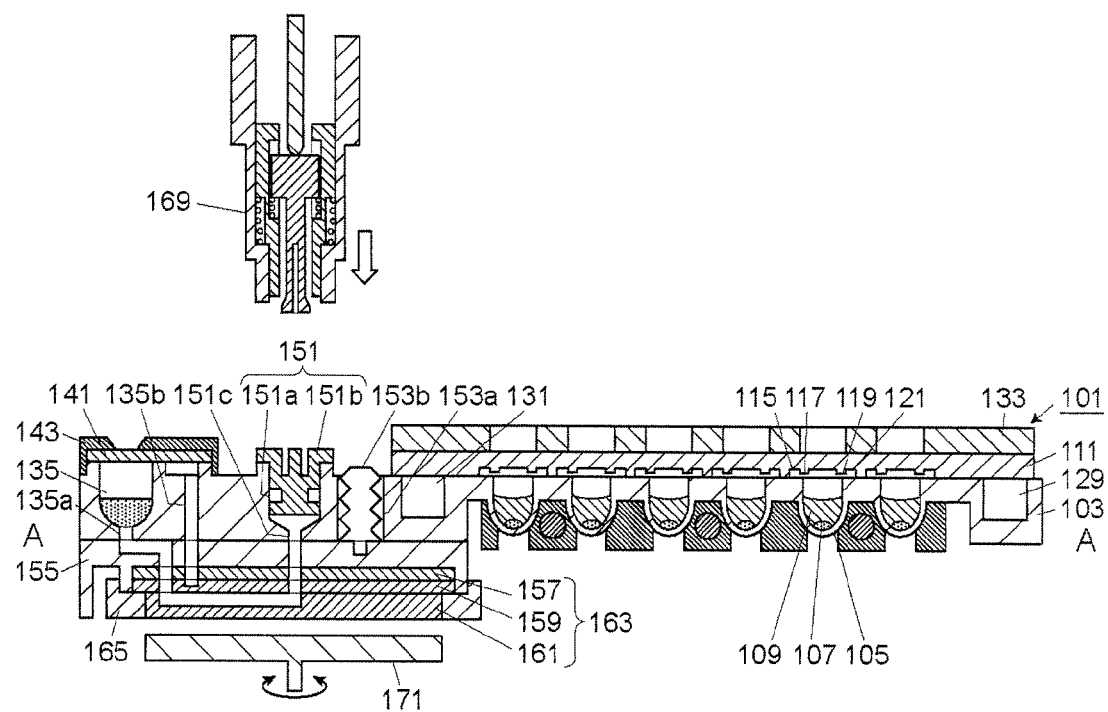
FIG. 10 is a schematic sectional view showing the dispensing device according to the embodiment and a reaction processing apparatus for using the dispensing device.

FIG. 10 is a sectional view showing the dispensing device 101 shown in FIGS. 4A, 4B, and 4C and a reaction processing apparatus for processing the dispensing device 101. The dispensing device 101 shown in FIG. 10 has the same structure as that shown in FIGS. 4A, 4B, and 4C, and therefore, the description thereof is omitted.

The reaction processing apparatus includes a temperature control system 167 for controlling the temperature of the liquid reservoirs 105, a syringe driving unit 169 for driving the syringe 151, and the switching valve driving unit 171 for switching the switching valve 163.

FIGS. 11 to 17 are plan views for explaining the operation of introducing a liquid sample into the liquid reservoirs 105 from the sample container 135. This operation will be described with reference to FIGS. 4A, 4B, and 4C and FIGS. 10 to 17.

A dispensing tool having a sharp tip (not shown) is prepared, and the dispensing tool is passed through the septum 141 provided on the sample container 135 to dispense, for example, 5 μL of a liquid sample into the sample container 135. After the completion of dispensing the liquid sample, the dispensing tool is pulled out of the septum 141. By pulling the dispensing tool out of the septum 141, a through hole formed in the septum 141 is closed due to the elasticity of the septum 141.

The syringe driving unit 169 is connected to the plunger 151b of the syringe 151, and the switching valve driving unit 171 is connected to the switching valve 163.

Figure 11:
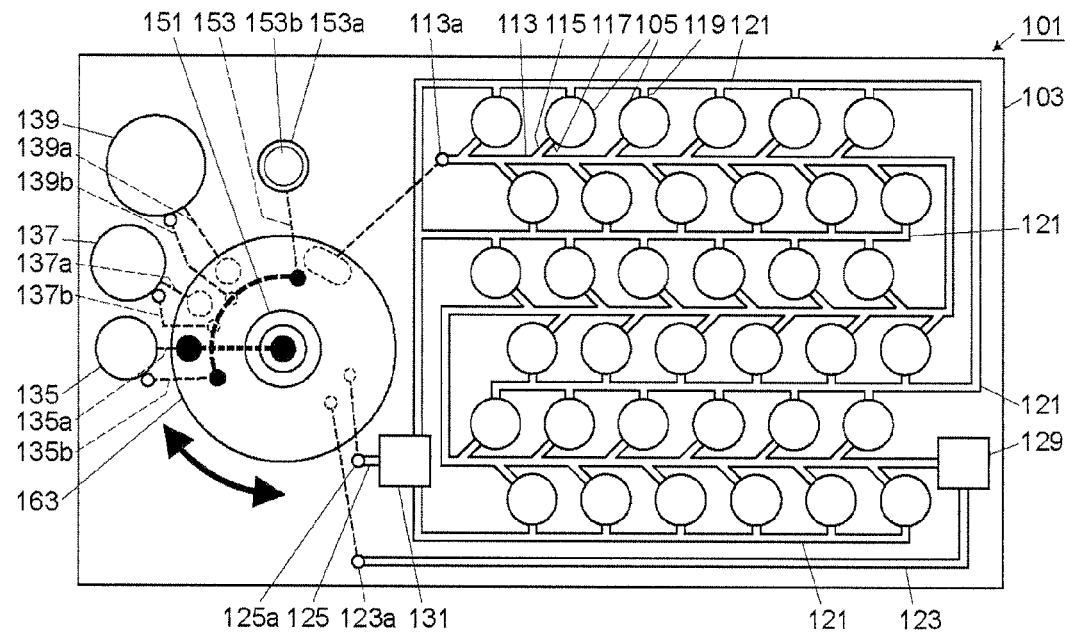
FIG. 11 is a plan view of the dispensing device according to the embodiment for explaining the operation of introducing a liquid sample into liquid reservoirs from the sample container.

As shown in FIG. 11, the switching valve 163 in its initial state shown in FIG. 4A is rotated to connect the sample channel 135a to the syringe channel 151c and to connect the sample container air vent channel 135b to the air vent channel 153. At this time, the air vent channels 137b and 139b are also connected to the air vent channel 153. The sample container 135 contains, for example, 45 μL of the reagent 145.

The syringe 151 is slidably moved to mix the liquid sample and the reagent 145 contained in the sample container 135. Next, for example, only 10 μL of the mixture contained in the sample container 135 is sucked into the channel in the switching valve 163, the syringe channel 151c, and the syringe 151. At this time, the bellows 153b expands and contracts with changes in the volume of a gas contained in the sample container 135 because the sample container 135 is connected to the bellows 153b through the air vent channels 135e, 135d, and 135b, the switching valve 163, and the air vent channel 153.

Figure 12:
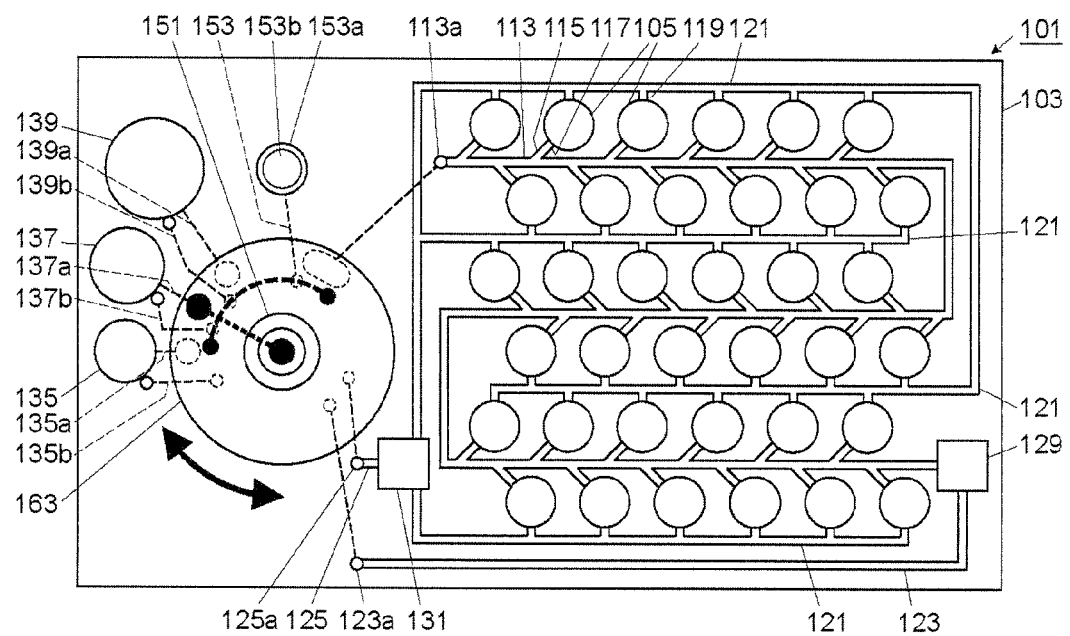
FIG. 12 is a plan view of the dispensing device for explaining operation following the operation explained with reference to FIG. 11.

As shown in FIG. 12, the switching valve 163 is rotated to connect the reagent channel 137a to the syringe channel 151c and to connect the reagent container air channel 137b to the air vent channel 153. The reagent container 137 contains, for example, 190 μL of the dilution water 149. The mixture sucked into the channel in the switching valve 163, the syringe channel 151c, and the syringe 151 is injected into the reagent container 137. The syringe 151 is slidably moved to mix the mixture and the dilution water 149. For example, the whole diluted mixture, that is, 200 μL of the diluted mixture is sucked into the channel in the switching valve 163, the syringe channel 151c, and the syringe 151. At this time, the bellows 153b expands and contracts with changes in the volume of a gas contained in the reagent container 137 because the reagent container 137 is connected to the bellows 153b through the air vent channels 137e, 137d, and 137b, the switching valve 163, and the air vent channel 153.

Figure 13:
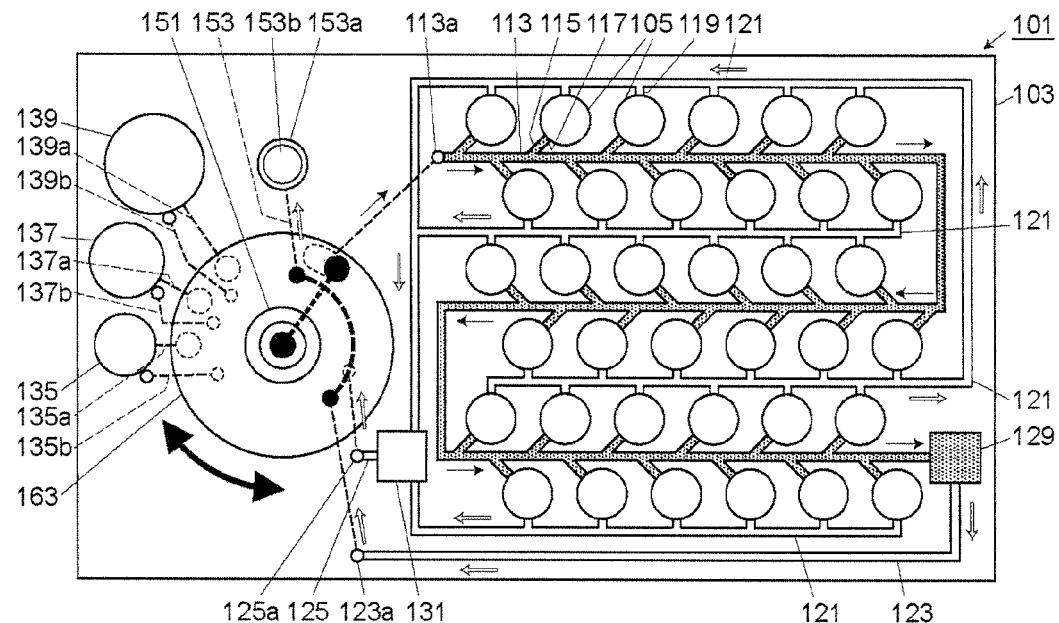
FIG. 13 is a plan view of the dispensing device for explaining operation following the operation explained with reference to FIG. 12.

As shown in FIG. 13, the switching valve 163 is rotated to connect the syringe channel 151c to the channel 113a connected to one end of the main channel 113 and to connect the air vent channel 153 to the channel 123a connected to the liquid drain space 129 and the channel 125a connected to the air drain space 131. The syringe 151 is driven in an extrusion direction to send the diluted mixture sucked into the channel in the switching valve 163, the syringe channel 151c, and the syringe 151 to the main channel 113. As shown by the arrows and dots in FIG. 13, the diluted mixture injected into the main channel 113 through the channel 113a fills the metering channels 115 one after another and reaches the liquid drain space 129. The injection channel 117 allows the passage of a gas but does not allow the passage of the diluted mixture at an introduction pressure applied to introduce the diluted mixture into the main channel 113 and the metering channels 115. When the diluted mixture is introduced into the metering channel 115, a gas contained in the metering channel 115 is transferred into the liquid reservoir 105 through the injection channel 117. Due to the transfer of the gas, part of a gas contained in the liquid reservoir 105 is transferred into the liquid reservoir air vent channels 119 and 121. Further, a gas contained in the channels between the liquid reservoir air vent channel 119 and the bellows 153b is sequentially moved toward the bellows 153b (see open arrows in FIG. 13). Further, due to the injection of the diluted mixture into the liquid drain space 129, a gas contained in the channels between the liquid drain space 129 and the bellows 153b is sequentially moved toward the bellows 153b (see open arrows in FIG. 13). As a result, the bellows 153b expands. According to this embodiment, the diluted mixture (liquid sample) that has reached the liquid drain space 129 is contained in the liquid drain space 129, and is therefore not discharged through the channel 123a constituting a sample outlet.

Figure 14:
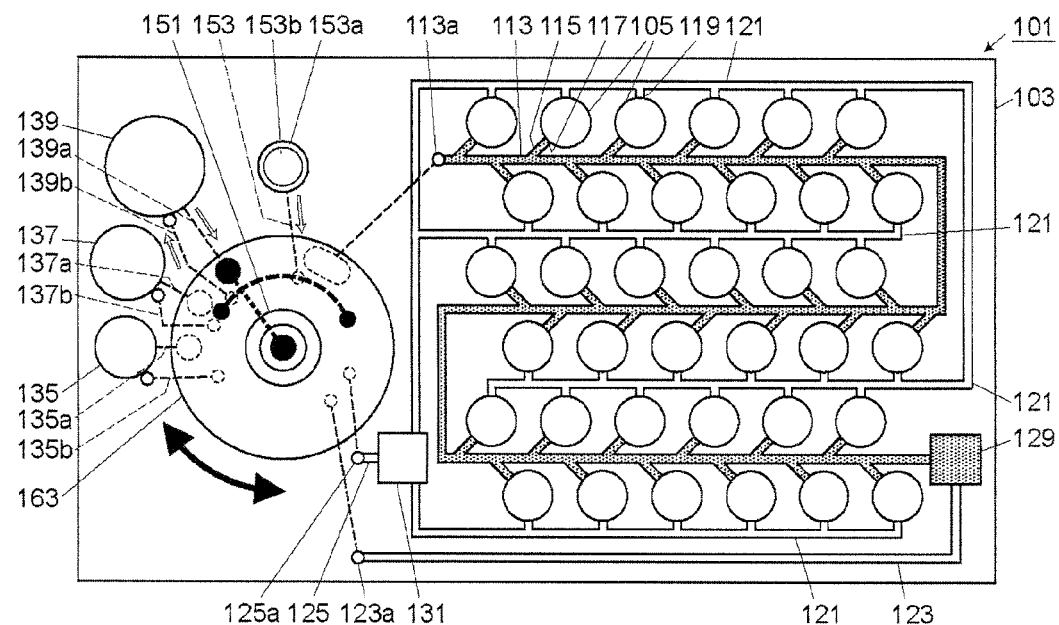
FIG. 14 is a plan view of the dispensing device for explaining operation following the operation explained with reference to FIG. 13.

As shown in FIG. 14, the switching valve 163 is rotated to connect the syringe channel 151c to the channel 139a for air suction and to connect the air vent channel 153 to the air vent channel 139b for the container for air suction. The syringe 151 is driven in a suction direction to suck a gas contained in the container 139 for air suction into the channel in the switching valve 163, the syringe channel 151c, and the syringe 151. At this time, the bellows 153b contracts due to a reduction in the pressure in the container 139 for air suction because the container 139 for air suction is connected to the bellows 153b through the air vent channels 139e, 139d, and 139b, the switching valve 163, and the air vent channel 153 (see open arrows in FIG. 14).

Figure 15:
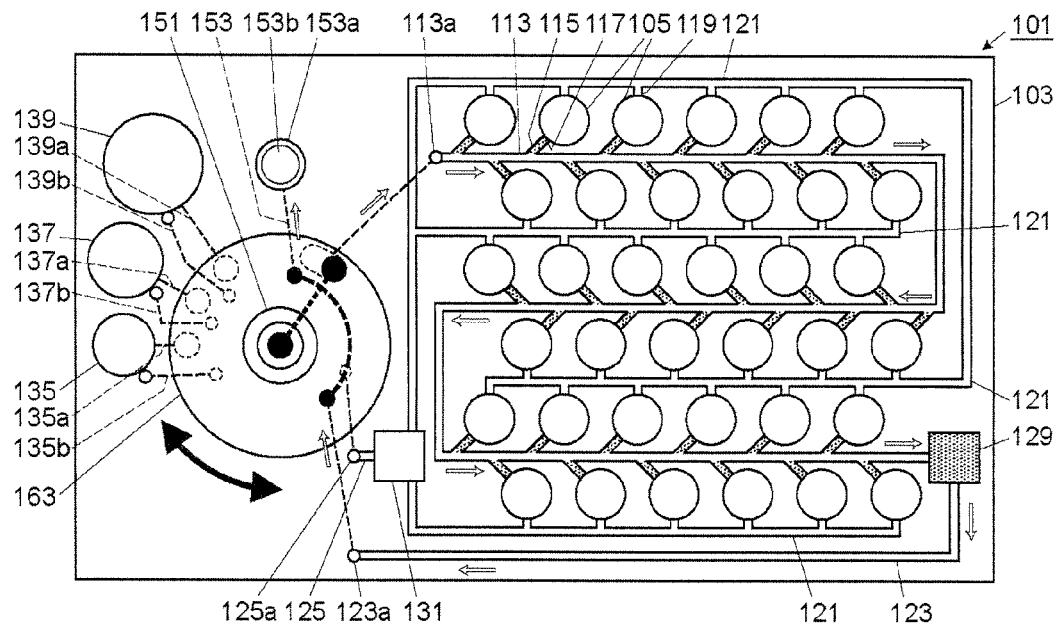
FIG. 15 is a plan view of the dispensing device for explaining operation following the operation explained with reference to FIG. 14.

As shown in FIG. 15, the switching valve 163 is rotated to connect the syringe channel 151c to the channel 113a and to connect the air vent channel 153 to the channels 123a and 125a as in the case of a connection state shown in FIG. 13. The syringe 151 is driven in an extrusion direction to send a gas contained in the channel in the switching valve 163, the syringe channel 151c, and the syringe 151 to the main channel 113 to purge the diluted mixture from the main channel 113 (see open arrows in FIG. 15). At this time, the diluted mixture remains in the metering channels 115 (see dots in FIG. 15) because the injection channels 117 do not allow the passage of the diluted mixture at a purge pressure applied to purge the diluted mixture from the main channel 113. The diluted mixture purged from the main channel 113 is contained in the liquid drain space 129. Due to the injection of the diluted mixture into the liquid drain space 129, a gas contained in the channels between the liquid drain space 129 and the bellows 153b is sequentially moved toward the bellows 153b (see open arrows in FIG. 15). As a result, the bellows 153b expands.

Figure 16:
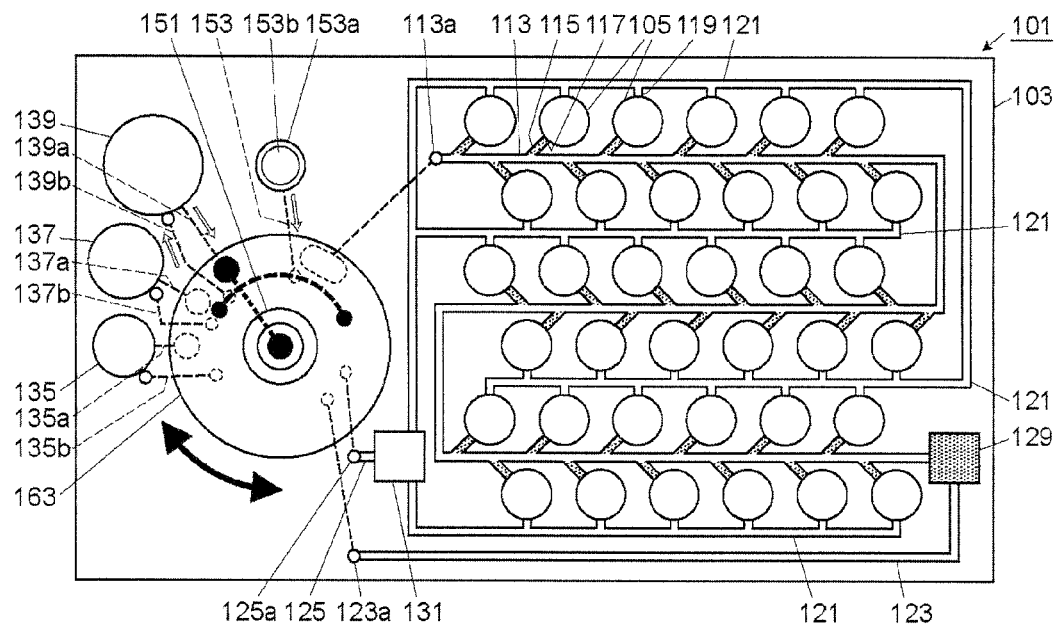
FIG. 16 is a plan view of the dispensing device for explaining operation following the operation explained with reference to FIG. 15.

As shown in FIG. 16, the switching valve 163 is rotated to connect the syringe channel 151c to the channel 139a for air suction and to connect the air vent channel 153 to the air vent channel 139b for the container for air suction as in the case of a connection state shown in FIG. 14. The syringe 151 is driven in a suction direction to suck a gas contained in the container 139 for air suction into the channel in the switching valve 163, the syringe channel 151c, and the syringe 151. At this time, as in the case described with reference to FIG. 14, the bellows 153b contracts (see open arrows in FIG. 16).

Figure 17:
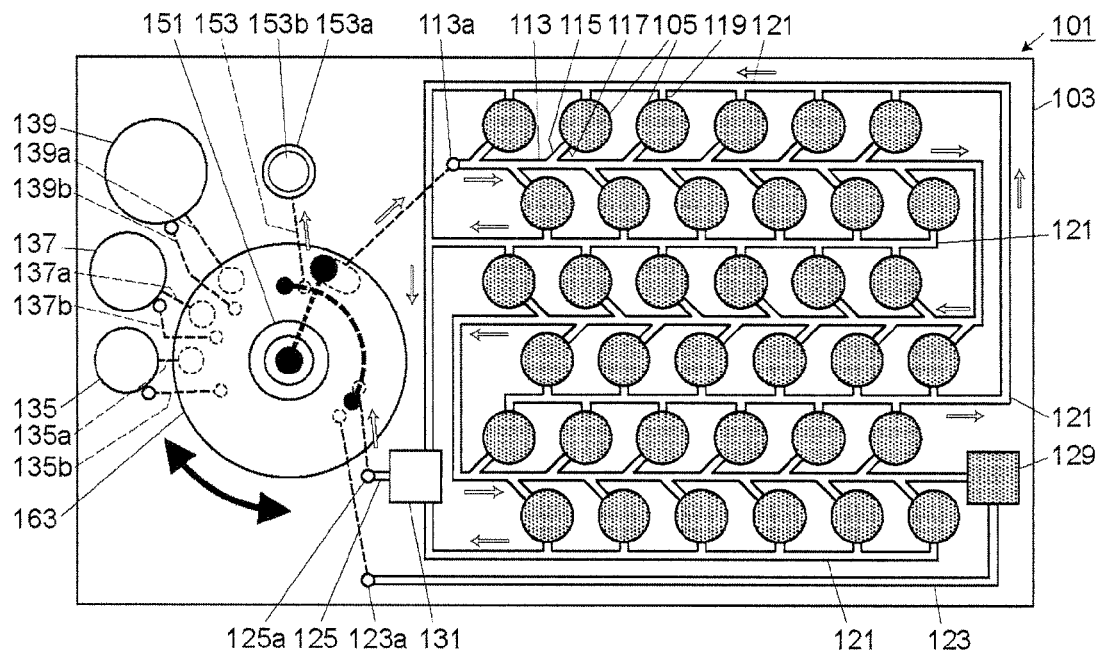
FIG. 17 is a plan view of the dispensing device for explaining operation following the operation explained with reference to FIG. 16.

As shown in FIG. 17, the switching valve 163 is rotated to connect the syringe channel 151c to the channel 113a and to connect the air vent channel 153 to the channel 125a. This connection state is different from those shown in FIGS. 13 and 15 in that the liquid drain space 129, to which the downstream end of the main channel 113 is connected, is not connected to the channel in the switching valve 163. The syringe 151 is driven in an extrusion direction. Since the downstream end of the main channel 113 is not connected to the bellows 153b, a pressure larger than the liquid introduction pressure and the purge pressure is applied to the inside of the main channel 113. As a result, the diluted mixture contained in the metering channels 115 is injected into the liquid reservoirs 105 through the injection channels 117. After the completion of the injection of the diluted mixture into the liquid reservoirs 105, part of a gas contained in the main channel 113 flows into the liquid reservoirs 105 through the metering channels 115 and the injection channels 117. At this time, since the liquid reservoirs 105 are connected to the bellows 153b through the liquid reservoir air vent channels 119 and 121, the air drain space 131, the drain space air vent channel 125a, and the air vent channel 153, a gas contained in the channels between the liquid reservoirs 105 and the bellows 153b is sequentially moved toward the bellows 153b (see open arrows in FIG. 17). As a result, the bellows 153b expands.

The switching valve 163 is returned to its initial state shown in FIG. 4 to hermetically seal the containers, channels, and drain spaces provided in the dispensing device 101. Then, the liquid reservoirs 105 are heated by the temperature control system 167 to melt the wax 109. As a result, the diluted mixture injected into each of the liquid reservoirs 105 sinks below the wax 109, and is therefore mixed with and reacted with the reagent 107. As described above, the use of the dispensing device 101 makes it possible to perform reaction processing in a closed system.

Alternatively, the wax 109 may be melted before the injection of the diluted mixture into the liquid reservoirs 105 by heating the liquid reservoirs 105 by the temperature control system 167 so that the diluted mixture is injected into the liquid reservoirs 105 containing the melted wax 109. In this case, the diluted mixture injected into each of the liquid reservoirs 105 immediately sinks below the wax 109 and is mixed with and reacted with the reagent 107. Even when the switching valve 163 is in the connection state shown in FIG. 17, the hermeticity of the dispensing device 101 is maintained by the bellows 153b. By returning the switching valve 163 to its initial state shown in FIG. 4 after the injection of the diluted mixture into the liquid reservoirs 105, it is possible to hermetically seal the containers, channels, and drain spaces provided in the dispensing device 101. It is to be noted that the switching valve 163 may be returned to its initial state shown in FIG. 4 at any timing during the period from just after the injection of the diluted mixture into the liquid reservoirs 105 until the end of the reaction between the diluted mixture and the reagent 107, or may be returned to its initial state shown in FIG. 4 after the completion of the reaction between the diluted mixture and the reagent 107.

As described above, the use of the dispensing device 101 makes it possible to perform reaction processing in a closed system. In addition, it is also possible to maintain the hermeticity of the dispensing device 101 before and after reaction processing.

According to this embodiment, grooves for forming the channels 117115, 117, 119, 121, and 123 are provided in the channel base 111, but the present invention is not limited thereto. For example, grooves for forming all or part of these channels may be provided in the surface of the container base 103 or may be provided in both the container base 103 and the channel base 111.

Figure 18:
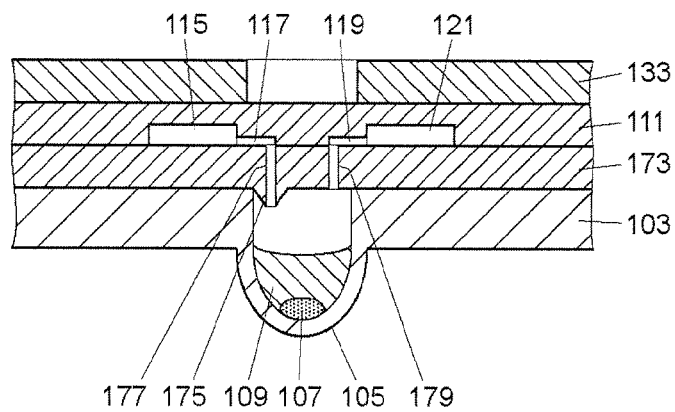
FIG. 18 is an expanded sectional view schematically showing a liquid reservoir of a dispensing device according to another embodiment of the present invention and its vicinity.

FIG. 18 is an expanded sectional view schematically showing a liquid reservoir of a dispensing device according to another embodiment of the present invention and its vicinity. This embodiment has the same structure as the embodiment described above with reference to FIGS. 4A to 17 except that a channel spacer is provided between the liquid reservoir base and the channel base.

A channel spacer 173 is provided on the container base 103 so as to cover a region where the liquid reservoirs 105 are arranged. On the channel spacer 173, the channel base 111 and the channel cover 133 are further provided in this order. The channel spacer 173 is made of, for example, PDMS or silicone rubber. The thickness of the channel spacer 173 is, for example, 0.5 to 5.0 mm. The channel spacer 173 has a projecting portion 175 projecting into each of the liquid reservoirs 105. The projecting portion 175 is substantially trapezoidal in cross section. For example, the proximal end of the projecting portion 175 has a width of 1.0 to 2.8 mm and the distal end of the projecting portion 175 has a width of 0.2 to 0.5 mm. That is, the distal end of the projecting portion 175 is narrower than the proximal end of the projecting portion 175. Further, the projecting portion 175 has a super-water-repellent surface. However, the surface of the projecting portion 175 does not always need to be subjected to water-repellent treatment.

Further, the channel spacer 173 has an injection channel 177 at a position corresponding to each of the projecting portions 175. The injection channel 177 is constituted of a through hole extending from the distal end of the projecting portion 175 to the surface of the channel spacer 173 where the projecting portions 175 are not provided. The injection channel 177 has an inner diameter of, for example, 500 μm. The opening of the injection channel 177 provided on the channel base 111 side is connected to the injection channel 117 provided in the channel base 111. It is to be noted that this embodiment is different from the embodiment described above with reference to FIGS. 4 to 17 in that the channel base 111 does not have the recess 127.

Further, the channel spacer 173 has also a liquid reservoir air vent channel 179 constituted of a through hole. The liquid reservoir air vent channel 179 is provided to allow the liquid reservoir 105 to communicate with the liquid reservoir air vent channel 119 provided in the channel base 111.

Although not shown in FIG. 18, the channel spacer 173 has through holes at positions corresponding to both ends of the main channel 113, one end of each of the liquid reservoir air vent channels 121 located on the air drain space 131 side, and both ends of each of the drain space air vent channels 123 and 125 to connect these channels 113, 121, 123, and 125 to the containers 129 and 131 provided in the container base 103 and the channels 123a and 125b.

According to this embodiment, the end of the injection channel 117 on the opposite side from the injection channel 115 (i.e., the other end of the injection channel) is located at the tip of the projecting portion 175 which projects from the top inner surface of the liquid reservoir 105, and therefore, a liquid is easily dropped into the liquid reservoir 105 through the injection channels 115 one 177 when injected into the liquid reservoir 105.

Further, by placing the tip of the projecting portion 175 in the vicinity of the side wall of the liquid reservoir 105 so that when a liquid passes through the injection channel 117 and is then discharged from the tip of the projecting portion 175, a droplet of the liquid formed at the tip of the projecting portion 175 can come into contact with the side wall of the liquid reservoir 105, it is possible to inject the liquid into the liquid reservoir 105 along the side wall of the liquid reservoir 105, thereby making it possible to more reliably inject the liquid into the liquid reservoir 105. However, the projecting portion 175 may be formed at a position which does not allow a droplet formed at the tip of the projecting portion 175 to come into contact with the side wall of the liquid reservoir 105.

Figure 19:
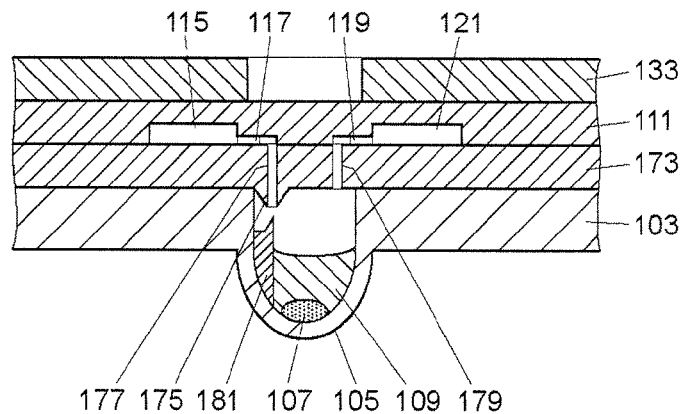
FIG. 19 is an expanded sectional view schematically showing a liquid reservoir of a dispensing device according to another embodiment of the present invention and its vicinity.

FIG. 19 is an expanded sectional view schematically showing a liquid reservoir of a dispensing device according to another embodiment of the present invention and its vicinity.

This embodiment is different from the embodiment described above with reference to FIG. 18 in that a projecting portion 181 is further provided in the liquid reservoir 105. The tip of the projecting portion 181 is located under the tip of the projecting portion 175. This makes it easy to guide a droplet formed at the tip of the projecting portion 175 into the liquid reservoir 105. The projecting portion 181 becomes particularly effective by subjecting the surface of at least the tip of the projecting portion 181 to hydrophilic treatment.

Figure 20:
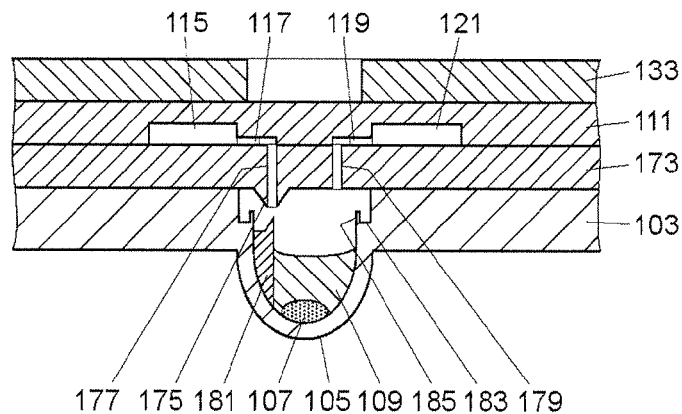
FIG. 20 is an expanded sectional view schematically showing a liquid reservoir of a dispensing device according to another embodiment of the present invention and its vicinity.

FIG. 20 is an expanded sectional view schematically showing a liquid reservoir of a dispensing device according to another embodiment of the present invention and its vicinity.

This embodiment is different from the embodiment described above with reference to FIG. 19 in that a stepped portion 183 and a linear projecting portion 185 are further provided. The stepped portion 183 is provided in the side wall of the liquid reservoir 105. The linear projecting portion 185 is provided on the top surface of the stepped portion 183 in such a manner that a space is left between the tip of the linear projecting portion 185 and the top surface of the liquid reservoir 105. The stepped portion 183 and the linear projecting portion 185 are circular when viewed from above. Further, the linear projecting portion 185 is provided in such a manner that a space is left between the tip of the linear projecting portion 185 and the side wall of the liquid reservoir 105.

By providing the linear projecting portion 185 in such a manner that a space is left between the tip of the linear projecting portion 185 and the top surface of the liquid reservoir 105 and between the tip of the linear projecting portion 185 and the side wall of the liquid reservoir 105, it is possible to prevent a liquid contained in the liquid reservoir 105 from reaching the top surface of the liquid reservoir 105 through the side wall of the liquid reservoir 105. The linear projecting portion 185 becomes particularly effective by subjecting the surface of at least the tip of the linear projecting portion 185 to water-repellent treatment.

The stepped portion 183 and the linear projecting portion 185 shown in FIG. 20 may be applied to the embodiment shown in FIG. 18.

In the case of each of the embodiments described above with reference to FIGS. 18, 19, and 20, grooves for forming the channels 117115, 117, 119, 121, and 123 are provided in the channel base 111, but the present invention is not limited thereto. For example, grooves for forming all or part of these channels may be provided in any one of the surface of the channel spacer 173 located on the channel base 111 side, the surface of the channel spacer 173 located on the container base 111 side, and the surface of the container base 103.

Although the present invention has been described above with reference to the embodiments shown in FIGS. 4A to 20, the shape, material, position, and number of each component are merely examples, and various changes may be made without departing from the scope of the present invention defined in claims.

For example, the bellows 153b connected to the air vent channel 153 may have another structure as long as it is a capacity-variable member whose internal capacity is passively variable. Examples of such a bellow having another structure include a bag-shaped one made of a flexible material and a syringe-shaped one.

The dispensing device according to the present invention does not always need to have a capacity-variable member such as the bellows 153b.

In a case where a liquid such as a reagent is not previously contained in the container 135, 137, or 139, the air vent channel thereof does not always need to partially have the channel 135e, 137e, or 139e constituted of a narrow hole.

In the above embodiments, the air vent channels 135b, 137b, and 139b, which communicate with the containers 135, 137, and 139 provided as sealed containers constituting the dispensing device according to the present invention, are connected to the air vent channel 153 through the switching valve 163, but the air vent channels which communicate with the sealed containers may be directly connected to the outside of the dispensing device or a capacity-variable member such as the bellows 153b.

The containers 135, 137, and 139 may be sealed by using an openable and closable cap.

In the above embodiments, the container base 103 is constituted of one component, but the container base may be constituted of two or more components.

The reagent contained in the liquid reservoirs 105 may be a dry reagent.

The sample container 135 and the liquid reservoirs 105 do not always need to previously contain a reagent.

The container base 103 may further have a gene amplification container for performing gene amplification reaction. For example, the reagent container 137 may be used as a gene amplification container when it is empty.

By previously placing a reagent for performing gene amplification reaction in the liquid reservoirs 105, it is possible to perform gene amplification reaction in the liquid reservoirs 105.

In a case where a liquid to be introduced into the main channel 113 contains a gene, a probe which reacts with the gene may be previously placed in the liquid reservoirs 105.

The dispensing device according to the present invention does not always need to have the syringe 151, and a syringe external to the dispensing device may be used to discharge and suck a liquid or a gas.

In the above embodiments, the rotary switching valve 163 is used as a switching valve. However, a switching valve for use in the dispensing device according to the present invention is not limited thereto, and any channel switching valve can be used. The dispensing device according to the present invention may have two or more switching valves.

In the above embodiments, the reagent container 137 contains the dilution water 149, but may contain a reagent instead of the dilution water 149.

Further, in the above embodiments, the syringe 151 is provided on the switching valve 163. However, the position of the syringe 151 is not limited to a position on the switching valve 163, and the syringe 151 may be placed at any position.

In the above embodiments, a liquid filling the metering channels 115 is injected into the liquid reservoirs 105 through the injection channels 117 by applying pressure to the inside of the main channel 113 after air purge, but a reaction processing method used in the present invention is not limited thereto. For example, a liquid filling the metering channels 115 may be injected into the liquid reservoirs 105 through the injection channels 117 by changing the channel configuration of the dispensing device so that negative pressure can be created in the liquid reservoir air vent channel 121 by using the syringe 151, and thereby creating a negative pressure in the liquid reservoir air vent channel 121, and then in the liquid reservoirs 105. Alternatively, another syringe may be additionally prepared. In this case, positive pressure is created in the main channel 113 and a negative pressure is created in the liquid reservoirs 105 to inject a liquid into the liquid reservoirs 105.

In each of the above embodiments, one main channel 113 is provided, and all the metering channels 115 are connected to the main channel 113. However, the channel configuration of the dispensing device according to the present invention is not limited thereto. For example, two or more main channels may be provided. In this case, one or more metering channels may be connected to each of the main channels.

Further, the main channel 113 can be hermetically sealed. The main channel 113 can be hermetically sealed by, for example, allowing the both ends of the main channel to be openable and closable. In this regard, it is to be noted that the phrase "allowing the both ends of the introduction channel or the main channel to be openable and closable" includes a case where each end of the introduction channel or the main channel is connected to another space and the end of this 'another' space located on the opposite side from the introduction channel or the main channel is openable and closable. In the above embodiments, such 'another' space corresponds to, for example, the channel 113a, the liquid drain space 129, the drain space air vent channel 123, and the channel 123a.

Further, the liquid reservoir air vent channels 119 and 121 are configured so that the ends thereof located on the opposite side from the liquid reservoirs 105 can be hermetically sealed. The liquid reservoir air vent channel can be hermetically sealed by, for example, allowing the end of the liquid reservoir air vent channel located on the opposite side from the liquid reservoir to be openable and closable. In this regard, it is to be noted that the phrase "allowing the end of the liquid reservoir air vent channel located on the opposite side from the liquid reservoir to be openable and closable" includes a case where the end of the liquid reservoir air vent channel located on the opposite side from the liquid reservoir is connected to another space and the end of this 'another' space located on the opposite side from the liquid reservoir air vent channel is openable and closable. In the above embodiments, such another space corresponds to, for example, the air drain space 131, the drain space air vent channel 125, and the channel 125a.

In the above embodiments, the inflow-withstanding pressure of the high inflow-withstanding pressure section is made higher than that of the branch channel by causing a difference in negative capillary force between the branch channel and the high inflow-withstanding pressure section by allowing the branch channel and the high inflow-withstanding pressure section to have different channel widths from each other. However, a difference in negative capillary force between the branch channel and the high inflow-withstanding pressure section may be caused by allowing the branch channel and the high inflow-withstanding pressure section to have different cross-sectional circumferences from each other by allowing the branch channel and the high inflow-withstanding pressure section to have different channel depths from each other or by allowing the branch channel and the high inflow-withstanding pressure section to have different channel widths and channel depths from each other.

A method for producing the dispensing device according to the present invention is not limited to PDMS molding. The dispensing device according to the present invention can be produced also by, for example, forming grooves and recesses for forming the main channel, the branch channels, the liquid reservoirs, and the air vent channels in the surface of a silicon substrate by dry etching and then coating the inner wall surface of these grooves and recesses with a fluorocarbon film by CVD (chemical vapor deposition).

As is clear from the above formula (1), the interfacial tension of the channel inner wall of the high inflow-withstanding pressure section may be made different from that of the branch channel to make the inflow-withstanding pressure of the high inflow-withstanding pressure section higher than that of the branch channel. The branch channel and the high inflow-withstanding pressure section may be made different from each other in both the cross-sectional circumference of a channel and the interfacial tension of a channel inner wall.

Referring to FIG. 21, an embodiment in which the inflow-withstanding pressure of the high inflow-withstanding pressure section is made higher than that of the branch channel by allowing the branch channel and the high inflow-withstanding pressure section to have different interfacial tensions of a channel inner wall from each other will be described.

Embodiment 3

Figure 21A:
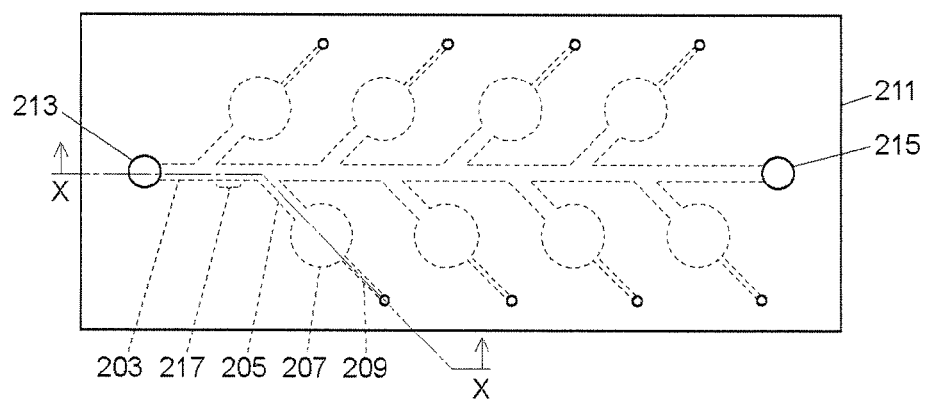
FIG. 21A is a plan view showing the structure of a dispensing device according to another embodiment of the present invention.
Figure 21B:
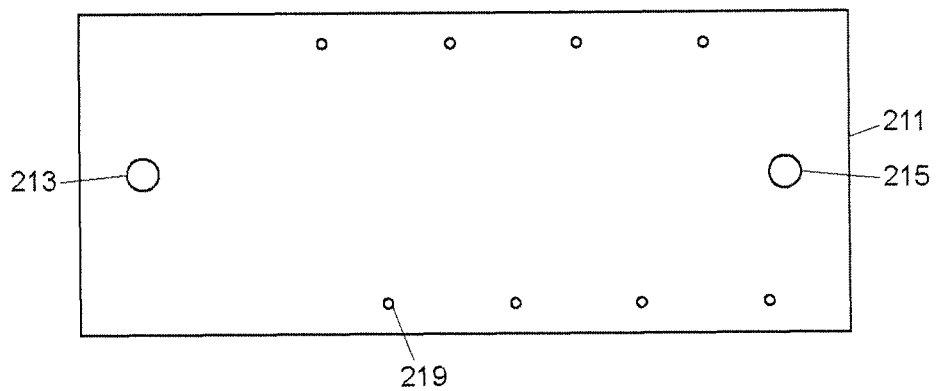
FIG. 21B is a plan view of a cover substrate of the dispensing device according to the embodiment.
Figure 21C:
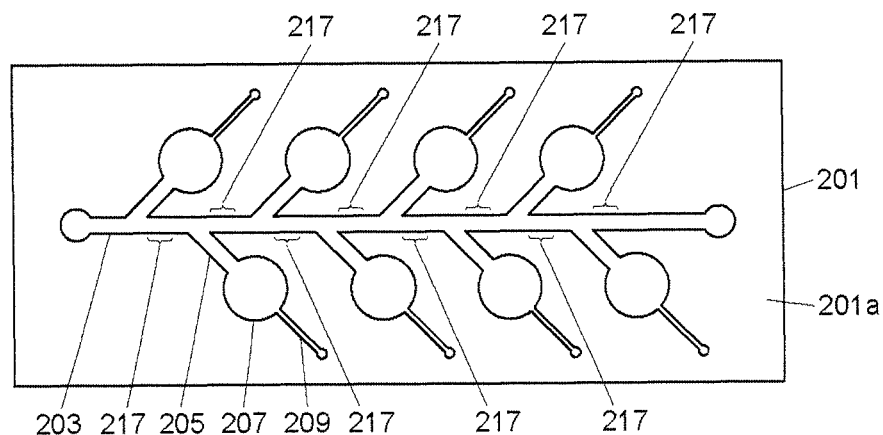
FIG. 21C is a plan view of a base substrate of the dispensing device according to the embodiment.
Figure 21D:
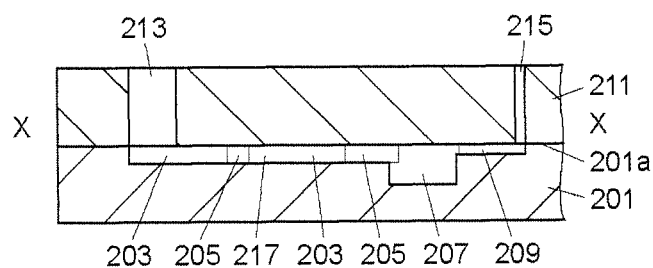
FIG. 21D is a sectional view taken along the X-X line of FIG. 21A.

FIGS. 21A, 21B, 21C, and 21d are Drawings Showing the structure of a dispensing device according to another embodiment of the present invention, wherein FIG. 21A is a plan view of the dispensing device, FIG. 21B is a plan view of a cover substrate, FIG. 21C is a plan view of a base substrate, and FIG. 21D is a sectional view taken along the X-X line of FIG. 21A.

One surface 201a of a base substrate 201 has a groove for forming a main channel 203 and a plurality of branch channels 205 which constitute a liquid sample introduction channel, recesses for forming a plurality of liquid reservoirs 207, and grooves for forming a plurality of air vent channels 209. The surface 201a of the base substrate 201 is bonded to a cover substrate 211. The main channel 203, the branch channels 205, the liquid reservoirs 207, and the air vent channels 209 are formed by covering, with the cover substrate 211, the grooves and recesses provided in the surface 201a of the base substrate 201.

The cover substrate 211 has a sample inlet 213 provided at a position corresponding to one end of the main channel 203. The sample inlet 213 is constituted of a through hole. The cover substrate 211 also has a sample outlet 215 provided at a position corresponding to the other end of the main channel 203. The sample outlet 215 is also constituted of a through hole.

The branch channels 205 are connected to the main channel 203 between the sample inlet 213 and the sample outlet 215. The number of the branch channels 205 is the same as that of the liquid reservoirs 207. The branch channels 205 are also connected to the different liquid reservoirs 207 respectively at their ends located on the opposite side from the main channel 203.

In the main channel 203, a plurality of high inflow-withstanding pressure sections 217 are provided between the branch channels 205 and 205 and between the branch channel 205 and the sample outlet 215. At least part of the inner wall of each of the high inflow-withstanding pressure sections 217 is subjected to surface treatment to increase the contact angle of a liquid sample. This makes it possible to make the inflow-withstanding pressure of the high inflow-withstanding pressure section 217 higher than that of the branch channel 205.

The air vent channel 209 is also connected to the liquid reservoir 207 at a position different from a position where the branch channel 205 is connected to the liquid reservoir 207. The cover substrate 211 has a plurality of air outlets 219 provided at positions corresponding to the ends of the air vent channels 209 located on the opposite side from the liquid reservoirs 207. The air outlet 219 is constituted of a through hole.

The materials of the base substrate 1 and the cover substrate 211 are not particularly limited, but are preferably cheaply available when the dispensing device is designed to be disposable. Examples of the material of the base substrate 201 include polydimethylsiloxane (PDMS) and silicone rubber. Examples of the material of the cover substrate 211 include resin materials such as polypropylene and polycarbonate.

The surface treatment of the inner wall of the high inflow-withstanding pressure section 217 is performed by, for example, dropping a fluorine coating agent onto at least part of the high inflow-withstanding pressure section 217. More specifically, for example, a fluorine coating agent ("NOVEC EGC-1700" manufactured by 3M) is dropped onto the high inflow-withstanding pressure section 217 and is then naturally dried.

The design examples of the main channel 203, the branch channel 205, the air vent channel 209, and the high inflow-withstanding pressure section 217 are as follows. The depth of the main channel 203, the branch channel 205, and the high inflow-withstanding pressure section 217 is 200 µm. The width of the main channel 203 and the branch channel 205 is 500 µm. The width of the high inflow-withstanding pressure section 217 is the same as that of the main channel, i.e., 500 µm. The depth and width of the air vent channel 209 are both 10 µm.

When the base substrate 201 is formed by molding PDMS ("SYLGARD184" manufactured by Dow Corning), the contact angle of deionized water as a liquid sample on a channel inner wall is about 108°, and when the cover substrate 211 is made of polypropylene, the contact angle of deionized water as a liquid sample on a channel inner wall is about 95°. On the other hand, the contact angle of deionized water on a surface coated with a fluorine coating agent ("NOVEC EGC-1700" manufactured by 3M) is about 105°.

When part of the cover substrate 211 constituting the high inflow-withstanding pressure section 217 is coated with a fluorine coating agent ("NOVEC EGC-1700" manufactured by 3M), the inner wall of the branch channel 205 has a surface made of PDMS and a surface made of polypropylene, and the inner wall of the high inflow-withstanding pressure section 217 has a surface made of PDMS and a surface made of the fluorine coating agent.

When the dispensing device is produced based on the above design examples, a pressure induced by the negative capillary force of the branch channel 205 is about −234 Pa, and a pressure induced by the negative capillary force of the high inflow-withstanding pressure section 217 is about −297 Pa. By subjecting at least part of the high inflow-withstanding pressure section 217 to surface treatment in such a manner as described above to increase the contact angle of a sample solution, it is possible to make the inflow-withstanding pressure of the high inflow-withstanding pressure section 217 higher than that of the branch channel 205.

The inflow-withstanding pressure of the high inflow-withstanding pressure section 217 can be increased by a method other than surface treatment of the inner wall of the high inflow-withstanding pressure section 217. For example, the surface roughness of at least part of the inner wall of the high inflow-withstanding pressure section 217 may be increased to increase the inflow-withstanding pressure of the high inflow-withstanding pressure section 217.

When the contact angle of a reagent solution on the inner wall is defined as θ and the surface area of the inner wall is increased γ times by increasing the surface roughness of the inner wall, an apparent contact angle $\theta_r$ is given by the Winzel's formula:

[Formula 2]

$$\cos \theta_r = \gamma \cos \theta \; (\gamma > 1) \tag{2}$$

As can be seen from the above formula (2), when the contact angle θ is larger than 90°, the apparent contact angle is increased by increasing the surface roughness of the inner wall. That is, the inflow-withstanding pressure of the high inflow-withstanding pressure section 217 to withstand the inflow of a reagent solution can be increased by increasing the surface roughness of at least part of the inner wall of the high inflow-withstanding pressure section 217.

Embodiment 4

Figure 22A:
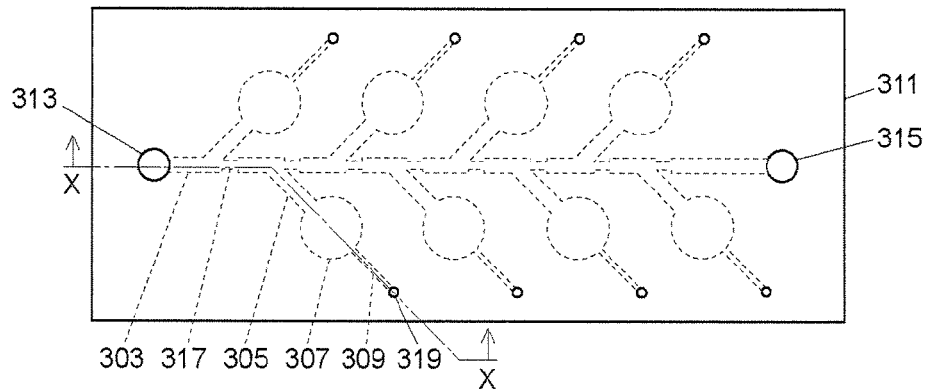
FIG. 22A is a plan view showing the structure of a dispensing device according to another embodiment of the present invention.
Figure 22B:
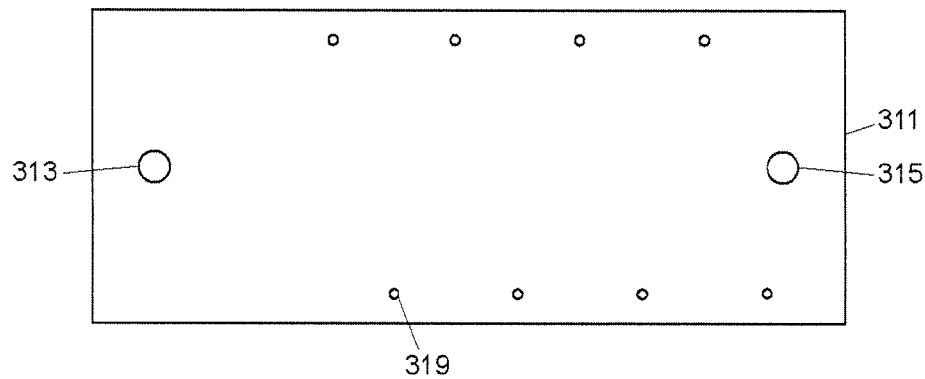
FIG. 22B is a plan view of a cover substrate of the dispensing device shown in FIG. 22A.
Figure 22C:
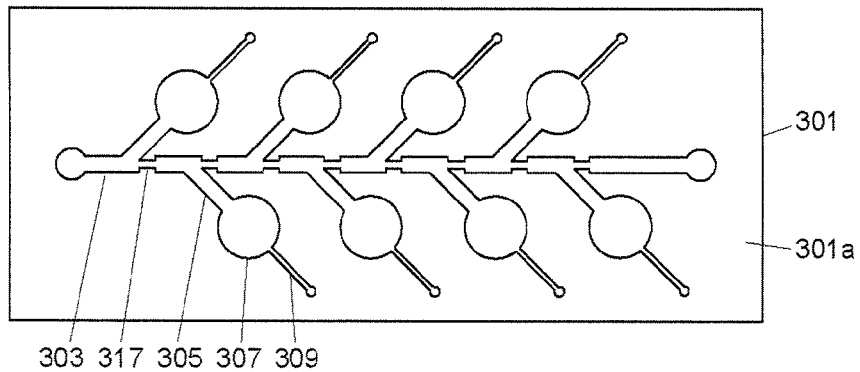
FIG. 22C is a plan view of a base substrate of the dispensing device shown in FIG. 22A.
Figure 22D:
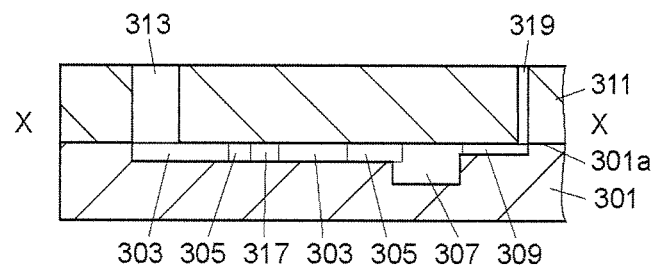
FIG. 22D is a sectional view taken along the X-X line of FIG. 22A.

FIGS. 22A, 22B, 22C, and 22D are drawings showing the structure of a dispensing device according to another embodiment of the present invention, wherein FIG. 22A is a plan view of the dispensing device, FIG. 22B is a plan view of a cover substrate, FIG. 22C is a plan view of a base substrate, and FIG. 22D is a sectional view taken along the X-X line of FIG. 22A.

One surface 301a of a base substrate 301 has a groove for forming a main channel 303 and a plurality of branch channels 305 which constitute a liquid sample introduction channel, recesses for forming a plurality of liquid reservoirs 307, and grooves for forming a plurality of air vent channels 309. The surface 301a of the base substrate 301 is bonded to a cover substrate 311. The main channel 303, the branch channels 305, the liquid reservoirs 307, and the air vent channels 309 are formed by covering, with the cover substrate 311, the grooves and recesses provided in the surface 301a of the base substrate 301.

The cover substrate 311 has a sample inlet 313 provided at a position corresponding to one end of the main channel 303. The sample inlet 313 is constituted of a through hole. The cover substrate 311 also has a sample outlet 315 provided at a position corresponding to the other end of the main channel 303. The sample outlet 315 is also constituted of a through hole.

The branch channels 305 are connected to the main channel 303 between the sample inlet 313 and the sample outlet 315. The number of the branch channels 305 is the same as that of the liquid reservoirs 307. The branch channels 305 are each also connected to the different liquid reservoirs 307 at their ends located on the opposite side from the main channel 303.

In the main channel 303, a plurality of high inflow-withstanding pressure sections 317 are provided between the branch channels 305 and 305 and between the branch channel 305 and the sample outlet 315. The high inflow-withstanding pressure section 317 has a shorter cross-sectional circumference than the branch channel 305, and therefore, has a higher inflow-withstanding pressure than the branch channel 305. The main channel 303 and the high inflow-withstanding pressure section 317 are substantially rectangular in cross section. When the dispensing device is seen from above, both side walls of the high inflow-withstanding pressure section 317 project from the side walls of the main channel 303 toward the center of the main channel 303. Therefore, at the connection between the main channel 303 and the high inflow-withstanding pressure section 317, only two inner wall surfaces, that is, only the top and bottom inner wall surfaces are continuous and flat surfaces.

The air vent channel 309 is also connected to the liquid reservoir 307 at a position different from a position where the branch channel 305 is connected to the liquid reservoir 307. The cover substrate 311 has a plurality of air outlets 319 provided at positions corresponding to the ends of the air vent channels 309 located on the opposite side from the liquid reservoirs 307. The air outlet 319 is constituted of a through hole.

The materials of the base substrate 1 and the cover substrate 311 are not particularly limited, but are preferably cheaply available when the dispensing device is designed to be disposable. Examples of the material of the base substrate 301 include polydimethylsiloxane (PDMS) and silicone rubber. Examples of the material of the cover substrate 311 include resin materials such as polypropylene and polycarbonate.

The design examples of the main channel 303, the branch channel 305, the air vent channel 309, and the high inflow-withstanding pressure section 317 are as follows. The depth of the main channel 303, the branch channel 305, and the high inflow-withstanding pressure section 317 is 500 μm. The width of the main channel 303 and the branch channel 305 is 500 μm. The width of the high inflow-withstanding pressure section 317 is 200 μm. The depth and width of the air vent channel 309 are both 10 μm.

When the base substrate 301 is formed by molding PDMS ("SYLGARD184" manufactured by Dow Corning), the contact angle of deionized water as a liquid sample on a channel inner wall is about 108°, and when the cover substrate 311 is made of polypropylene, the contact angle of deionized water as a liquid sample on a channel inner wall is about 95°.

When the dispensing device is produced based on the above design examples, a pressure induced by the negative capillary force of the branch channel 305 is about −148 Pa, and a pressure induced by the negative capillary force of the high inflow-withstanding pressure section 317 is about −283 Pa. By making the cross-sectional circumference of the high inflow-withstanding pressure section 317 shorter than that of the branch channel 305, it is possible to make the inflow-withstanding pressure of the high inflow-withstanding pressure section 317 higher than that of the branch channel 305. Further, by reducing the number of continuous and flat inner wall surfaces at the connection between the main channel 303 and the high inflow-withstanding pressure section 317 to two (i.e., top and bottom inner wall surfaces), a liquid sample becomes less likely to flow from the main channel 303 into the high inflow-withstanding pressure section 317 as compared to a case where the number of continuous and flat inner wall surfaces at the connection between the main channel 303 and the high inflow-withstanding pressure section 317 is three. This makes it easy to allow a liquid sample to come to rest by the high inflow-withstanding pressure section 317 with more stability.

Figure 23:
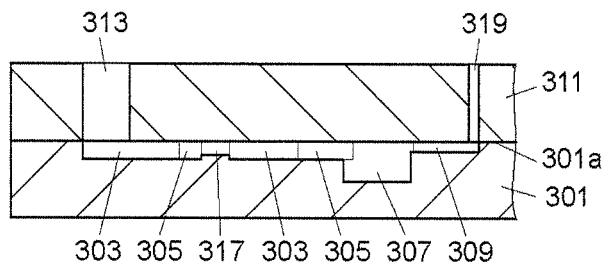
FIG. 23 is a sectional view showing the structure of a dispensing device according to another embodiment of the present invention.

As shown in FIG. 23, the number of continuous and flat inner wall surfaces at the connection between the main channel 303 and the high inflow-withstanding pressure section 317 of the dispensing device shown in FIGS. 22A to 22D may be reduced to one (i.e., only top inner wall surface) by further projecting the channel bottom of the high inflow-withstanding pressure section 317 from the channel bottom of the main channel 303. In this case, a liquid sample becomes much less likely to flow from the main channel 303 into the high inflow-withstanding pressure section 317.

Figure 24:
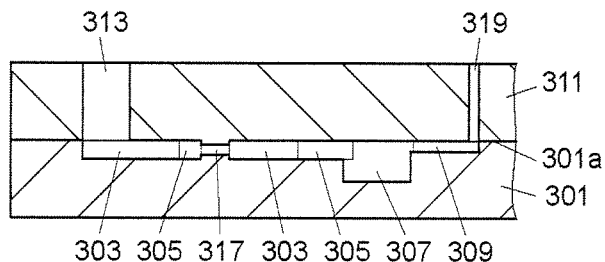
FIG. 24 is a sectional view showing the structure of a dispensing device according to another embodiment of the present invention.

As shown in FIG. 24, the number of continuous and flat inner wall surfaces at the connection between the main channel 303 and the high inflow-withstanding pressure section 317 of the dispensing device shown in FIGS. 22A to 22D may be reduced to zero by further projecting the channel bottom of the high inflow-withstanding pressure section 317 from the channel bottom of the main channel 303 and by further projecting the channel top of the high inflow-withstanding pressure section 317 from the channel top of the main channel 303. In this case, a liquid sample becomes much less likely to flow from the main channel 303 into the high inflow-withstanding pressure section 317.

In the dispensing devices shown in FIGS. 22A to 22D, FIG. 23, and FIG. 24, at least part of the inner wall of the high inflow-withstanding pressure section 317 may be subjected to surface treatment to increase the contact angle of a sample solution. The surface treatment of the inner wall of the high inflow-withstanding pressure section 317 may be performed by, for example, dropping a fluorine coating agent onto at least part of the high inflow-withstanding pressure section 317. More specifically, for example, a fluorine coating agent ("NOVEC EGC-1700" manufactured by 3M) is dropped onto the high inflow-withstanding pressure section 317 and is then naturally dried. This makes it possible to further increase the inflow-withstanding pressure of the high inflow-withstanding pressure section 317.

Embodiment 5

Figure 25A:
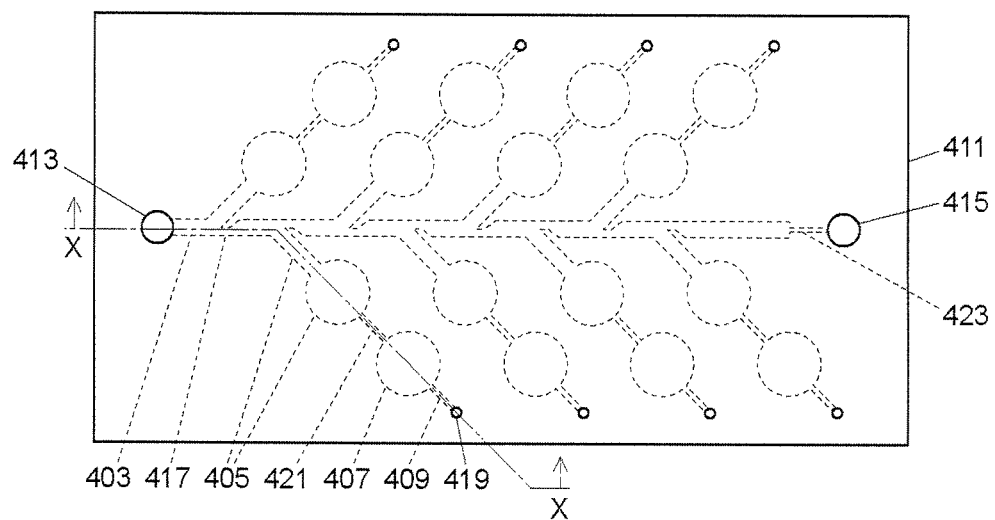
FIG. 25A is a plan view showing the structure of a dispensing device according to another embodiment of the present invention.
Figure 25B:
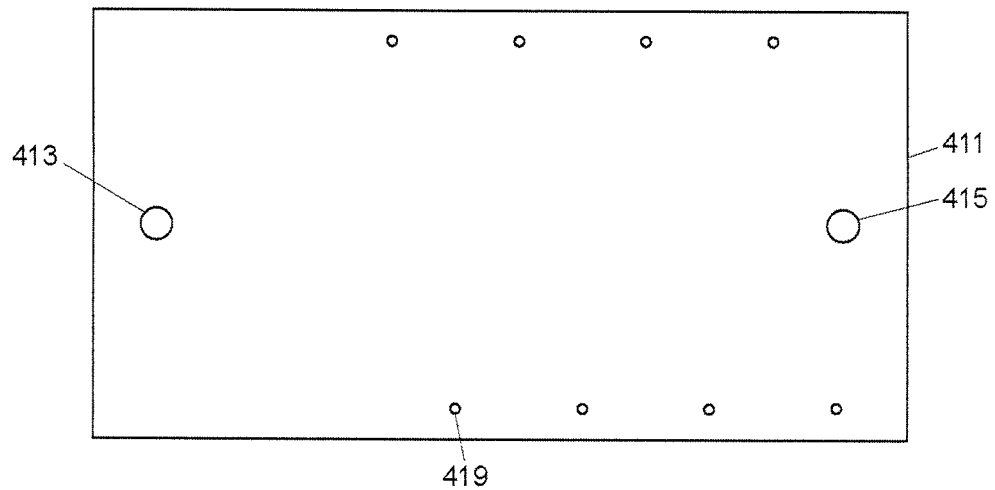
FIG. 25B is a plan view of a cover substrate of the dispensing device according to the embodiment.
Figure 25C:
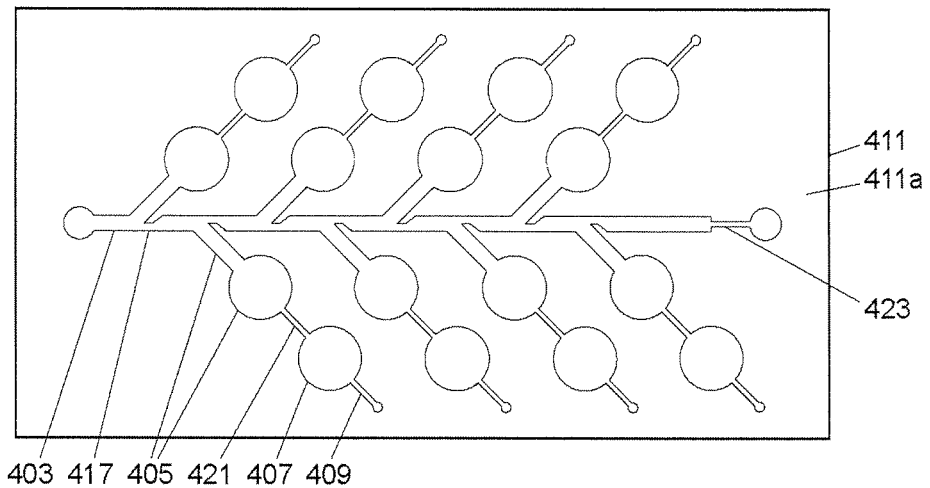
FIG. 25C is a plan view of a base substrate of the dispensing device according to the embodiment.
Figure 25D:
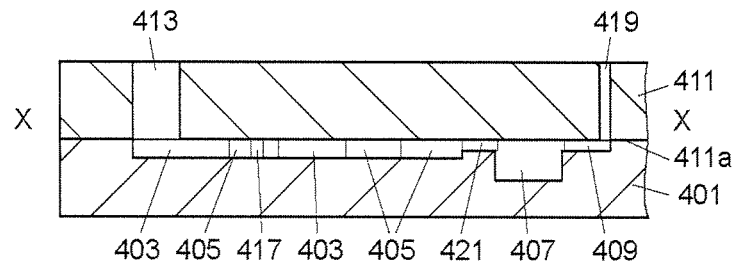
FIG. 25D is a sectional view taken along the X-X line of FIG. 25A.

FIGS. 25A, 25B, 25C, and 25D are drawings showing the structure of a dispensing device according to another embodiment of the present invention, wherein FIG. 25A is a plan view of the dispensing device, FIG. 25B is a plan view of a cover substrate, FIG. 25C is a plan view of a base substrate, and FIG. 25D is a sectional view taken along the X-X line of FIG. 25A.

One surface 401a of a base substrate 401 has a groove for forming a main channel 403, a plurality of metering channels 405, and a plurality of injection channels 421 which constitute a liquid sample introduction channel, recesses for forming a plurality of liquid reservoirs 407, and grooves for forming a plurality of air vent channels 409. The surface 401a of the base substrate 401 is bonded to a cover substrate 411. The main channel 403, the metering channels 405, the injection channels 421, the liquid reservoirs 407, and the air vent channels 409 are formed by covering, with the cover substrate 411, the grooves and recesses provided in the surface 401a of the base substrate 401.

The cover substrate 411 has a sample inlet 413 provided at a position corresponding to one end of the main channel 403. The sample inlet 413 is constituted of a through hole. The cover substrate 411 also has a sample outlet 415 provided at a position corresponding to the other end of the main channel 403. The sample outlet 415 is also constituted of a through hole.

The metering channels 405 are connected to the main channel 403 between the sample inlet 413 and the sample outlet 415. The number of the metering channels 405 is the same as that of the liquid reservoirs 407. The metering channels 405 are each connected through the injection channels 421 to the different liquid reservoirs 407 at their ends located on the opposite side from the main channel 403. The injection channel 421 has an inner wall surface forming a contact angle of 90° or larger with a liquid sample, and has a higher inflow-withstanding pressure than a high inflow-withstanding pressure section 417 (which will be described later). The injection channel 421 does not allow the passage of a liquid sample at a liquid sample introduction pressure applied to introduce the liquid sample into the main channel 403 and the metering channels 405 and at a purge pressure applied to purge the liquid sample from the main channel 403 but allows the passage of the liquid sample at a pressure higher than the liquid sample introduction pressure and the purge pressure.

In the main channel 403, the high inflow-withstanding pressure sections 417 are provided between the metering channels 405 and 405 and between the metering channel 405 and the sample outlet 415. The high inflow-withstanding pressure section 417 has a shorter cross-sectional circumference than the metering channel 405, and therefore, has a higher inflow-withstanding pressure than the metering channel 405.

In the main channel 403, a second high inflow-withstanding pressure section 423 is further provided between the sample outlet 415 and the high inflow-withstanding pressure section 417 provided between the metering channel 405 and the sample outlet 415, and is spaced from the high inflow-withstanding pressure section 417. The second high inflow-withstanding pressure section 423 has a shorter cross-sectional circumference than the high inflow-withstanding pressure section 417, and therefore, has a higher inflow-withstanding pressure than the high inflow-withstanding pressure section 417.

The air vent channel 409 is also connected to the liquid reservoir 407 at a position different from a position where the metering channel 405 is connected to the liquid reservoir 407. The cover substrate 411 has a plurality of air outlets 419 provided at positions corresponding to the ends of the air vent channels 409 located on the opposite side from the liquid reservoirs 407. The air outlet 419 is constituted of a through hole.

The design examples of the main channel 403, the metering channel 405, the injection channel 421, the air vent channel 409, the high inflow-withstanding pressure section 417, and the second high inflow-withstanding pressure section 423 are as follows. The depth of the main channel 403, the metering channel 405, and the high inflow-withstanding pressure section 417 is 500 μm. The width of the main channel 403 is 500 μm. The length and width of the metering channel 405 are set so that the metering channel 405 can contain a predetermined amount of a liquid sample. The width and depth of the injection channel 421 are 100 μm and 50 μm, respectively. The width of the high inflow-withstanding pressure section 417 is 200 μm. The width and depth of the second high inflow-withstanding pressure section 423 are 50 μm and 20 μm, respectively. The depth and width of the air vent channel 409 are both 10 μm.

When the base substrate 401 is formed by molding PDMS ("SYLGARD184" manufactured by Dow Corning), the contact angle of deionized water as a liquid sample on a channel inner wall is about 108°, and when the cover substrate 411 is made of polypropylene, the contact angle of deionized water as a liquid sample on a channel inner wall is about 95°.

When the dispensing device is produced based on the above design examples so that the width of the narrowest part of the metering channel becomes, for example, 500 μm, a pressure induced by the negative capillary force of the metering channel 405 is about −148 Pa, a pressure induced by the negative capillary force of the high inflow-withstanding pressure section 417 is about −283 Pa, and the injection channel 421 has a inflow-withstanding pressure of about 1023 Pa. Therefore, the metering channel 405 can be filled with a liquid sample by feeding the liquid sample at a liquid feed pressure equal to or less than the inflow-withstanding pressure of the injection channel 421. Further, the liquid sample can be purged from the main channel 403 by feeding a gas into the main channel 403 at a pressure similar to the liquid feed pressure.

FIGS. 26A, 26B, 26C, and 26D are schematic plan views showing how a liquid sample is introduced into the liquid reservoirs 407. In these plan views, a fine dot pattern indicates a liquid sample, a solid arrow indicates the flow of a liquid sample, and an open arrow indicates the flow of air. Hereinbelow, a series of steps in the process of introducing a liquid sample into the liquid reservoirs 407 will be described with reference to FIGS. 26A to 26D.

Figure 26A:
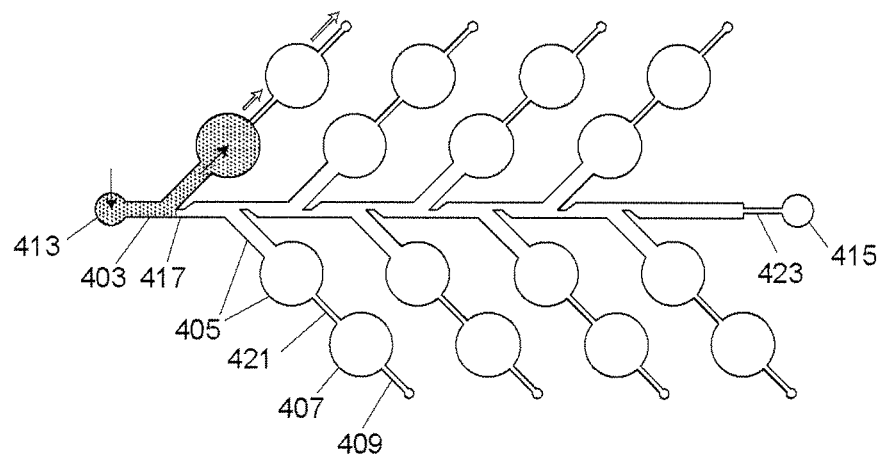
FIG. 26A is a schematic plan view of the entire dispensing device according to the embodiment, which shows the first step in the process of introducing a liquid sample into liquid reservoirs.

First, referring to FIG. 26A, a liquid sample is introduced into the main channel 403 through the sample inlet 413. The liquid sample introduced into the main channel 403 reaches a branch point between the first metering channel 405 and the main channel 403. The liquid sample flows into the first metering channel 405, because, when the dispensing device is seen from the sample inlet 413 side, the high inflow-withstanding pressure section 417 having a higher inflow-withstanding pressure than the metering channel 405 is provided in the main channel 403 between the first branch point and the next branch point. At this time, a gas contained in the metering channel 405 flows through the injection channel 421 into the liquid reservoir 407, and a gas contained in the liquid reservoir 407 flows through the air vent channel 9 and is then discharged through the air outlet 419. Then, the first metering channel 405 is filled with the liquid sample. At this time, it is preferred that the liquid sample does not flow downstream from the high inflow-withstanding pressure section 417. However, the liquid sample may flow downstream from the high inflow-withstanding pressure section 417 as long as the amount of the liquid sample flowing downstream from the high inflow-withstanding pressure section 417 is smaller than that of the liquid sample flowing into the metering channel 405.

Figure 26B:
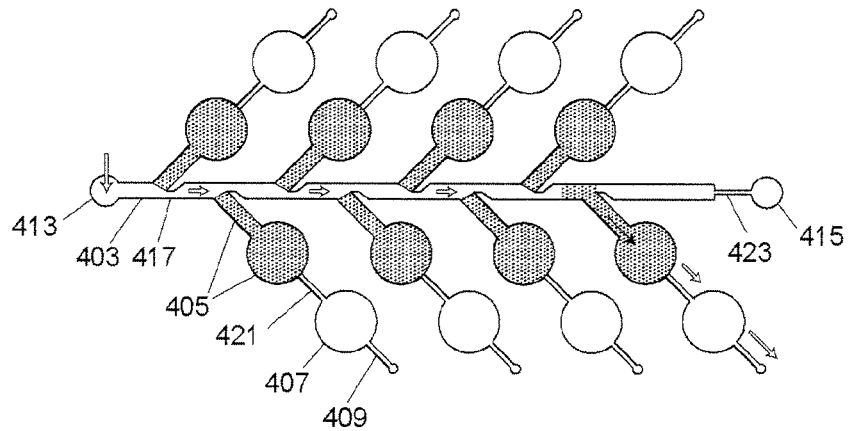
FIG. 26B is a schematic plan view of the entire dispensing device according to the embodiment, which shows a step following the step shown in FIG. 26A in the process of introducing a liquid sample into liquid reservoirs.

Next, referring to FIG. 26B, after the first metering channel 405 is filled with the liquid sample, the liquid sample passes through the high inflow-withstanding pressure section 417 and is then led to a branch point between the next metering channel 405 and the main channel 403. This is because the high inflow-withstanding pressure section 417 has a lower inflow-withstanding pressure than the injection channel 421. The liquid sample that has reached the branch point between the next metering channel 405 and the main channel 403 flows into the metering channel 405. After this, the metering channels 405 are filled with the liquid sample one after another from the upstream side to the downstream side of the main channel 403.

After the liquid sample is introduced into the main channel 403 in an amount at least equal to the total volume of all the metering channels 405 (e.g., after the liquid sample is introduced into the main channel 403 in an amount slightly larger than the total volume of all the metering channels 405), air is introduced into the main channel 403 through the sample inlet 413 instead of the liquid sample. The introduction of air into the main channel 403 allows the liquid sample present in the main channel 403 to flow downstream into the metering channels 405. As a result, the most downstream metering channel 405 connected to the main channel 403 is filled with the liquid sample. As described above, by introducing air instead of a liquid sample into the main channel 403 after the completion of introduction of the liquid sample into the main channel 403, the dead volume of the liquid sample can be reduced. It is to be noted that this dispensing device is capable of reducing the dead volume of a liquid sample as compared to a conventional dispensing device even when air is not introduced into the main channel 403 instead of the liquid sample because the channel configuration of this dispensing device is simpler than a conventional complicated flow configuration.

Figure 26C:
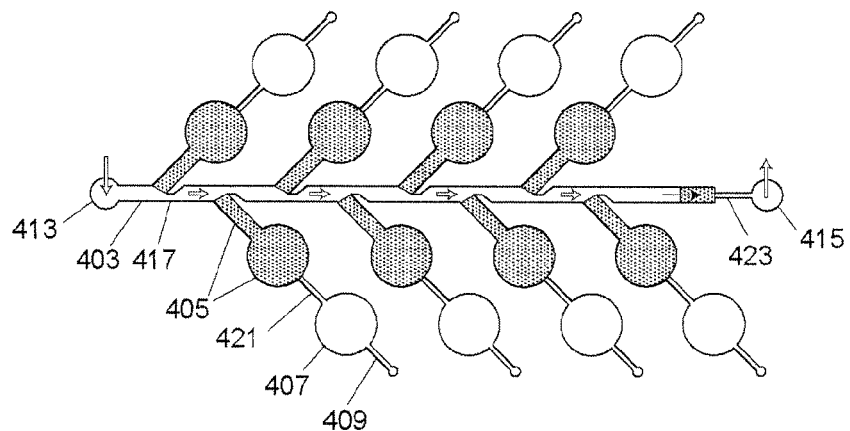
FIG. 26C is a schematic plan view of the entire dispensing device according to the embodiment, which shows a step following the step shown in FIG. 26B in the process of introducing a liquid sample into liquid reservoirs.

Then, referring to FIG. 26C, after the most downstream metering channel 405 connected to the main channel 403 is filled with the liquid sample, the liquid sample remaining in the main channel 403 (dead volume) reaches the second high inflow-withstanding pressure section 423. The liquid sample that has reached the second high inflow-withstanding pressure section 423 is less likely to flow toward the sample outlet 415 because the second high inflow-withstanding pressure section 423 has a higher inflow-withstanding pressure than the main channel 403.

Figure 26D:
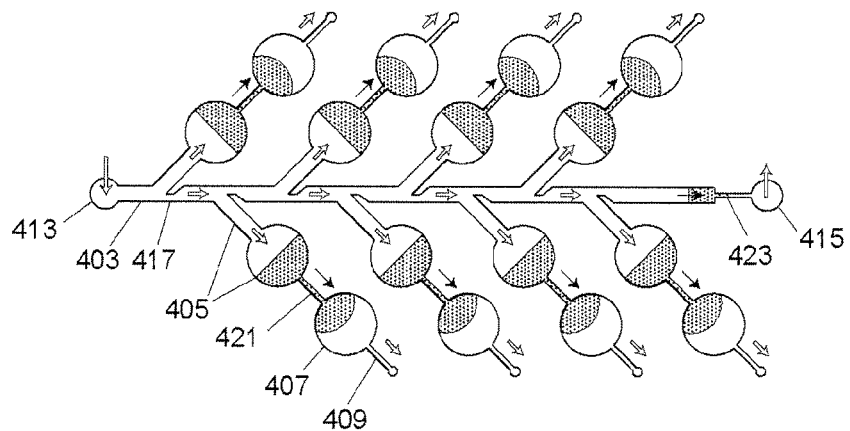
FIG. 26D is a schematic plan view of the entire dispensing device according to the embodiment, which shows a step following the step shown in FIG. 26C in the process of introducing a liquid sample into liquid reservoirs.

Then, referring to FIG. 26D, air is allowed to continue to flow into the main channel 403 from the sample inlet 413 side in a state shown in FIG. 26C by driving, for example, a system for feeding liquid or gas at a constant output, and as a result, the pressure in the main channel 403 is increased and then a pressure higher than the purge pressure is applied to the inside of the main channel 403. This makes it possible to inject the liquid sample contained in the metering channels 405 into the liquid reservoirs 407 through the injection channels 421. At this time, part or all of the liquid sample that has reached the second high inflow-withstanding pressure section 423 may flow into the second high inflow-withstanding pressure section 423, but it is preferred that the liquid sample does not flow into the second high inflow-withstanding pressure section 423. After a lapse of predetermined time, the injection of the liquid sample through the injection channels 421 into the liquid reservoirs 407 is completed.

As described above, a liquid sample contained in the metering channels 405 can be injected into the liquid reservoirs 407 without hermetically sealing the sample outlet 415 side of the main channel 403 with the use of a switching valve or the like. This makes it possible to simplify the channel configuration of the dispensing device.

Further, feeding of a liquid sample, purging, and injection of a liquid sample into the liquid reservoirs 407 can be performed without changing the driving output of the system for feeding liquid or gas such as a syringe pump. This makes it easy to control the system for feeding liquid or gas. However, the driving outputs of the system for feeding liquid or gas during feeding of a liquid sample, purging, and injection of a liquid sample into the liquid reservoirs may be different from each other.

According to the embodiment shown in FIG. 25A, the cross-sectional circumference of the second high inflow-withstanding pressure section 423 is made shorter than that of the main channel 403 by making the width and depth of the second high inflow-withstanding pressure section 423 shorter than those of the main channel 403. However, the structure of the second high inflow-withstanding pressure section 423 is not limited thereto. The structure of the second high inflow-withstanding pressure section 423 is not particularly limited as long as it has a higher inflow-withstanding pressure than the high inflow-withstanding pressure section 417. Hereinbelow, other structural examples of the second high inflow-withstanding pressure section 423 will be described.

Figure 27A:
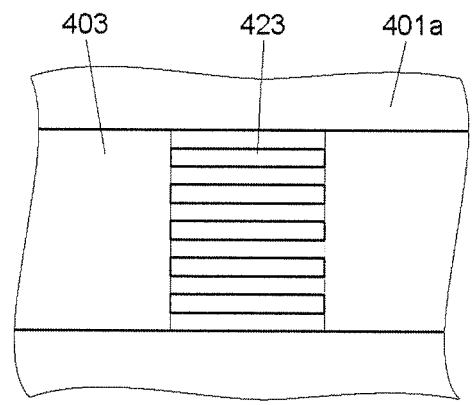
FIG. 27A is a plan view showing another structural example of a second high inflow-withstanding pressure section.
Figure 27B:
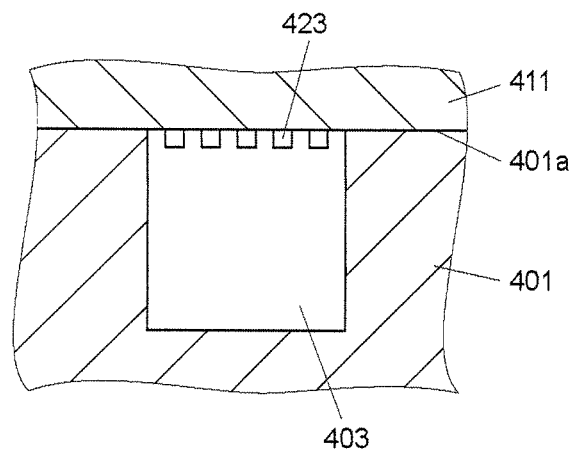
FIG. 27B is a sectional view of the second high inflow-withstanding pressure section shown in FIG. 27A.

FIGS. 27A and 27B are drawings of another structural example of the second high inflow-withstanding pressure section 423, wherein FIG. 27A is a plan view and FIG. 27B is a sectional view.

This structural example of the second high inflow-withstanding pressure section 423 is constituted of a plurality of narrow holes having a shorter cross-sectional circumference than the high inflow-withstanding pressure section 423. The main channel 403 has a width of 500 μm and a depth of 500 μm. Each of the narrow holes constituting the second high inflow-withstanding pressure section 423 has a depth of, for example, 10 μm and a width of, for example, 20 μm, the pitch between adjacent narrow holes is, for example, 20 μm, and 13 grooves are provided in a region having a width of 500 μm. It is to be noted that in FIGS. 27A and 27B, only a small number of narrow holes constituting the second high inflow-withstanding pressure section 423 are shown.

By forming the second high inflow-withstanding pressure section 423 from a plurality of narrow holes, it is possible to make the inflow-withstanding pressure of the second high inflow-withstanding pressure section 423 higher than that of the high inflow-withstanding pressure section 417.

Figure 28A:
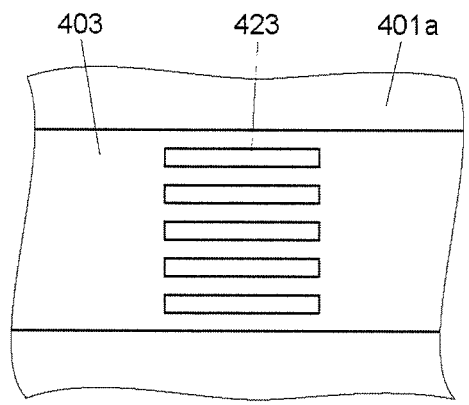
FIG. 28A is a plan view showing another structural example of a second high inflow-withstanding pressure section.
Figure 28B:
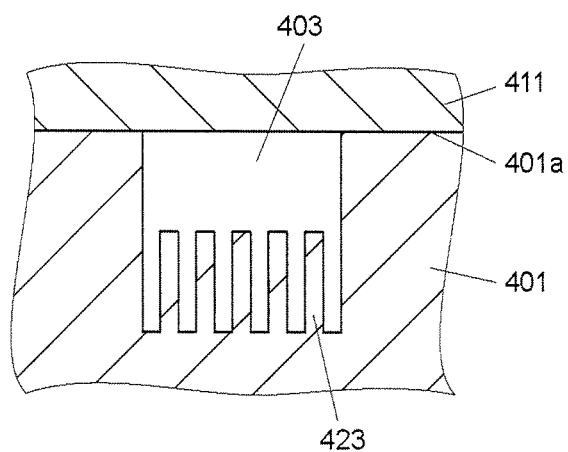
FIG. 28B is a sectional view of the second high inflow-withstanding pressure section shown in FIG. 28A.

FIGS. 28A and 28B are drawings of another structural example of the second high inflow-withstanding pressure section 423, wherein FIG. 28A is a plan view and FIG. 28B is a sectional view.

This structural example of the second high inflow-withstanding pressure section 423 is constituted of a plurality of projections provided on the bottom surface of the main channel 403. These projections are made of the same material as the base substrate 401 and integrally molded with the main channel 403 etc. Each of the projections constituting the second high inflow-withstanding pressure section 423 has a height of, for example, 480 μm, a width of, for example, 20 μm, and a length of, for example, 500 μm, the pitch between adjacent projections is, for example, 20 μm, and 13 projections are provided in a region having a width of 500 μm. It is to be noted that in FIGS. 28A and 28B, only a small number of narrow holes constituting the second high inflow-withstanding pressure section 423 are shown.

By forming the second high inflow-withstanding pressure section 423 from a plurality of projections, it is possible to make the inflow-withstanding pressure of the second high inflow-withstanding pressure section 423 higher than that of the high inflow-withstanding pressure section 417.

Embodiment 6

Figure 29A:
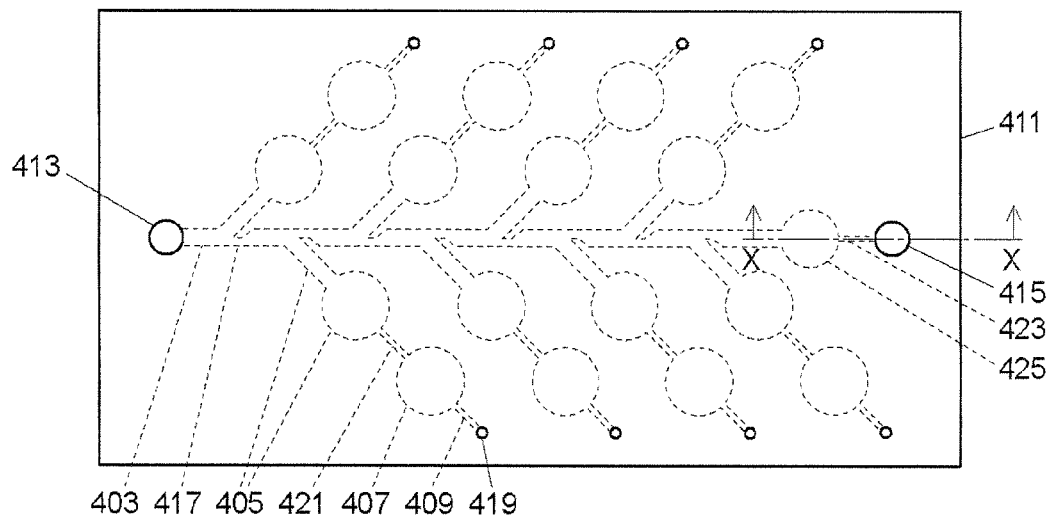
FIG. 29A is a plan view showing the structure a dispensing device according to another embodiment of the present invention.
Figure 29B:
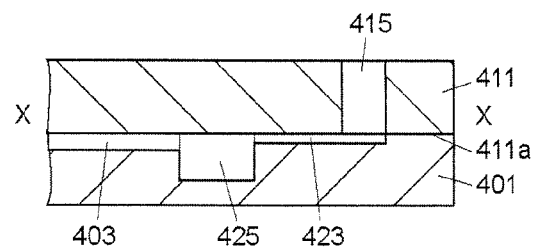
FIG. 29B is a sectional view taken along the X-X line of FIG. 29A.

FIGS. 29A and 29B are drawings showing the structure of a dispensing device according to another embodiment of the present invention, wherein FIG. 29A is a plan view of the dispensing device and FIG. 29B is a sectional view taken along the X-X line of FIG. 29A. The structure of this embodiment is similar to that of the embodiment shown in FIG. 25A.

The structure of this embodiment is the same as that of the embodiment shown in FIG. 25A except that a liquid waste container 425 is provided in the main channel 403 between the most downstream high inflow-withstanding pressure section 417 and the second high inflow-withstanding pressure section 423.

A design example of the liquid waste container 425 is a cylindrical one having an inner diameter of, for example, 3 mm and a depth of, for example, 10 mm. The second high inflow-withstanding pressure section 423 is connected to the liquid waste container 425 so as to be spaced from the bottom of the liquid waste container 425. In this embodiment, the second high inflow-withstanding pressure section 423 is connected to the upper edge of the side surface of the liquid waste container 425. This prevents a liquid sample contained in the liquid waste container 425 from coming into contact with the second high inflow-withstanding pressure section 423.

Figure 30A:
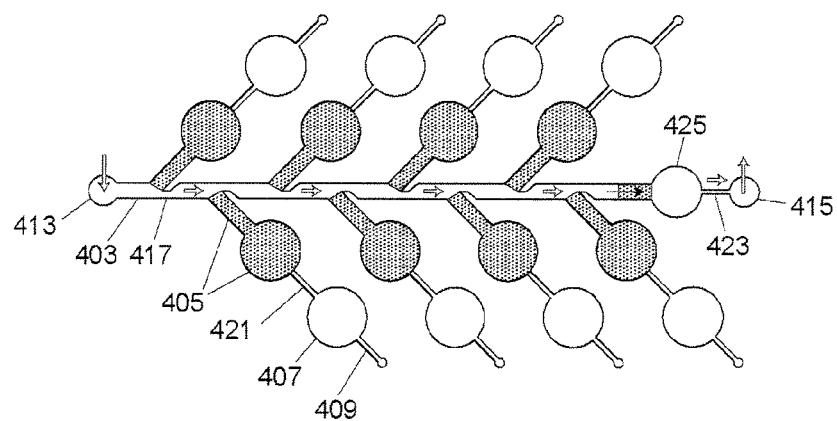
FIG. 30A is a schematic plan view of the entire dispensing device according to the embodiment, which shows one step in the process of introducing a liquid sample into liquid reservoirs.
Figure 30B:
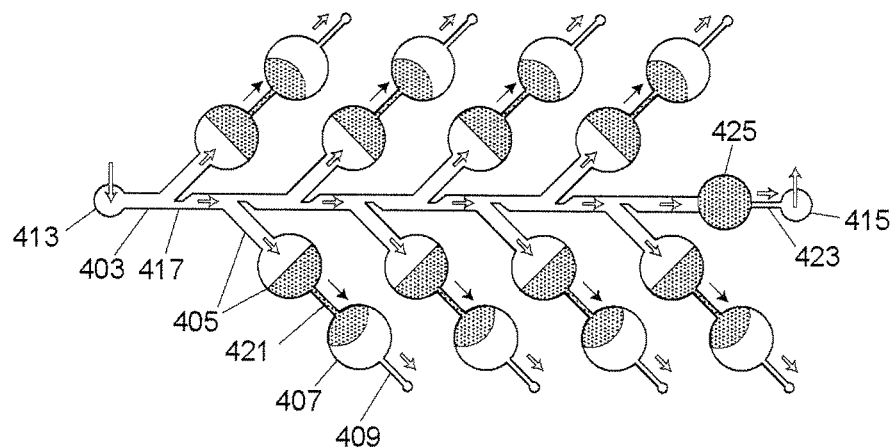
FIG. 30B is a schematic plan view of the entire dispensing device according to the embodiment which shows a step following the step shown in FIG. 30A in the process of introducing a liquid sample into liquid reservoirs.

FIGS. 30A and 30B are schematic plan views showing how a liquid sample is introduced into the liquid reservoirs 407. In these drawings, a fine dot pattern indicates a liquid sample, a solid arrow indicates the flow of a liquid sample, and an open arrow indicates the flow of air. Hereinbelow, a series of steps in the process of introducing a liquid sample into the liquid reservoirs 407 will be described with reference to FIGS. 30A and 30B.

The metering channels 405 connected to the main channel 403 are filled with a liquid sample one after another from the upstream side to the downstream side of the main channel 403 in the same manner as in the steps described above with reference to FIGS. 26A to 26C. Then, as shown in FIG. 30A, the liquid sample remaining in the main channel 403 (dead volume) reaches the liquid waste container 425.

Then, referring to FIG. 30B, the dead volume of the liquid sample is contained in the liquid waste container 425. In this state, air is introduced into the main channel 403 through the sample inlet 413 at a flow rate, which is higher than that used for feeding the liquid sample and that used for feeding air for purging, to increase the pressure in the main channel 403. For example, the flow rate of the liquid sample fed into the main channel 403 and the flow rate of air fed into the main channel 403 for purging are 100 µL/min, and the flow rate of air fed into the main channel 403 to apply a higher pressure to the inside of the main channel 403 is 20000 µL/min. Since the second high inflow-withstanding pressure section 423 has a higher inflow-withstanding pressure than the high inflow-withstanding pressure section 417, the pressure in the main channel 403 can be increased to a level allowing the liquid sample contained in the metering channels 405 to be injected into the liquid reservoirs 407 through the injection channels 421 by feeding air into the main channel 403 at a flow rate higher than that used for purging by increasing the driving output of a system for feeding liquid or gas. As a result, the liquid sample contained in the metering channels 405 is injected into the liquid reservoirs 407 through the injection channels 421.

Also in the case of this embodiment, a liquid sample contained in the metering channels 405 can be injected into the liquid reservoirs 407 without hermetically sealing the sample outlet 415 side of the main channel 403 with the use of a switching valve or the like. This makes it possible to simplify the channel configuration of the dispensing device. Further, a liquid sample is not discharged through the sample outlet 415 but is contained in the liquid waste container 425, thereby reducing concerns about environmental contamination with the liquid sample.

The second high inflow-withstanding pressure section of the embodiment shown in FIG. 29A may have the structure described above with reference to FIGS. 27A and 27B or FIGS. 28A and 28B.

Embodiment 7

Figure 31A:
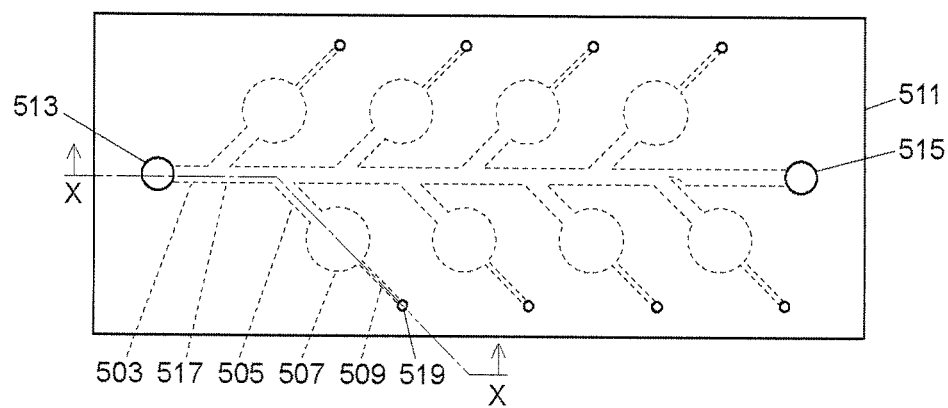
FIG. 31A is a plan view showing the structure of a dispensing device according to another embodiment of the present invention.
Figure 31B:
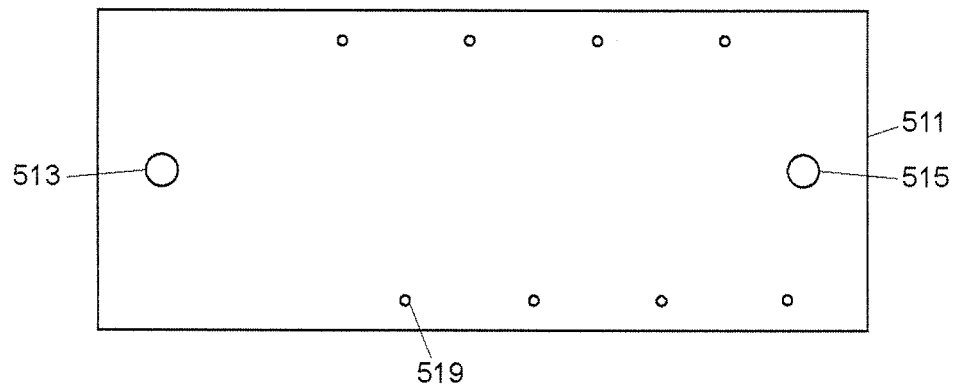
FIG. 31B is a plan view of a cover substrate of the dispensing device according to the embodiment.
Figure 31C:
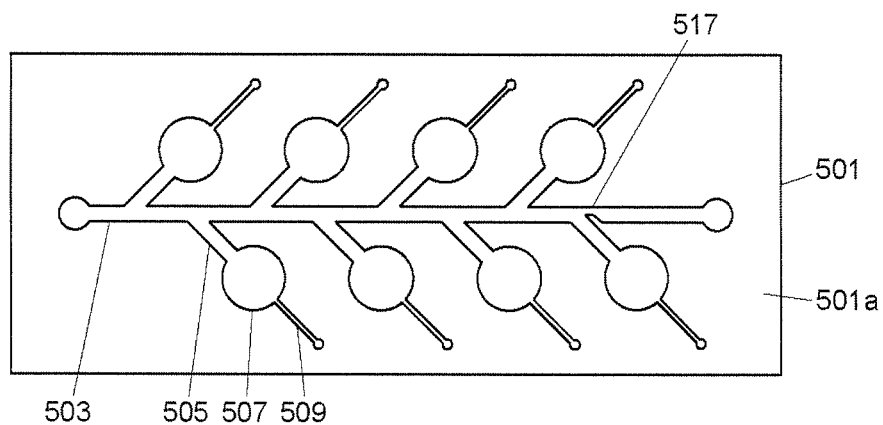
FIG. 31C is a plan view of a base substrate of the dispensing device according to the embodiment.
Figure 31D:
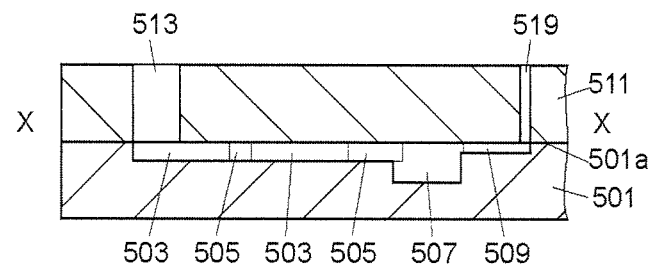
FIG. 31D is a sectional view taken along the X-X line of FIG. 31A.

FIGS. 31A, 31B, 31C, and 31D are drawings showing the structure of a dispensing device according to another embodiment of the present invention, wherein FIG. 31A is a plan view of the dispensing device, FIG. 31B is a plan view of a cover substrate, FIG. 31C is a plan view of a base substrate, and FIG. 31D is a sectional view taken along the X-X line of FIG. 31A.

One surface 501a of a base substrate 501 has a groove for forming a main channel 503 and a plurality of branch channels 505 which constitute a liquid sample introduction channel, recesses for forming a plurality of liquid reservoirs 507, and grooves for forming a plurality of air vent channels 509. The surface 501a of the base substrate 501 is bonded to a cover substrate 511. The main channel 503, the branch channels 505, the liquid reservoirs 507, and the air vent channels 509 are formed by covering, with the cover substrate 511, the grooves and recesses provided in the surface 501a of the base substrate 501.

The cover substrate 511 has a sample inlet 513 provided at a position corresponding to one end of the main channel 503. The sample inlet 513 is constituted of a through hole. The cover substrate 511 also has a sample outlet 515 provided at a position corresponding to the other end of the main channel 503. The sample outlet 515 is also constituted of a through hole.

The branch channels 505 are connected to the main channel 503 between the sample inlet 513 and the sample outlet 515. The number of the branch channels 505 is the same as that of the liquid reservoirs 507. The branch channels 505 are each also connected to the different liquid reservoirs 507 at their ends located on the opposite side from the main channel 503.

In the main channel 503, a third high inflow-withstanding pressure section 517 is provided between the branch channel 505 and the sample outlet 515. The third high inflow-withstanding pressure section 517 has a shorter cross-sectional circumference than the branch channel 505, and therefore, has a higher inflow-withstanding pressure than the branch channel 505.

The air vent channel 509 is also connected to the liquid reservoir 507 at a position different from a position where the branch channel 505 is connected to the liquid reservoir 507. The air vent channel 509 has a shorter cross-sectional circumference than the third high inflow-withstanding pressure section 517, and therefore, has a higher inflow-withstanding pressure than the third high inflow-withstanding pressure section 517. The cover substrate 511 has a plurality of air outlets 519 provided at positions corresponding to the ends of the air vent channels 509 located on the opposite side from the liquid reservoirs 507. The air outlet 519 is constituted of a through hole.

The materials of the base substrate 501 and the cover substrate 511 are not particularly limited, but are preferably cheaply available when the dispensing device is designed to be disposable. Examples of the material of the base substrate 501 include polydimethylsiloxane (PDMS) and silicone rubber. Examples of the material of the cover substrate 511 include resin materials such as polypropylene and polycarbonate.

The design examples of the main channel 503, the branch channel 505, the air vent channel 509, and the third high inflow-withstanding pressure section 517 are as follows. The depth of the main channel 503, the branch channel 505, and the third high inflow-withstanding pressure section 517 is 500 µm. The width of the main channel 503 and the branch channel 505 is 500 µm. The width of the third high inflow-withstanding pressure section 517 is 200 µm. The depth and width of the air vent channel 509 are both 10 µm.

The base substrate 501 can be formed by, for example, molding PDMS using a silicon mold obtained by dry etching.

When the base substrate 501 is formed by molding PDMS ("SYLGARD 184" manufactured by Dow Corning), the contact angle of deionized water as a liquid sample on a channel inner wall is about 108°, and when the cover substrate 511 is made of polypropylene, the contact angle of deionized water as a liquid sample on a channel inner wall is about 95°. When the dispensing device is produced based on the above design examples, a pressure induced by the negative capillary force of the branch channel 505 is about −148 Pa, and a pressure induced by the negative capillary force of the third high inflow-withstanding pressure section 517 is about −283 Pa. By making the cross-sectional circumference of the third high inflow-withstanding pressure section 517 shorter than that of the branch channel 505, it is possible to make the inflow-withstanding pressure of the third high inflow-withstanding pressure section 517 higher than that of the branch channel 505.

FIGS. 32A, 32B, 32C, and 32D are schematic plan views showing how a liquid sample is introduced into the liquid reservoirs 507. In these plan views, a fine dot pattern indicates a liquid sample, a solid arrow indicates the flow of a liquid sample, and an open arrow indicates the flow of air. Hereinbelow, a series of steps in the process of introducing a liquid sample into the liquid reservoirs 7 will be described with reference to FIGS. 32A to 32D.

Figure 32A:
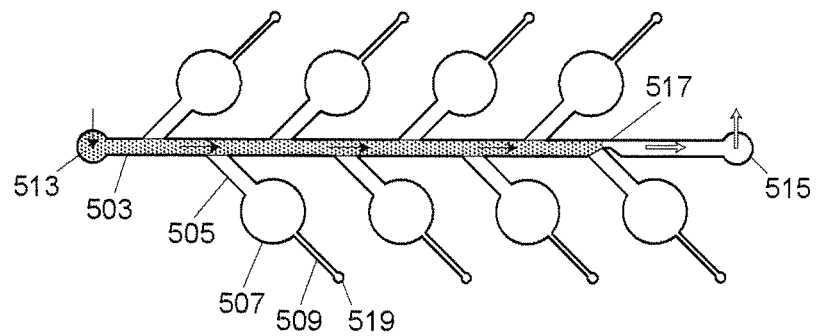
FIG. 32A is a schematic plan view of the entire dispensing device according to the embodiment, which shows the first step in the process of introducing a liquid sample into liquid reservoirs.

First, referring to FIG. 32A, a description will be given. A liquid sample is introduced into the main channel 503 through the sample inlet 513.

The liquid sample introduced into the main channel 3 reaches a branch point between the first branch channel 505 and the main channel 503. Here, the branch channel 505 is connected to the air vent channel 509 through the liquid reservoir 507, and the third high inflow-withstanding pressure section 517 is provided on the downstream side of the main channel 503. Further, the liquid sample that has reached the branch point between the main channel 503 and the branch channel 503 is more likely to flow downstream through the main channel 503 than to flow into the branch channel 505 because the air vent channel 509 has a higher inflow-withstanding pressure than the third high inflow-withstanding pressure section 517. Therefore, the liquid sample flows through the main channel 503 and then reaches the third high inflow-withstanding pressure section 517 provided on the downstream side of the main channel 503.

Figure 32B:
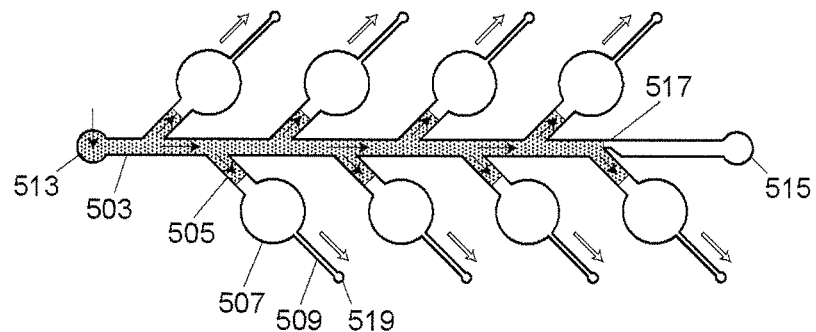
FIG. 32B is a schematic plan view of the entire dispensing device according to the embodiment, which shows a step following the step shown in FIG. 32A in the process of introducing a liquid sample into liquid reservoirs.

Next, referring to FIG. 32B, a description will be given. After the front end of the liquid sample introduced into the main channel 503 reaches the third high inflow-withstanding pressure section 517, the liquid sample flows from the main channel 503 into the plurality of branch channels 505 at the same time because the third high inflow-withstanding pressure section 517 has a higher inflow-withstanding pressure than the branch channel 505.

Figure 32C:
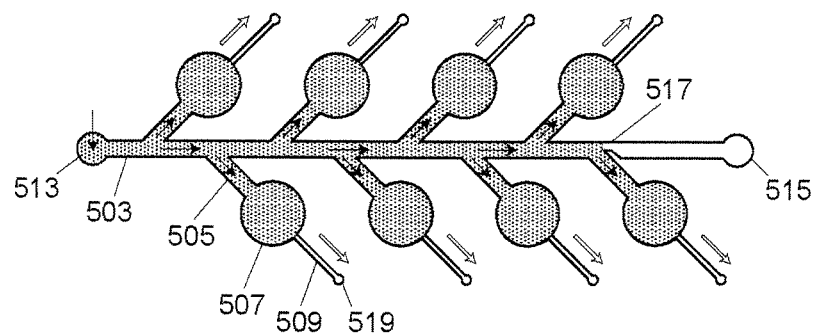
FIG. 32C is a schematic plan view of the entire dispensing device according to the embodiment, which shows a step following the step shown in FIG. 32B in the process of introducing a liquid sample into liquid reservoirs.

Next, referring to FIG. 32C, a description will be given. Each of the liquid reservoirs 507 is filled with the liquid sample. Since the liquid sample flows into the multiple branch channels 505 at the same time, the flow rate of the liquid sample in each of the branch channels 505 and each of the liquid reservoirs 507 is lower than that of the liquid sample introduced into the main channel 503 through the sample inlet 513. When the liquid sample flows into the branch channel 505 and the liquid reservoir 507, a gas contained in the liquid reservoir 507 is discharged through the air vent channel 509. This makes it possible to prevent the formation of gas bubbles in the liquid reservoir 507 after the liquid reservoir 507 is filled with the liquid sample, thereby making it possible to reliably fill the liquid reservoir 507 with a predetermined volume of the liquid sample. At this time, it is preferred that the liquid sample does not flow downstream from the third high inflow-withstanding pressure section 517. However, the liquid sample may flow downstream from the third high inflow-withstanding pressure section 517 as long as the amount of the liquid sample flowing downstream from the third high inflow-withstanding pressure section 517 is smaller than that of the liquid sample flowing into the branch channel 505.

Figure 32D:
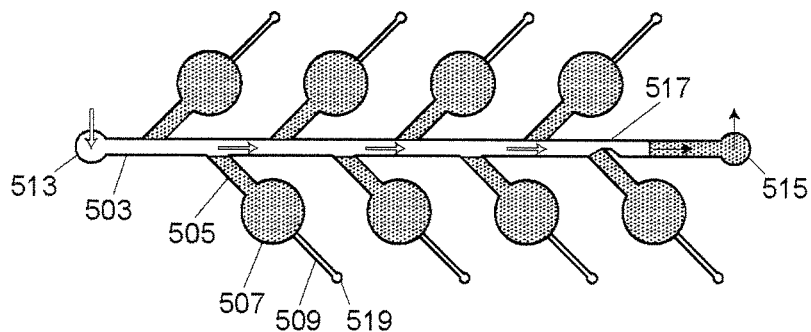
FIG. 32D is a schematic plan view of the entire dispensing device according to the embodiment, which shows a step following the step shown in FIG. 32C in the process of introducing a liquid sample into liquid reservoirs.

Next, referring to FIG. 32D, a description will be given. After all the branch channels 505 and liquid reservoirs 507 are filled with the liquid sample, air is introduced into the main channel 503 through the sample inlet 513 instead of the liquid sample. Introduction of air into the main channel 503 allows the liquid sample present in the main channel 503 to pass through the third high inflow-withstanding pressure section 517 and to be discharged through the sample outlet 515 because the inflow-withstanding pressure of the air vent channel 509 is higher than that of the third high inflow-withstanding pressure section 517.

This dispensing device is capable of reducing the dead volume of a liquid sample as compared to a conventional dispensing because the channel configuration of this dispensing device is simpler than a conventional complicated flow configuration.

Further, this dispensing device is capable of making the flow rate of a liquid sample in the branch channel 505 and the liquid reservoir 507 lower than that of the liquid sample introduced into the main channel 503 through the sample inlet 513. Therefore, for example, in a case where the flow rate of a liquid sample introduced into the main channel 503 through the sample inlet 503 is the same in both the structure of this dispensing device and a structure in which the liquid sample is introduced into the branch channel 507 at the same flow rate as in the main channel 503, the former is capable of making the flow rate of the liquid sample in the branch channel 505 and the liquid reservoir 507 lower as compared to the latter. This makes it possible to stabilize the flow of a liquid sample in the liquid reservoir 507, thereby making it possible to fill the liquid reservoir 507 with the liquid sample without trapping gas bubbles in the liquid reservoir 507. This effect becomes particularly pronounced when a large number of liquid reservoirs are integrates into the dispensing device.

Further, since this dispensing device is capable of introducing a liquid sample into the plurality of branch channels 505 and liquid reservoirs 507 at the same time, the flow rate of the liquid sample introduced into the main channel 503 through the sample inlet 513 can be increased as long as the flow rate of the liquid sample in the branch channel 505 and the liquid reservoir 507 does not become so high that gas bubbles are formed in the liquid reservoir 507. This makes it possible to shorten the time required to fill the plurality of liquid reservoirs 507 with a liquid sample as compared to a case where the plurality of liquid reservoirs 507 are filled with a liquid sample one after another.

Embodiment 8

Figure 33:
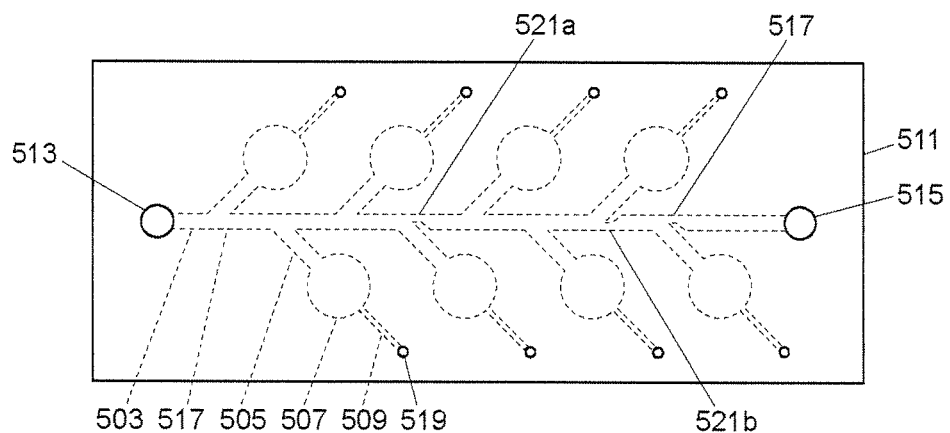
FIG. 33 is a plan view showing the structure of a dispensing device according to another embodiment of the present invention.

FIG. 33 is a plan view showing the structure of a dispensing device according to another embodiment of the present invention. This embodiment has a structure similar to that of the embodiment shown in FIG. 31A.

This embodiment is different from the embodiment shown in FIG. 31A in that, when the dispensing device is seen from the sample inlet 513 side, a fourth high inflow-withstanding pressure section 521a is provided between the fourth branch channel 505 and the fifth branch channel 505. Further, this embodiment is different from the embodiment shown in FIG.

31A also in that, when the dispensing device is seen from the sample inlet 513 side, a fourth high inflow-withstanding pressure section 521b is provided between the seventh branch channel 505 and the eighth branch channel 505, that is, between the two most downstream branch channels 505 and 505.

The fourth high inflow-withstanding pressure sections 521a and 521b have the same size as, for example, the third high inflow-withstanding pressure section 517, and therefore have a higher inflow-withstanding pressure than the main channel 503.

FIGS. 34A, 34B, 34C, and 34D are schematic plan views showing how a liquid sample is introduced into the liquid reservoirs 507. In these plan views, a fine dot pattern indicates a liquid sample, a solid arrow indicates the flow of a liquid sample, and an open arrow indicates the flow of air. Hereinbelow, a series of steps in the process of introducing a liquid sample into the liquid reservoirs 7 will be described with reference to FIGS. 34A to 34D.

Figure 34A:
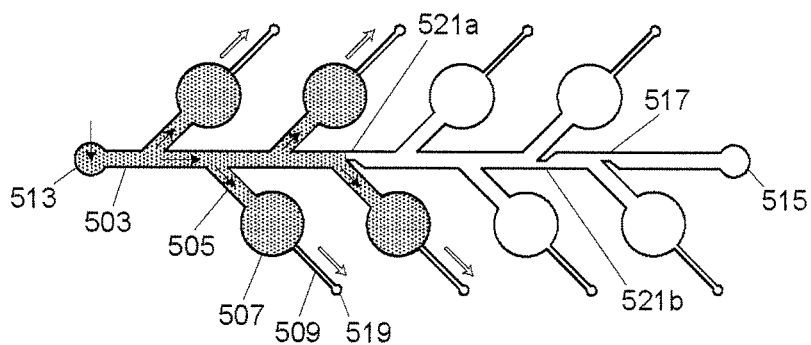
FIG. 34A is a schematic plan view of the entire dispensing device according to the embodiment, which shows the first step in the process of introducing a liquid sample into liquid reservoirs.

First, referring to FIG. 34A, description will be given. A liquid sample is introduced into the main channel 503 through the sample inlet 513.

The liquid sample introduced into the main channel 3 flows through the main channel 503 and reaches the fourth high inflow-withstanding pressure section 521a in the same manner as in the step described above with reference to FIG. 32A. After the front end of the liquid sample reaches the fourth high inflow-withstanding pressure section 521a, the liquid sample flows from the main channel 503 into the plurality of branch channels 505 at the same time in the same manner as in the step described above with reference to FIG. 32B.

Figure 34B:
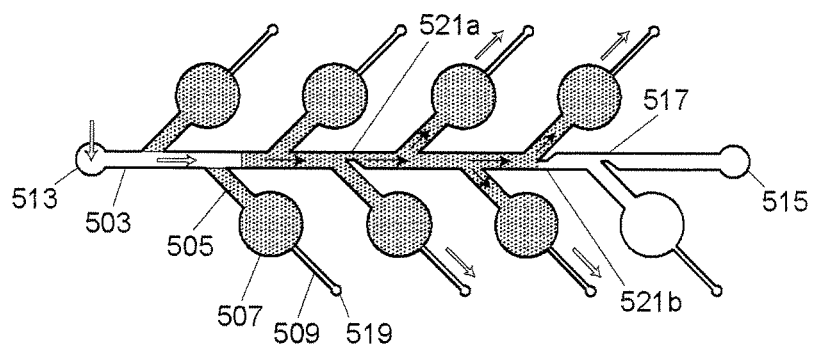
FIG. 34B is a schematic plan view of the entire dispensing device according to the embodiment, which shows a step following the step shown in FIG. 34A in the process of introducing a liquid sample into liquid reservoirs.

Then, referring to FIG. 34B, description will be given. Even after the liquid reservoirs 507 located upstream from the fourth high inflow-withstanding pressure section 521a are filled with the liquid sample, the liquid sample is still introduced into the main channel 503 through the sample inlet 513. The liquid sample present in the main channel 503 passes through the fourth high inflow-withstanding pressure section 521a, flows through the main channel 503, and then reaches the fourth high inflow-withstanding pressure section 521b because the inflow-withstanding pressure of the air vent channel 509 is higher than that of the fourth high inflow-withstanding pressure section 521a. After the front end of the liquid sample reaches the fourth high inflow-withstanding pressure section 521b, the liquid sample flows from the main channel 503 into the multiple branch channels 505 at the same time. At this time, after the liquid sample is introduced into the main channel 503 in an amount at least equal to the total volume of all the branch channels 505 and liquid reservoirs 507 (e.g., after the liquid sample is introduced into the main channel 503 in an amount slightly larger than the total volume of all the branch channel 505 and liquid reservoirs 507), air is introduced into the main channel 503 through the sample inlet 513 instead of the liquid sample.

Figure 34C:
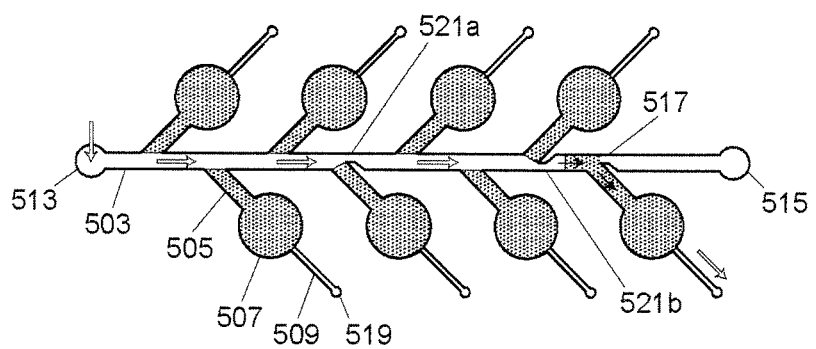
FIG. 34C is a schematic plan view of the entire dispensing device according to the embodiment, which shows a step following the step shown in FIG. 34B in the process of introducing a liquid sample into liquid reservoirs.

Next, referring to FIG. 34C, description will be given. Even after the liquid reservoirs 507 located upstream from the fourth high inflow-withstanding pressure section 521b are filled with the liquid sample, air is still introduced into the main channel 503 through the sample inlet 513. The liquid sample present in the main channel 503 passes through the fourth high inflow-withstanding pressure section 521b, flows through the main channel 503, and then reaches the third high inflow-withstanding pressure section 517 because the inflow-withstanding pressure of the air vent channel 509 is higher than that of the fourth high inflow-withstanding pressure section 521b. After the front end of the liquid sample reaches the third high inflow-withstanding pressure section 517, the liquid sample flows from the main channel 503 into the most downstream branch channel 505 so that the most downstream branch channel 505 is filled with the liquid sample.

Figure 34D:
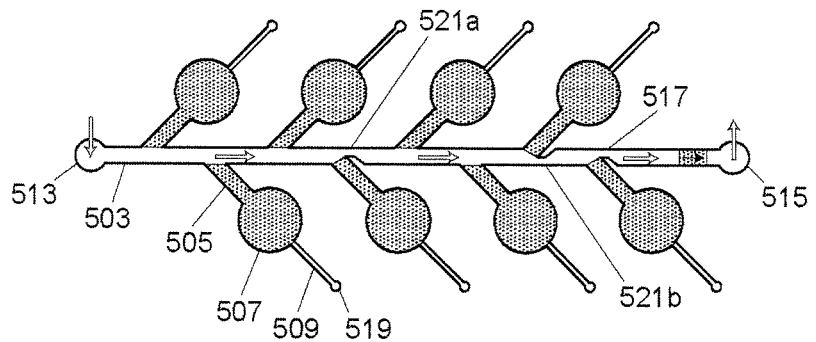
FIG. 34D is a schematic plan view of the entire dispensing device according to the embodiment, which shows a step following the step shown in FIG. 34C in the process of introducing a liquid sample into liquid reservoirs.

Then, referring to FIG. 34D, description will be given. Even after all the branch channels 505 and liquid reservoirs 507 are filled with the liquid sample, air is still introduced into the main channel 503 through the sample inlet 513. The introduction of air into the main channel 503 allows the liquid sample present in the main channel 503 to pass through the third high inflow-withstanding pressure section 517 and to be discharged through the sample outlet 515 because the inflow-withstanding pressure of the air vent channel 509 is higher than that of the third high inflow-withstanding pressure section 517.

This dispensing device is capable of further reducing the dead volume of a liquid sample as compared to the embodiment shown in FIG. 31A.

According to this embodiment, the main channel 503 has two fourth high inflow-withstanding pressure sections 521a and 521b, but the position of the fourth high inflow-withstanding pressure section is not particularly limited as long as it is provided between the branch channels 505 and 505, and the number of the fourth high inflow-withstanding pressure sections is not particularly limited either.

For example, only the fourth high inflow-withstanding pressure section 521b may be provided between the two most downstream branch channels 505 and 505 without providing the fourth high inflow-withstanding pressure section 521a. Also in this case, the dead volume of a liquid sample can be minimized as in the case described above with reference to FIGS. 34A to 34D.

Alternatively, only the fourth high inflow-withstanding pressure section 521a may be provided without providing the fourth high inflow-withstanding pressure section 521b. In this case, a liquid sample needs to be present in the main channel 503 between the third high inflow-withstanding pressure section 517 and the branch point between the main channel 503 and the branch channel 505, which is closest to the fourth high inflow-withstanding pressure section 521a but is located downstream from the fourth high inflow-withstanding pressure section 521a, in order to fill, with the liquid sample, the branch channels 505 and the liquid reservoirs 507 provided between the fourth high inflow-withstanding pressure section 521a and the third high inflow withstanding pressure section 517, and therefore, the dead volume of the liquid sample is at least equal to the capacity of a part of the main channel 503 between the third high inflow-withstanding pressure section 517 and the branch point between the main channel 503 and the branch channel 505 which is closest to the fourth high inflow-withstanding pressure section 521a but is located downstream from the fourth high inflow-withstanding pressure section 521a. However, such a structure is also capable of further reducing the dead volume of a liquid sample as compared to the embodiment shown in FIG. 31A.

As described above, the main channel 503, the branch channels 505, the liquid reservoirs 507, and the air vent channels 509 of each of the embodiments shown in FIGS. 31A and 33 are constituted of grooves and recesses provided in the base substrate 501, but grooves and recesses for forming the main channel, the branch channels, the liquid reservoirs, and the air vent channels may be provided in the cover substrate or in both the base substrate and the cover substrate.

Further, in the embodiments shown in FIGS. 31A and 33, the third high inflow-withstanding pressure section 517, the fourth high inflow-withstanding pressure section 521a, and the fourth high inflow-withstanding pressure section 521b may have the same width and depth as the main channel 503 as in the case of the high inflow-withstanding pressure section 217 shown in FIG. 21A. In this case, the inflow-withstanding pressure of the third high inflow-withstanding pressure section 517 is made higher than that of the branch channel 505 by, for example, subjecting at least part of the inner wall of the third high inflow-withstanding pressure section 517 to surface treatment to increase the contact angle of a sample solution.

Further, the number of continuous and flat inner wall surfaces at the connection between the main channel 503 and the third high inflow-withstanding pressure section 517, or between the main channel 503 and the fourth high inflow-withstanding pressure section 521a, or between the main channel 503 and the fourth high inflow-withstanding pressure section 521b may be two as in the case of the connection between the main channel 303 and the high inflow-withstanding pressure section 317 shown in FIG. 22A (i.e., top and bottom inner wall surfaces), or may be one as in the case of the connection between the main channel 303 and the high inflow-withstanding pressure section 317 shown in FIG. 23 (i.e., only top inner wall surface), or may be zero as in the case of the connection between the main channel 303 and the high inflow-withstanding pressure section 317 shown in FIG. 24.

Embodiment 9

Figure 35A:
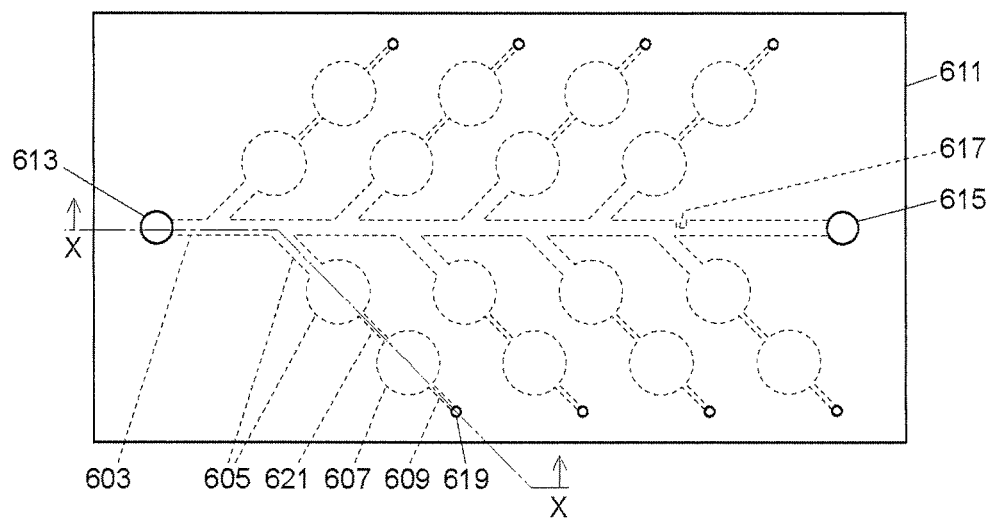
FIG. 35A is a plan view showing the structure of a dispensing device according to another embodiment of the present invention.
Figure 35B:
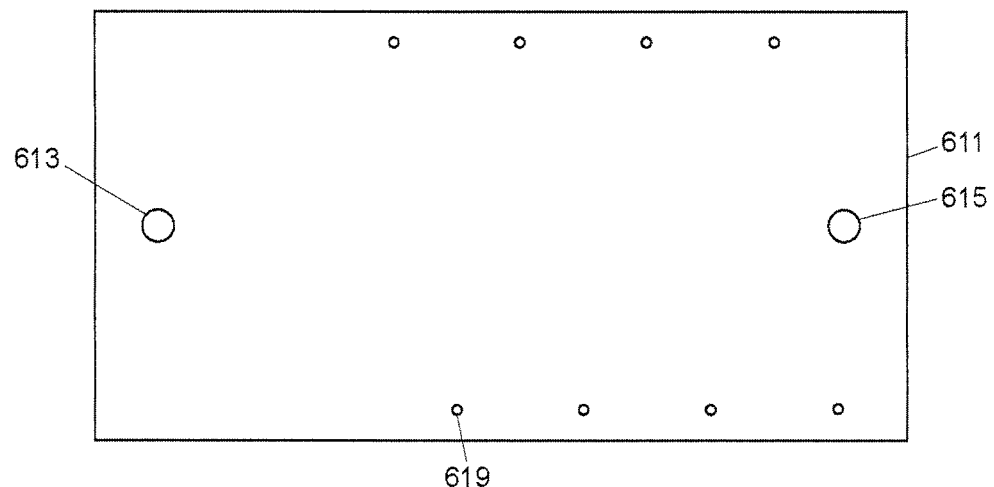
FIG. 35B is a plan view of a cover substrate of the dispensing device according to the embodiment.
Figure 35C:
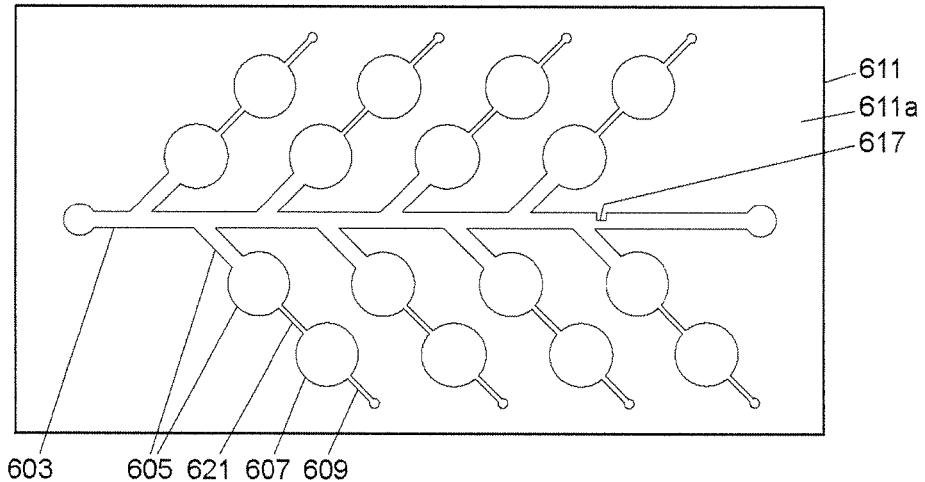
FIG. 35C is a plan view of a base substrate of the dispensing device according to the embodiment.
Figure 35D:
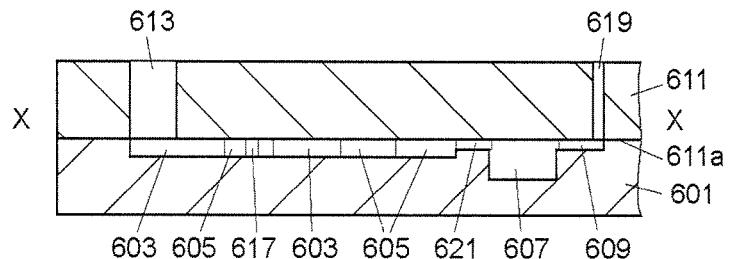
FIG. 35D is a sectional view taken along the X-X line of FIG. 35A.

FIGS. 35A, 35B, 35C, and 35D are drawings showing the structure of a dispensing device according to another embodiment of the present invention, wherein FIG. 35A is a plan view of the dispensing device, FIG. 35B is a plan view of a cover substrate, FIG. 35C is a plan view of a base substrate, and FIG. 35D is a sectional view taken along the X-X line of FIG. 35A.

One surface 601a of a base substrate 601 has a groove for forming a main channel 603, a plurality of metering channels 605, and a plurality of injection channels 621 which constitute a liquid sample introduction channel, recesses for forming a plurality of liquid reservoirs 607, and grooves for forming a plurality of air vent channels 609. The surface 601a of the base substrate 601 is bonded to a cover substrate 611. The main channel 603, the metering channels 605, the injection channels 621, the liquid reservoirs 607, and the air vent channels 609 are formed by covering, with the cover substrate 611, the grooves and recesses provided in the surface 601a of the base substrate 601.

The cover substrate 611 has a sample inlet 613 provided at a position corresponding to one end of the main channel 603. The sample inlet 613 is constituted of a through hole. The cover substrate 611 also has a sample outlet 615 provided at a position corresponding to the other end of the main channel 603. The sample outlet 615 is also constituted of a through hole.

The metering channels 605 are connected to the main channel 603 between the sample inlet 613 and the sample outlet 615. The number of the metering channels 605 is the same as that of the liquid reservoirs 607. The metering channels 605 are connected through the injection channels 621 to the different liquid reservoirs 607 respectively at their ends located on the opposite side from the main channel 603. The injection channel 621 has an inner wall surface forming a contact angle of 90° or larger with a liquid sample, and has a higher inflow-withstanding pressure than a third high inflow-withstanding pressure section 617 (which will be described later). The injection channel 621 does not allow the passage of a liquid sample at a liquid sample introduction pressure applied to introduce the liquid sample into the main channel 603 and the metering channels 605 and at a purge pressure applied to purge the liquid sample from the main channel 603 but allows the passage of the liquid sample at a pressure higher than the liquid sample introduction pressure and the purge pressure.

In the main channel 603, the third high inflow-withstanding pressure section 617 is provided between the metering channel 605 and the sample outlet 615. The third high inflow-withstanding pressure section 617 has a shorter cross-sectional circumference than the metering channel 605, and therefore has a higher inflow-withstanding pressure than the metering channel 605.

The air vent channel 609 is also connected to the liquid reservoir 607 at a position different from a position where the metering channel 605 is connected to the liquid reservoir 607. The cover substrate 611 has a plurality of air outlets 619 provided at positions corresponding to the ends of the air vent channels 609 located on the opposite side from the liquid reservoirs 607. The air outlet 619 is constituted of a through hole.

The design examples of the main channel 603, the metering channel 605, the injection channel 621, the air vent channel 609, the third high inflow-withstanding pressure section 617, and a second high inflow-withstanding pressure section 623 are as follows. The depth of the main channel 603, the metering channel 605, and the high inflow-withstanding pressure section 617 is 500 μm. The width of the main channel 603 is 500 μm. The length and width of the metering channel 605 are set so that the metering channel 605 can contain a predetermined amount of a liquid sample. The depth and width of the injection channel 621 are both 10 μm. The width of the high inflow-withstanding pressure section 617 is 200 μm. The depth and width of the air vent channel 609 are both 10 μm.

When the base substrate 601 is formed by molding PDMS ("SYLGARD184" manufactured by Dow Corning), the contact angle of deionized water as a liquid sample on a channel inner wall is about 108°, and when the cover substrate 611 is made of polypropylene, the contact angle of deionized water as a liquid sample on a channel inner wall is about 95°.

When the dispensing device is produced based on the above design examples so that the width of the narrowest part of the metering channel becomes, for example, 500 μm, a pressure induced by the negative capillary force of the metering channel 605 is about −148 Pa, a pressure induced by the negative capillary force of the high inflow-withstanding pressure section 617 is about −283 Pa, and the injection channel 621 has an inflow-withstanding pressure of about 7383 Pa. Therefore, the metering channel 605 can be filled with a liquid sample by feeding the liquid sample at a liquid feed pressure equal to or less than the inflow-withstanding pressure of the injection channel 621. Further, purging of a liquid sample from the main channel 603 can be performed by feeding a gas into the main channel 603 at a pressure similar to the liquid feed pressure.

FIGS. 36A, 36B, 36C, and 36D are schematic plan views showing how a liquid sample is introduced into the liquid reservoirs 607. In these plan views, a fine dot pattern indicates a liquid sample, a solid arrow indicates the flow of a liquid sample, and an open arrow indicates the flow of air. Hereinbelow, a series of steps in the process of introducing a liquid sample into the liquid reservoirs 607 will be described with reference to FIGS. 36A to 36D.

Figure 36A:
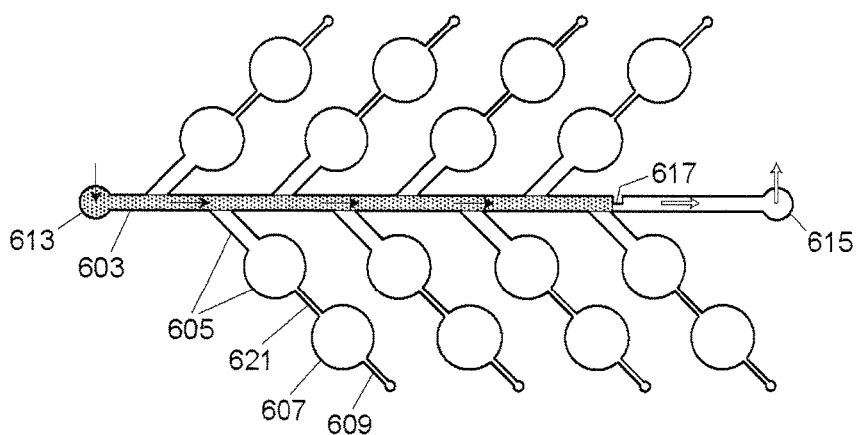
FIG. 36A is a schematic plan view of the entire dispensing device according to the embodiment, which shows the first step in the process of introducing a liquid sample into liquid reservoirs.

First, referring to FIG. 36A, a description will be given. A liquid sample is introduced into the main channel 603 through the sample inlet 613. Then, the liquid sample introduced into the main channel 603 reaches a branch point between the first metering channel 605 and the main channel 603. Here, the metering channel 605 is connected to the injection channel 621, and the third high inflow-withstanding pressure section 617 is provided on the downstream side of the main channel 603. Further, the liquid sample that has reached the branch point between the main channel 603 and the injection channel 621 flows through the main channel 603 and then reaches the third high inflow-withstanding pressure section 617 provided on the downstream side of the main channel 603. This is because the injection channel 621 has a higher inflow-withstanding pressure than the third high inflow-withstanding pressure section 617, and therefore, the liquid sample that has reached the branch point between the main channel 603 and the injection channel 621 is more likely to flow downstream through the main channel 603 than to flow into the injection channel 621.

Figure 36B:
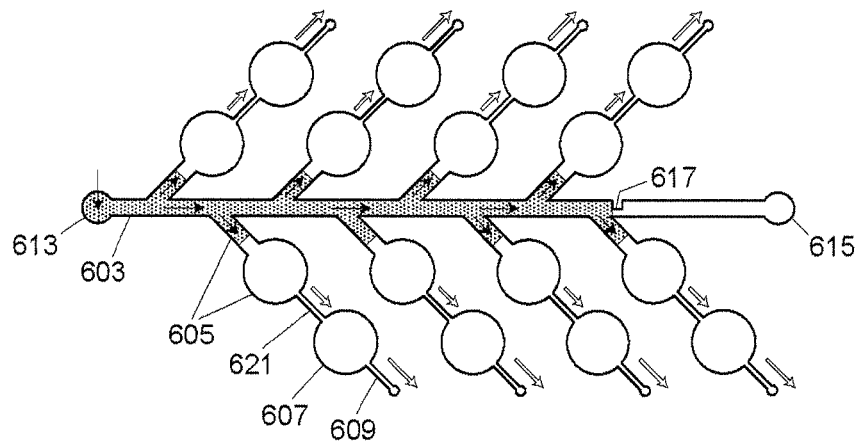
FIG. 36B is a schematic plan view of the entire dispensing device according to the embodiment, which shows a step following the step shown in FIG. 36A in the process of introducing a liquid sample into liquid reservoirs.

Next, referring to FIG. 36B, description will be given. After the front end of the liquid sample introduced into the main channel 603 reaches the third high inflow-withstanding pressure section 617, the liquid sample flows from the main channel 603 into the plurality of branch channels 605 at the same time so that each of the metering channels 605 is filled with the liquid sample because the third high inflow-withstanding pressure section 617 has a higher inflow-withstanding pressure than the metering channel 605. Since the liquid sample flows into the plurality of metering channels 605 at the same time, the flow rate of the liquid sample in each of the metering channels 605 is lower than that of the liquid sample introduced into the main channel 603 through the sample inlet 613. When the liquid sample flows into the metering channel 605, a gas contained in the metering channel 605 flows through the injection channel 621 into the liquid reservoir 607, and a gas contained in the liquid reservoir 607 flows through the air vent channel 609 and is discharged through the air outlet 619. This makes it possible to prevent the formation of gas bubbles in the metering channel 605 after the metering channel 605 is filled with the liquid sample, thereby making it possible to reliably fill the metering channel 605 with a predetermined volume of the liquid sample. At this time, it is preferred that the liquid sample does not flow downstream from the third high inflow-withstanding pressure section 617. However, the liquid sample may flow downstream from the third high inflow-withstanding pressure section 617 as long as the amount of the liquid sample flowing downstream from the third high inflow-withstanding pressure section 617 is smaller than that of the liquid sample flowing into the metering channel 605.

Figure 36C:
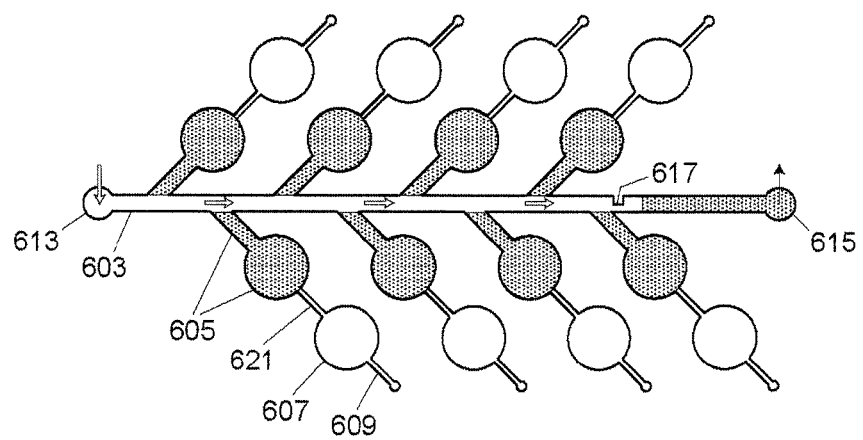
FIG. 36C is a schematic plan view of the entire dispensing device according to the embodiment, which shows a step following the step shown in FIG. 36B in the process of introducing a liquid sample into liquid reservoirs.

Next, referring to FIG. 36C, description will be given. After all the metering channels 605 are filled with the liquid sample, air is introduced into the main channel 603 through the sample inlet 613 instead of the liquid sample. Since the inflow-withstanding pressure of the injection channel 6221 is higher than that of the third high inflow-withstanding pressure section 617, the introduction of air into the main channel 603 allows the liquid sample present in the main channel 603 to pass through the third high inflow-withstanding pressure section 617 and to be discharged through the sample outlet 615.

Figure 36D:
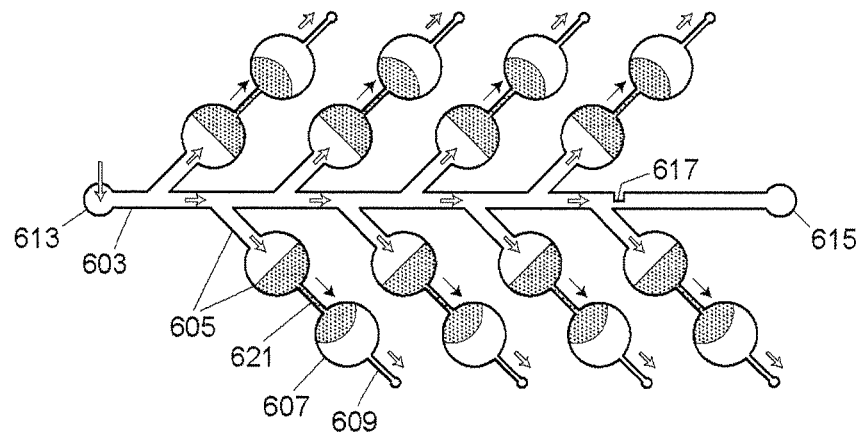
FIG. 36D is a schematic plan view of the entire dispensing device according to the embodiment, which shows a step following the step shown in FIG. 36C in the process of introducing a liquid sample into liquid reservoirs.

Then, referring to FIG. 36D, description will be given. A channel connected to the sample outlet 615 is hermetically sealed and a gas is fed to the main channel 603 from the sample inlet 613 side to apply a pressure higher than the purge pressure to the inside of the main channel 603. This makes it possible to inject the liquid sample contained in the metering channels 605 into the liquid reservoirs 607 through the injection channels 621.

This dispensing device has a channel configuration simpler than a conventional complicated channel configuration, and is therefore capable of reducing the dead volume of a liquid sample as compared to a conventional dispensing device.

Further, this dispensing device is capable of making the flow rate of a liquid sample in the metering channel 605 lower than that of the liquid sample introduced into the main channel 603 through the sample inlet 613. Therefore, for example, in a case where the flow rate of a liquid sample introduced into the main channel 603 through the sample inlet 603 is the same in both the structure of this dispensing device and a structure in which the liquid sample is introduced into the metering channel 605 at the same flow rate as in the main channel 603, the former is capable of making the flow rate of the liquid sample in the metering channel 605 lower as compared to the latter. This makes it possible to stabilize the flow of a liquid sample in the metering channel 605, thereby making it possible to fill the metering channel 605 with the liquid sample without trapping gas bubbles in the metering channel 605. This effect becomes particularly pronounced when a large number of metering channels are integrated into the dispensing device.

Further, since this dispensing device is capable of introducing a liquid sample into the plurality of metering channels 605 at the same time, the flow rate of a liquid sample introduced into the main channel 603 through the sample inlet 613 can be increased as long as the flow rate of the liquid sample in the metering channel 605 does not become so high that gas bubbles are formed in the liquid reservoir. This makes it possible to shorten the time required to fill the plurality of metering channels 605 with a liquid sample as compared to a case where the plurality of metering channels 605 are filled with a liquid sample one after another.

As described above, the main channel 603, the metering channels 605, the injection channels 621, the liquid reservoirs 607, and the air vent channels 609 of this embodiment are constituted of grooves and recesses provided in the base substrate 601, but grooves and recesses for forming the main channel, the metering channels, the injection channels, the liquid reservoirs, and the air vent channels may be provided in the cover substrate or in both the base substrate and the cover substrate.

In the embodiment shown in FIG. 35A, the third high inflow-withstanding pressure section 617 may have the same width and depth as the main channel 603 as in the case of the high inflow-withstanding pressure section 217 shown in FIG. 21A. In this case, at least part of the inner wall of the third high inflow-withstanding pressure section 617 may be subjected to surface treatment to increase the contact angle of a sample solution so that the inflow-withstanding pressure of the third high inflow-withstanding pressure section 617 becomes higher than that of the metering channel 605.

Further, the number of continuous and flat inner wall surfaces at the connection between the main channel 603 and the third high inflow-withstanding pressure section 617 may be two as in the case of the connection between the main channel 303 and the high inflow-withstanding pressure section 317 shown in FIG. 22A (i.e., top and bottom inner wall surfaces), or may be one as in the case of the connection between the main channel 303 and the high inflow-withstanding pressure section 317 shown in FIG. 23 (i.e., only top inner wall surface), or may be zero as in the case of the connection between the main channel 303 and the high inflow-withstanding pressure section 317 shown in FIG. 24.

Embodiment 10

Figure 37:
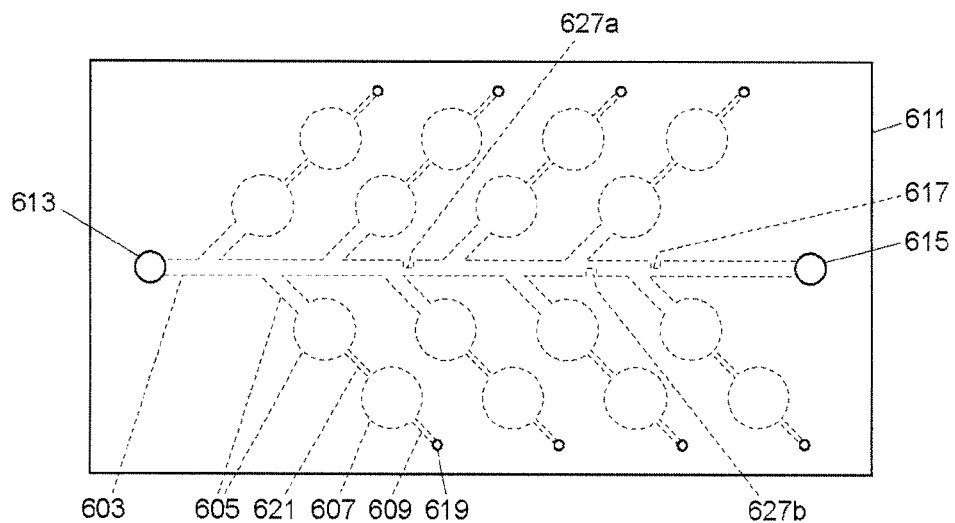
FIG. 37 is a plan view showing the structure of a dispensing device according to another embodiment of the present invention.

FIG. 37 is a plan view showing the structure of a dispensing device according to another embodiment of the present invention. The Structure of this Embodiment is Similar to that of the Embodiment shown in FIG. 35A.

This embodiment is different from the embodiment shown in FIG. 35A in that, when the dispensing device is seen from the sample inlet 613 side, a fourth high inflow-withstanding pressure section 627a is provided between the fourth branch channel 605 and the fifth branch channel 605. Further, this embodiment is different from the embodiment shown in FIG. 35A also in that, when the dispensing device is seen from the sample inlet 513 side, a fourth high inflow-withstanding pressure section 627b is provided between the seventh branch channel 605 and the eighth branch channel 605, that is, between the two most downstream branch channels 605 and 605.

The fourth high inflow-withstanding pressure sections 627a and 627b have the same size as, for example, the third high inflow-withstanding pressure section 617, and therefore, have a higher inflow-withstanding pressure than the main channel 603.

In the case of this embodiment, the metering channels 605 are filled with a liquid sample in the same manner as in the steps described above with reference to FIGS. 34A to 34D in the process of introducing a liquid sample into the liquid reservoirs of the embodiment shown in FIG. 33. More specifically, the metering channels 605 located upstream from the fourth high inflow-withstanding pressure section 627a are first filled with a liquid sample, and then the metering channels 605 located between the fourth high inflow-withstanding pressure section 627a and the fourth high inflow-withstanding pressure section 627b are filled with the liquid sample, and then the metering channel 605 located between the fourth high inflow-withstanding pressure section 627b and the third high inflow-withstanding pressure section 617 is filled with the liquid sample.

This embodiment is also capable of reducing the dead volume of a liquid sample as in the case of the embodiment shown in FIG. 33. It is to be noted that the position of the fourth high inflow-withstanding pressure section is not particularly limited as long as it is provided between the metering channels 605 and 605, and the number of the fourth high inflow-withstanding pressure sections is not particularly limited either.

Embodiment 11

Figure 38A:
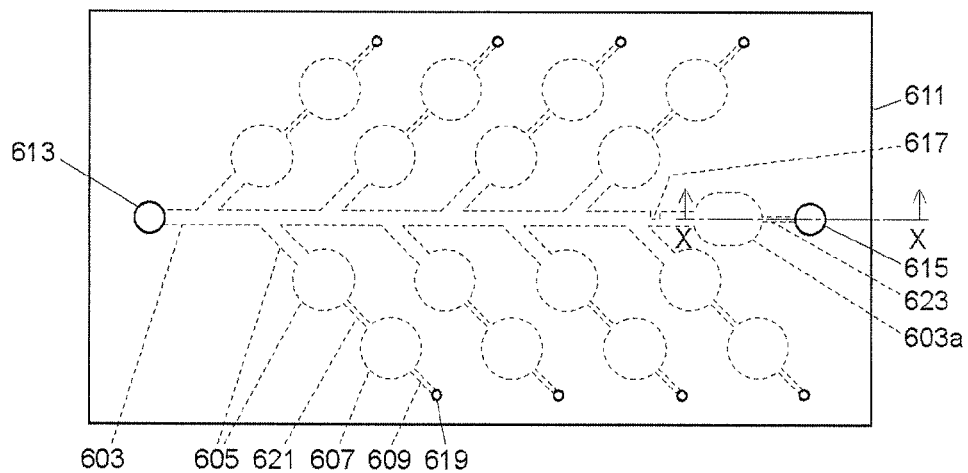
FIG. 38A is a plan view showing the structure of a dispensing device according to another embodiment of the present invention.
Figure 38B:
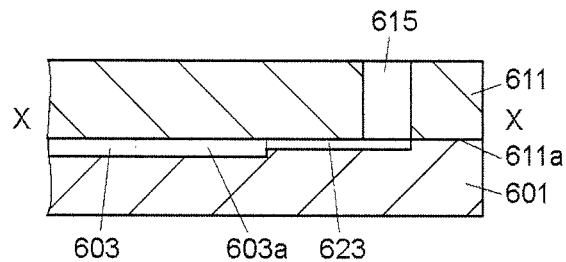
FIG. 38B is a sectional view taken along the X-X line of FIG. 38A.

FIGS. 38A and 38B are drawings showing the structure of a dispensing device according to another embodiment of the present invention, wherein FIG. 38A is a plan view of the dispensing device and FIG. 38B is a sectional view taken along the X-X line of FIG. 38A. The structure of this embodiment is similar to that of the embodiment shown in FIG. 35A.

This embodiment is different from the embodiment shown in FIG. 35A in that a fifth high inflow-withstanding pressure section 623 is provided in the main channel 603 between the third high inflow-withstanding pressure section 617 and the sample outlet 615 so as to be spaced from the third high inflow-withstanding pressure section 617. The fifth high inflow-withstanding pressure section 623 has a shorter cross-sectional circumference than the third high inflow-withstanding pressure section 617, and therefore, has a higher inflow-withstanding pressure than the main channel 603.

Further, a main channel 603a located between the third high inflow-withstanding pressure section 617 and the fifth high inflow-withstanding pressure section 623 has a width larger than that of the other part of the main channel 603. The main channel 603a is designed so as to have a capacity larger than the volume of a liquid sample to be purged from the main channel 603 (dead volume). Here, the capacity of the main channel 603a is made larger than the volume of a liquid sample to be purged from the main channel 603 by making the width of the main channel 603a larger than that of the main channel 603. However, the capacity of a part of the main channel 603 located between the third high inflow-withstanding pressure section 617 and the fifth high inflow-withstanding pressure section 623 may be made larger than the volume of a liquid sample to be purged from the main channel 603 by meandering the part of the main channel 603 located between the third high inflow-withstanding pressure section 617 and the fifth high inflow-withstanding pressure section 623 or by making the depth of the part of the main channel 603 located between the third high inflow-withstanding pressure section 617 and the fifth high inflow-withstanding pressure section 623 larger than that of the main channel 603.

Figure 39A:
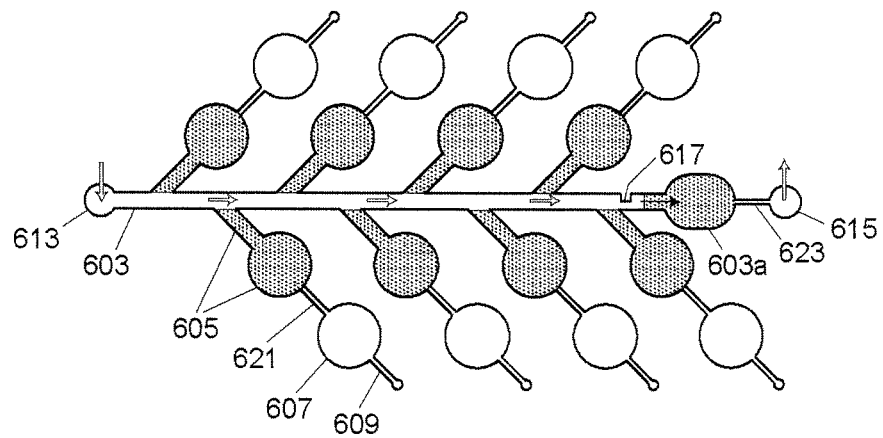
FIG. 39A is a schematic plan view of the entire dispensing device according to the embodiment, which shows one step in the process of introducing a liquid sample into liquid reservoirs.
Figure 39B:
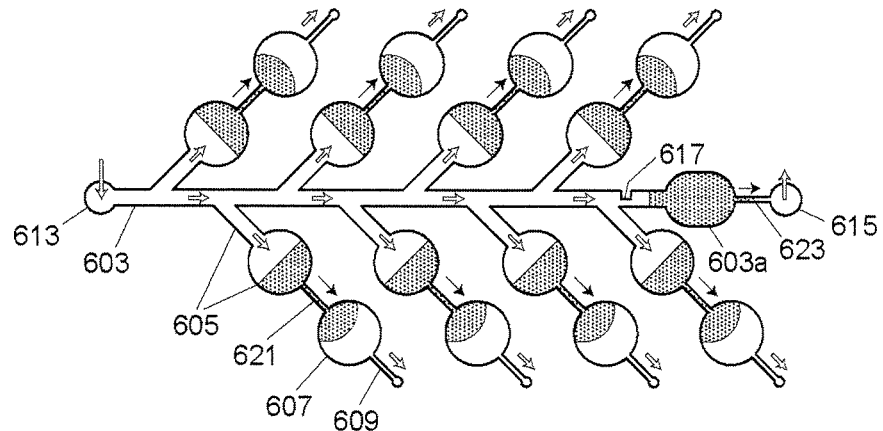
FIG. 39B is a schematic plan view of the entire dispensing device according to the embodiment, which shows a step following the step shown in FIG. 39A in the process of introducing a liquid sample into liquid reservoirs.

FIGS. 39A and 39B are schematic plan views showing how a liquid sample is introduced into the liquid reservoirs 607. In these plan views, a fine dot pattern indicates a liquid sample, a solid arrow indicates the flow of a liquid sample, and an open arrow indicates the flow of air. Hereinbelow, a series of steps in the process of introducing a liquid sample into the liquid reservoirs 607 will be described with reference to FIGS. 39A and 39B.

A liquid sample is introduced into the main channel 603 through the sample inlet 613 and reaches the third high inflow-withstanding pressure section 617, and then the metering channels 605 are filled with the liquid sample in the same manner as in the steps described above with reference to FIGS. 36A and 36B.

After the metering channels 605 are filled with the liquid sample, the liquid sample remaining in the main channel 603 (dead volume) is purged. As shown in FIG. 39A, the liquid sample purged from the main channel 603 passes through the third high inflow-withstanding pressure section 617 and is then contained in the main channel 603a. The front end of the liquid sample contained in the main channel 603a reaches the fifth high inflow-withstanding pressure section 623.

Air is still fed into the main channel 603 from the sample inlet 613 side in a state shown in FIG. 39A by allowing, for example, a system for feeding liquid or gas to continue to be driven at a constant output to increase the pressure in the main channel 603 to apply a pressure higher than the purge pressure to the inside of the main channel 603. As a result, the liquid sample contained in the metering channels 605 is injected into the liquid reservoirs 607 through the injection channels 621. At this time, part or all of the liquid sample whose front end has reached the fifth high inflow-withstanding pressure section 623 may flow into the fifth high inflow-withstanding pressure section 623. However, it is preferred that the liquid sample does not flow into the fifth high inflow-withstanding pressure section 623. After a lapse of predetermined time, injection of the liquid sample into the liquid reservoirs 607 through the injection channels 621 is completed.

As described above, the liquid sample contained in the metering channels 605 can be injected into the liquid reservoirs 607 without hermetically sealing the sample outlet 615 side of the main channel 603 with the use of a switching valve or the like, thereby simplifying the channel configuration of the dispensing device.

Further, feeding of a liquid sample, purging, and injection of a liquid sample into the liquid reservoirs 607 can be performed without changing the driving output of the system for feeding liquid or gas such as a syringe pump. This makes it easy to control the system for feeding liquid or gas. However, the driving outputs of the system for feeding liquid or gas during feeding of a liquid sample, purging, and injection of a liquid sample into the liquid reservoirs may be different from each other.

In the embodiment shown in FIG. 38A, the cross-sectional circumference of the fifth high inflow-withstanding pressure section 623 is made shorter than that of the main channel 603 by making the width and depth of the fifth high inflow-withstanding pressure section 623 shorter than those of the main channel 603. However, the structure of the fifth high inflow-withstanding pressure section 623 is not limited thereto. The structure of the fifth high inflow-withstanding pressure section 623 is not particularly limited as long as it has a higher inflow-withstanding pressure than the third high inflow-withstanding pressure section 617.

For example, the fifth high inflow-withstanding pressure section 623 may be constituted of a plurality of narrow holes having a shorter cross-sectional circumference than the third high inflow-withstanding pressure section 617 as in the case of the second high inflow-withstanding pressure section 423 shown in FIGS. 27A and 27B. Alternatively, the fifth high inflow-withstanding pressure section 623 may be constituted of a plurality of projections as in the case of the second high inflow-withstanding pressure section 423 shown in FIGS. 28A and 28B.

Embodiment 12

Figure 40:
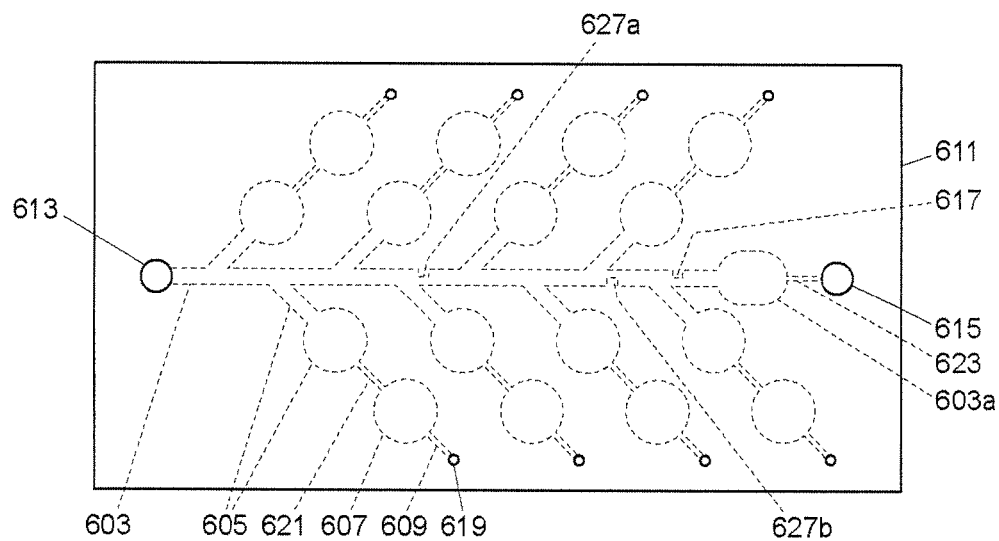
FIG. 40 is a plan view showing the structure of a dispensing device according to another embodiment of the present invention.

FIG. 40 is a plan view showing the structure of a dispensing device according to another embodiment of the present invention. The structure of this embodiment is similar to that of the embodiment shown in FIG. 38A.

This embodiment is different from the embodiment shown in FIG. 38A in that the fourth high inflow-withstanding pressure sections 627a and 627b are provided as in the case of the embodiment shown in FIG. 37.

Also in the case of this embodiment, as in the case of the embodiment shown in FIG. 37, the metering channels 605 located upstream from the fourth high inflow-withstanding pressure section 627a are first filled with a liquid sample, and then the metering channels 605 located between the fourth high inflow-withstanding pressure section 627a and the fourth high inflow-withstanding pressure section 627b are filled with the liquid sample, and then the metering channel 605 located between the fourth high inflow-withstanding pressure section 627b and the third high inflow-withstanding pressure section 617 is filled with the liquid sample. Therefore, as in the case of the embodiment shown in FIG. 33, this embodiment is capable of reducing the dead volume of a liquid sample. It is to be noted that the position of the fourth high inflow-withstanding pressure section is not particularly limited as long as it is provided between the metering channels 605 and 605, and the number of the fourth high inflow-withstanding pressure sections is not particularly limited either.

Embodiment 13

Figure 41A:
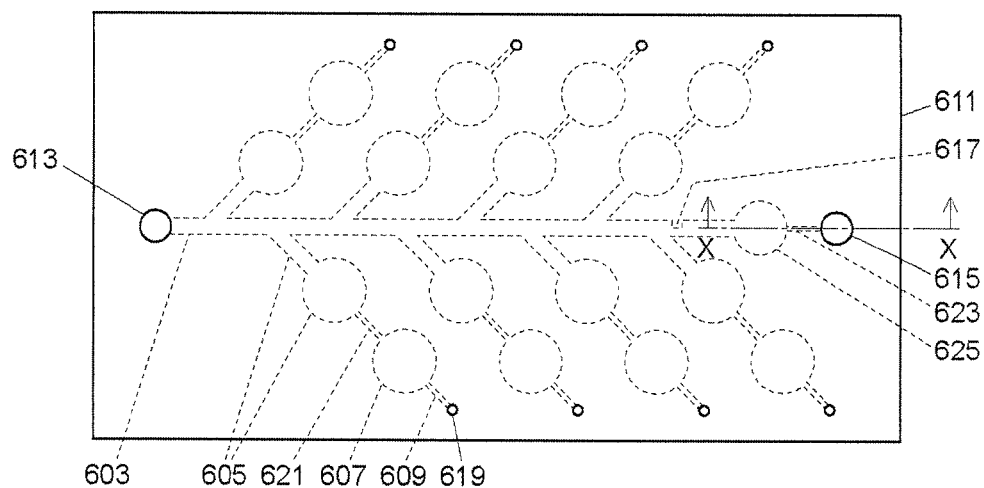
FIG. 41A is a plan view showing the structure of a dispensing device according to another embodiment of the present invention.
Figure 41B:
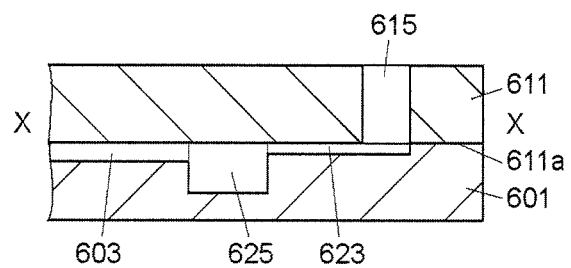
FIG. 41B is a sectional view taken along the X-X line of FIG. 41A.

FIGS. 41A and 41B are drawings showing the structure of a dispensing device according to another embodiment of the present invention, wherein FIG. 41A is a plan view of the dispensing device and FIG. 41B is a sectional view taken along the X-X line of FIG. 41A. The structure of this embodiment is similar to that of the embodiment shown in FIG. 38A.

The structure of this embodiment is the same as that of the embodiment shown in FIG. 38A except that a liquid waste container 625 is provided in the main channel 603 between the third high inflow-withstanding pressure section 617 and the fifth high inflow-withstanding pressure section 423 instead of the main channel 603a having a larger width than the other part of the main channel 603. A design example of the liquid waste container 625 is a cylindrical one having an inner diameter of, for example, 3 mm and a depth of, for example, 10 mm. The fifth high inflow-withstanding pressure section 623 is connected to the liquid waste container 625 so as to be spaced from the bottom of the liquid waste container 625. In this embodiment, the fifth high inflow-withstanding pressure section 623 is connected to the upper edge of the side surface of the liquid waste container 625. This prevents a liquid sample contained in the liquid waste container 625 from coming into contact with the fifth high inflow-withstanding pressure section 623.

Figure 42A:
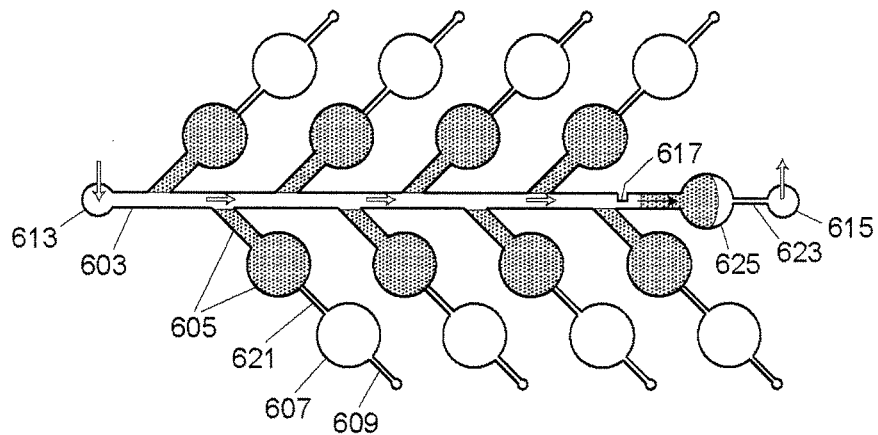
FIG. 42A is a schematic plan view of the entire dispensing device according to the embodiment, which shows one step in the process of introducing a liquid sample into liquid reservoirs.
Figure 42B:
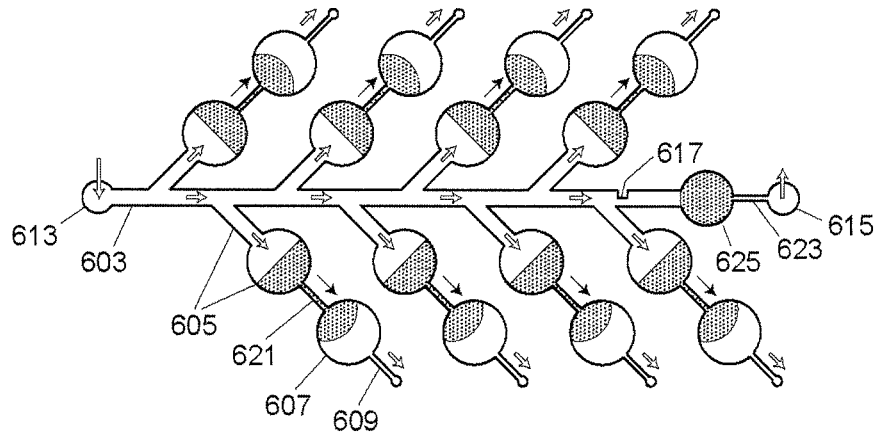
FIG. 42B is a schematic plan view of the entire dispensing device according to the embodiment, which shows a step following the step shown in FIG. 42A in the process of introducing a liquid sample into liquid reservoirs.

FIGS. 42A and 42B are schematic plan views showing how a liquid sample is introduced into the liquid reservoirs 607. In these drawings, a fine dot pattern indicates a liquid sample, a solid arrow indicates the flow of a liquid sample, and an open arrow indicates the flow of air. Hereinbelow, a series of steps in the process of introducing a liquid sample into the liquid reservoirs 607 will be described with reference to FIGS. 42A and 42B.

A liquid sample is introduced into the main channel 603 through the sample inlet 613 and reaches the third high inflow-withstanding pressure section 617, and then the metering channels 605 are filled with the liquid sample in the same manner as in the steps described above with reference to FIGS. 36A and 36B.

After the metering channels 605 are filled with the liquid sample, the liquid sample remaining in the main channel 603 (dead volume) is purged. As shown in FIG. 42A, the liquid sample purged from the main channel 603 passes through the third high inflow-withstanding pressure section 617 and is then contained in the liquid waste container 625. At this time, the liquid sample contained in the liquid waste container 625 does not come into contact with the fifth high inflow-withstanding pressure section 623.

Next, referring to FIG. 42B, the dead volume of the liquid sample is contained in the liquid waste container 625. In this state, air is introduced into the main channel 603 through the sample inlet 613 at a flow rate, which is higher than that used for feeding the liquid sample and that used for feeding air for purging, to increase the pressure in the main channel 403. For example, the flow rate of the liquid sample fed into the main channel 603 and the flow rate of air fed into the main channel 603 for purging are 100 µL/min, and the flow rate of air fed into the main channel 603 to apply a higher pressure to the inside of the main channel 603 is 20000 µL/min. Since the fifth high inflow-withstanding pressure section 623 has a higher inflow-withstanding pressure than the third high inflow-withstanding pressure section 617, the pressure in the main channel 603 can be increased to a level allowing the liquid sample contained in the metering channels 605 to be injected into the liquid reservoirs 607 through the injection channels 621 by feeding air into the main channel 403 at a flow rate higher than that used for purging by increasing the driving output of a system for feeding liquid or gas. As a result, the liquid sample contained in the metering channels 605 is injected into the liquid reservoirs 607 through the injection channels 621.

Also in the case of this embodiment, a liquid sample contained in the metering channels 605 can be injected into the liquid reservoirs 607 without hermetically sealing the sample outlet 615 side of the main channel 603 with the use of a switching valve or the like. This makes it possible to simplify the channel configuration of the dispensing device. Further, a liquid sample is not discharged through the sample outlet 615 but is contained in the liquid waste container 625, thereby reducing concerns about environmental contamination with the liquid sample.

The fifth high inflow-withstanding pressure section of the embodiment shown in FIG. 41A may have the structure described above with reference to FIGS. 27A and 27B or FIGS. 28A and 28B.

Embodiment 14

Figure 43:
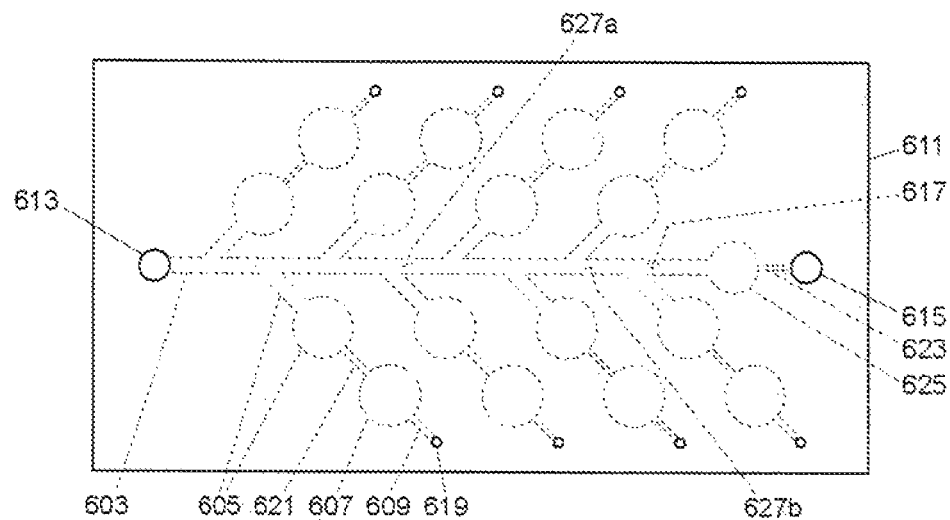
FIG. 43 is a plan view showing the structure of a dispensing device according to another embodiment of the present invention.
Figure 43:
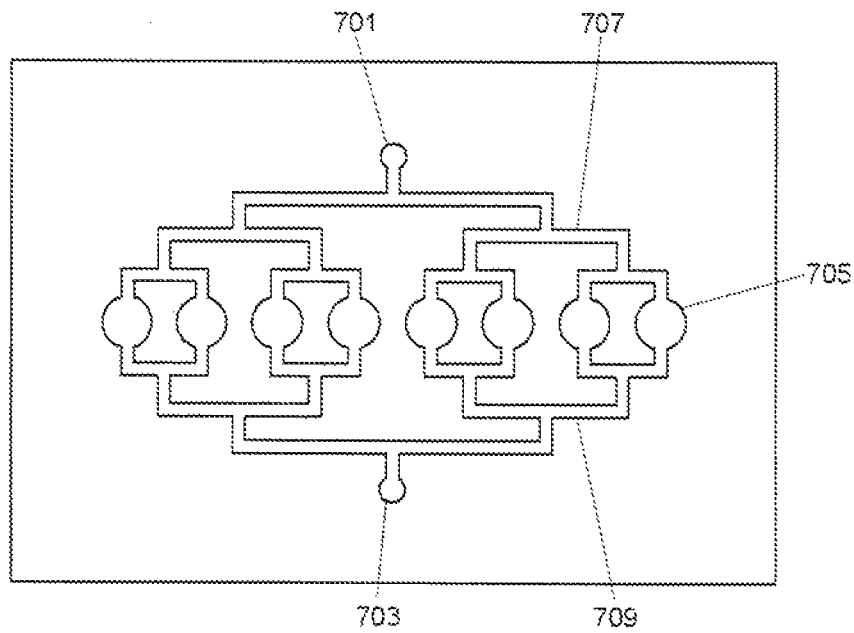

FIG. 43 is a plan view showing the structure of a dispensing device according to another embodiment of the present invention. The structure of this embodiment is similar to that of the embodiment shown in FIG. 41A.

This embodiment is different from the embodiment shown in FIG. 41A in that the fourth high inflow-withstanding pressure sections 627a and 627b are provided as in the case of the embodiment shown in FIG. 37.

Also in the case of this embodiment, as in the case of the embodiment shown in FIG. 37, the metering channels 605 located upstream from the fourth high inflow-withstanding pressure section 627a are first filled with a liquid sample. Next, the metering channels 605 located between the fourth high inflow-withstanding pressure section 627a and the fourth high inflow-withstanding pressure section 627b are filled with the liquid sample. Then the metering channel 605 located between the fourth high inflow-withstanding pressure section 627b and the third high inflow-withstanding pressure section 617 is filled with the liquid sample. Therefore, as in the case of the embodiment shown in FIG. 33, this embodiment is capable of reducing the dead volume of a liquid sample. It is to be noted that the position of the fourth high inflow-withstanding pressure section is not particularly limited as long as it is provided between the metering channels 605 and 605, and the number of the fourth high inflow-withstanding pressure sections is not particularly limited, either.

Although the present invention has been described with reference to the above embodiments, the present invention is not limited thereto. The shape, material, position, number, and size of each component and the channel configuration of each embodiment are merely examples, and various changes may be made without departing from the scope of the present invention defined in the claims.

For example, in the above embodiments, the air vent channel is provided as an air vent port connected to the liquid reservoir, but a hydrophobic porous membrane may be used as such an air vent port instead of the air vent channel. By providing a hydrophobic porous membrane as, for example, a ceiling of the liquid reservoir, it is possible to discharge a gas contained in the liquid reservoir to the outside through the hydrophobic porous membrane when a liquid sample is injected into the liquid reservoir.

Please note, for the purposes of the claims herein below, the high inflow-withstanding pressure sections are numbered consecutively starting with the numeral term "first" and thus do not correspond exactly to the disclosure above. However, such differences between the claim language and the above disclosure can be clearly understood by one skilled in the art in the context of the disclosure.

What is claimed is:

1. A dispensing device comprising:
   a base substrate;
   a cover substrate whose one surface is bonded to one surface of the base substrate;
   a liquid reservoir comprising a recess provided in one or both of the one surface of the base substrate and the one surface of the cover substrate;
   a liquid sample introduction channel comprising a groove provided in one or both of the one surface of the base substrate and the one surface of the cover substrate, the liquid sample introduction channel being connected to the liquid reservoir; and
   an air vent port provided in one or both of the one surface of the base substrate and the one surface of the cover substrate and connected to the liquid reservoir at a position different from a position where the liquid sample introduction channel is connected to the liquid reservoir,
   wherein the number of the liquid reservoirs is two or more,
   the liquid sample introduction channel includes a main channel and a plurality of branch channels, one end of the main channel being connected to a sample inlet and the other end of the main channel being connected to as sample outlet, the branch channels being connected to the main channel between the sample inlet and the sample outlet,
   the branch channels are each connected to the different liquid reservoirs at their ends located on an opposite side from the main channel, and
   first high inflow-withstanding pressure sections having a higher inflow-withstanding pressure than the branch channels are provided in the main channel between the branch channels and between the branch channels and the sample outlet,
   wherein each branch channel includes a metering channel and an injection channel, one end of the metering channel being connected to the main channel and the metering channel having a predetermined capacity, one end of the injection channel being connected to the other end of the metering channel and the other end of the injection channel being connected to the liquid reservoir, and
   wherein the injection channel has a higher inflow-withstanding pressure than the corresponding first high inflow-withstanding pressure section, and does not allow passage of a liquid sample at is liquid sample introduction pressure applied to introduce the liquid sample into the main channel and the metering channel and at a purge pressure applied to purge the liquid sample from the main channel but allows passage of the liquid sample at a pressure higher than the liquid sample introduction pressure and the purge pressure.

2. The dispensing device according to claim 1, wherein the injection channel has a channel inner wall, with at least a part which forms a contact angle of 90° or larger with a liquid sample.

3. The dispensing device according to claim 1,
   wherein one of the branch channels is adjacent to the sample outlet,
   wherein a second high inflow-withstanding pressure section is provided in the main channel between the sample outlet and the first high inflow-withstanding pressure section that is provided between the branch channel that is adjacent to the sample outlet and the sample outlet, so that the second high inflow-withstanding pressure section is spaced from the first high inflow-withstanding pressure section, and
   wherein the second high inflow-withstanding pressure section has an inflow-withstanding pressure equal to or higher than that of the first high inflow-withstanding pressure sections.

4. The dispensing device according to claim 3, wherein the second high inflow-withstanding pressure section has to smaller cross-sectional circumference than the first high inflow-withstanding pressure sections.

5. The dispensing device according to claim 3, wherein the second high inflow-withstanding pressure section comprises a plurality of narrow holes having a smaller cross-sectional circumference than the first high inflow-withstanding pressure sections.

6. The dispensing device according to claim 3, wherein the second high inflow-withstanding pressure section comprises a plurality of projections.

7. The dispensing device according to claim 3,
wherein a liquid waste container is provided in the main channel between the first high inflow-withstanding pressure section that is provided between the branch channel that is adjacent to the sample outlet and the sample outlet, and the second high inflow-withstanding pressure section, and
wherein the second high inflow-withstanding pressure section is provided at a position which does not allow a liquid sample contained in the liquid waste container to come into contact with the second high inflow-withstanding pressure section.

8. A dispensing device comprising:
a base substrate;
a cover substrate whose one surface is bonded to one surface of the base substrate;
a liquid reservoir comprising a recess provided in one or both of the one surface of the base substrate and the one surface of the cover substrate;
a liquid sample introduction channel comprising a groove provided in one or both of the one surface of the base substrate and the one surface of the cover substrate, the liquid sample introduction channel being connected to the liquid reservoir; and
an air vent port provided in one or both of the one surface of the base substrate and the one surface of the cover substrate and connected to the liquid reservoir at a position different from a position where the liquid sample introduction channel is connected to the liquid reservoir,
wherein the number of the liquid reservoirs is two or more,
the liquid sample introduction channel includes a main channel and a plurality of branch channels, one end of the main channel being connected to a sample inlet and the other end of the main channel being connected to a sample outlet, the branch channels being connected to the main channel between the sample inlet and the sample outlet,
the branch channels are each connected to the different liquid reservoirs at their ends located on an opposite side from the main channel,
a first high inflow-withstanding pressure section is provided in the main channel between one branch channel and the sample outlet, and
the first high inflow-withstanding pressure section has a higher inflow-withstanding pressure than the one branch channel,
wherein the branch channel includes a metering channel and an injection channel, one end of the metering channel being connected to the main channel and the metering channel having a predetermined capacity, one end of the injection channel being connected to the other end of the metering channel and the other end of the injection channel being connected to the liquid reservoir,
wherein a liquid sample introduced into the main channel through the sample inlet is more likely to flow into the main channel than into the metering channel at a branch point between the main channel and the metering channel, and
wherein the injection channel has a higher inflow-withstanding pressure than the first high inflow-withstanding pressure section, and does not allow passage of a liquid sample at a liquid sample introduction pressure applied to introduce the liquid sample into the main channel and the metering channel and at a purge pressure applied to purge the liquid sample from the main channel but allows passage of the liquid sample at a pressure higher than the liquid sample introduction pressure and the purge pressure.

9. The dispensing device according to claim 8, wherein the injection channel has a channel inner wall, with at least a part which forms a contact angle of 90° or larger with a liquid sample.

10. The dispensing device according to claim 8,
wherein a second high inflow-withstanding pressure section is provided in the main channel between the first high inflow-withstanding pressure section and the sample outlet so as to be spaced from the first high inflow-withstanding pressure section, and
wherein the second high inflow-withstanding pressure section has a higher inflow-withstanding pressure than the first high inflow-withstanding pressure section.

11. The dispensing device according to claim 10,
wherein a liquid waste container is provided in the main channel between the first high inflow-withstanding pressure section and the second high inflow-withstanding pressure section, and
wherein the second high inflow-withstanding pressure section is provided at a position which does not allow a liquid sample contained in the liquid waste container to come into contact with the second high inflow-withstanding pressure section.

12. The dispensing device according to claim 10, wherein the second high inflow-withstanding pressure section has a channel inner wall, with at least a part which forms a contact angle of 90° or larger with a liquid sample.

13. The dispensing device according to claim 12, wherein the second high inflow-withstanding pressure section has a smaller cross-sectional circumference than the first high inflow-withstanding pressure section.

14. The dispensing device according to claim 12, wherein the second high inflow-withstanding pressure section comprises a plurality of narrow holes having a smaller cross-sectional circumference than the first high inflow-withstanding pressure section.

15. The dispensing device according to claim 12, wherein the second high inflow-withstanding pressure section comprises a plurality of projections.

* * * * *